(12) United States Patent
Jackson

(10) Patent No.: US 9,035,034 B2
(45) Date of Patent: May 19, 2015

(54) FUNCTIONAL LIGANDS TO TARGET MOLECULES

(71) Applicant: George W. Jackson, Pearland, TX (US)

(72) Inventor: George W. Jackson, Pearland, TX (US)

(73) Assignee: Base Pair Biotechnologies, Inc., Houston, TX (US)

( * ) Notice: Subject to any disclaimer, the term of this patent is extended or adjusted under 35 U.S.C. 154(b) by 20 days.

(21) Appl. No.: 13/748,566

(22) Filed: Jan. 23, 2013

(65) Prior Publication Data

US 2013/0245243 A1   Sep. 19, 2013

Related U.S. Application Data

(63) Continuation-in-part of application No. 13/493,996, filed on Jun. 11, 2012, now abandoned, which is a continuation-in-part of application No. 12/683,429, filed on Jan. 7, 2010, now Pat. No. 8,314,052.

(60) Provisional application No. 61/162,394, filed on Mar. 23, 2009, provisional application No. 61/495,976, filed on Jun. 11, 2011.

(51) Int. Cl.
*C07H 21/04* (2006.01)
*C12N 15/115* (2010.01)

(52) U.S. Cl.
CPC .......... *C12N 15/115* (2013.01); *C12N 2310/16* (2013.01); *C12N 2320/11* (2013.01); *C12N 2330/31* (2013.01)

(58) Field of Classification Search
None
See application file for complete search history.

(56) References Cited

U.S. PATENT DOCUMENTS

2007/0050146 A1 *   3/2007   Bentwich et al. ............... 702/19

* cited by examiner

*Primary Examiner* — Jennifer McDonald
(74) *Attorney, Agent, or Firm* — Christopher Quan

(57) ABSTRACT

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules. The present invention further relates to methods for generating, for example, functional biomolecules, particularly to functional nucleic acids, that bind with functional activity to another biomolecule, such as a receptor molecule. More than one or multiple targets as used herein may generally include different types of targets, and/or may also include a multitude of a singular type of targets at different conditions, such as, for example, temperature, pH, chemical environment, and/or any other appropriate conditions.

2 Claims, 5 Drawing Sheets

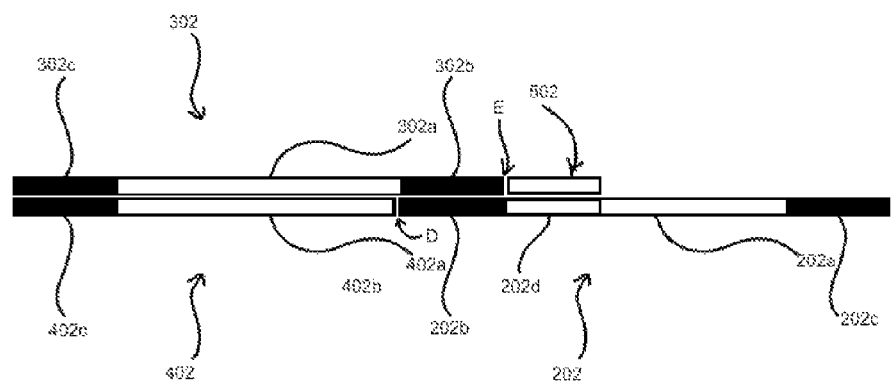
*Fig. 6c.*
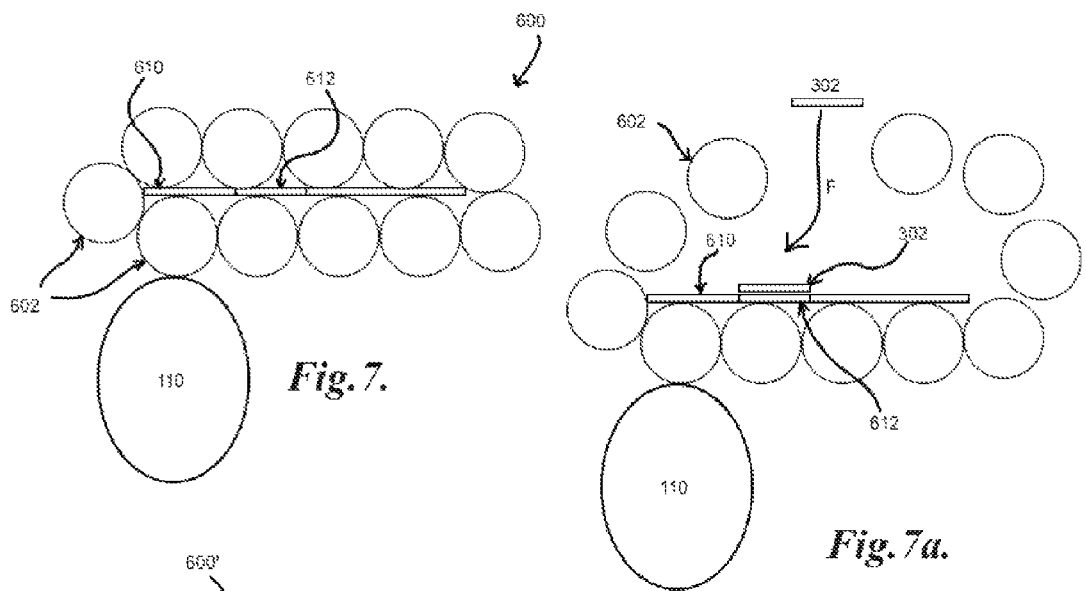
*Fig. 7.*
*Fig. 7a.*
*Fig. 7b.*
*Fig. 7c.*

SEQUENCE LISTING

<160> NUMBER OF SEQ ID NOS: 547

<210> SEQ ID NO 1
<211> LENGTH: 40
<212> TYPE: DNA
<213> ORGANISM: Artificial
<220> FEATURE:
<223> OTHER INFORMATION: DNA Aptamer

<400> SEQUENCE: 1
caagagtgtt agacattatc tcagcgctgc caattatatt                40

<210> SEQ ID NO 2
<211> LENGTH: 39
<212> TYPE: DNA
<213> ORGANISM: Artificial
<220> FEATURE:
<223> OTHER INFORMATION: DNA Aptamer

<400> SEQUENCE: 2
agaggcggct gagatcaatc tccgctcagg gagcgagta                 39

<210> SEQ ID NO 3
<211> LENGTH: 40
<212> TYPE: DNA
<213> ORGANISM: Artificial
<220> FEATURE:
<223> OTHER INFORMATION: DNA Aptamer

<400> SEQUENCE: 3
caatacaata ctatatttgt gtcaatctcg tacttctgac                40

<210> SEQ ID NO 4
<211> LENGTH: 40
<212> TYPE: DNA
<213> ORGANISM: Artificial
<220> FEATURE:
<223> OTHER INFORMATION: DNA Aptamer

<400> SEQUENCE: 4
caatatgtct aattttttta catggcggca tggtattggc                40

<210> SEQ ID NO 5
<211> LENGTH: 40
<212> TYPE: DNA
<213> ORGANISM: Artificial
<220> FEATURE:
<223> OTHER INFORMATION: DNA Aptamer

<400> SEQUENCE: 5
aagatcttta ttaagcaaac aatgttaact atagagcgtt                40

<210> SEQ ID NO 6
<211> LENGTH: 41
<212> TYPE: DNA
<213> ORGANISM: Artificial
<220> FEATURE:
<223> OTHER INFORMATION: DNA Aptamer

<400> SEQUENCE: 6
gaattacatt caaaaatttt cttctggcat ctgtaatacc g              41

<210> SEQ ID NO 7
<211> LENGTH: 40
<212> TYPE: DNA
<213> ORGANISM: Artificial

```
<220> FEATURE:
<223> OTHER INFORMATION: DNA Aptamer

<400> SEQUENCE: 7
tgatacaaat actctcaatc aaagccaata tgtcgcaaaa                              40

<210> SEQ ID NO 8
<211> LENGTH: 40
<212> TYPE: DNA
<213> ORGANISM: Artificial
<220> FEATURE:
<223> OTHER INFORMATION: DNA Aptamer

<400> SEQUENCE: 8
caaagtaaaa ttaacagata gtacgttctc aatctcgcga                              40

<210> SEQ ID NO 9
<211> LENGTH: 40
<212> TYPE: DNA
<213> ORGANISM: Artificial
<220> FEATURE:
<223> OTHER INFORMATION: DNA Aptamer

<400> SEQUENCE: 9
tcttcttgca catattttc tccgtgagac atgtaaataa                               40

<210> SEQ ID NO 10
<211> LENGTH: 40
<212> TYPE: DNA
<213> ORGANISM: Artificial
<220> FEATURE:
<223> OTHER INFORMATION: DNA Aptamer

<400> SEQUENCE: 10
atgtacttca cttcagtttt ctttaaacac gtttcacata                              40

<210> SEQ ID NO 11
<211> LENGTH: 39
<212> TYPE: DNA
<213> ORGANISM: Artificial
<220> FEATURE:
<223> OTHER INFORMATION: DNA Aptamer

<400> SEQUENCE: 11
ccgcatttat cagtttaccg ccccataaac ataaccgct                               39

<210> SEQ ID NO 12
<211> LENGTH: 40
<212> TYPE: DNA
<213> ORGANISM: Artificial
<220> FEATURE:
<223> OTHER INFORMATION: DNA Aptamer

<400> SEQUENCE: 12
aattatgctc atgattttct tcaaaaggc tcgcgcaatt                               40

<210> SEQ ID NO 13
<211> LENGTH: 40
<212> TYPE: DNA
<213> ORGANISM: Artificial
<220> FEATURE:
<223> OTHER INFORMATION: DNA Aptamer

<400> SEQUENCE: 13
ggctgttaaa cttactttc ttcagtaatt gccgttgaca                               40
```

<210> SEQ ID NO 14
<211> LENGTH: 40
<212> TYPE: DNA
<213> ORGANISM: Artificial
<220> FEATURE:
<223> OTHER INFORMATION: DNA Aptamer

<400> SEQUENCE: 14
tagtttatca ggagcgatca ctgatcatga gtaacttta                      40

<210> SEQ ID NO 15
<211> LENGTH: 40
<212> TYPE: DNA
<213> ORGANISM: Artificial
<220> FEATURE:
<223> OTHER INFORMATION: DNA Aptamer

<400> SEQUENCE: 15
atcaagaatt gataatttta ggaattgcgt atcgctgcta                      40

<210> SEQ ID NO 16
<211> LENGTH: 40
<212> TYPE: DNA
<213> ORGANISM: Artificial
<220> FEATURE:
<223> OTHER INFORMATION: DNA Aptamer

<400> SEQUENCE: 16
aactgtgttt taggacttca ttgtcttaat tctcttccct                      40

<210> SEQ ID NO 17
<211> LENGTH: 40
<212> TYPE: DNA
<213> ORGANISM: Artificial
<220> FEATURE:
<223> OTHER INFORMATION: DNA Aptamer

<400> SEQUENCE: 17
agcgcgatat tacggtctcg aaccaaaacc atcacggttc                      40

<210> SEQ ID NO 18
<211> LENGTH: 38
<212> TYPE: DNA
<213> ORGANISM: Artificial
<220> FEATURE:
<223> OTHER INFORMATION: DNA Aptamer

<400> SEQUENCE: 18
atagtttaaa tttaatcttc tgccaccctt cactttca                        38

<210> SEQ ID NO 19
<211> LENGTH: 40
<212> TYPE: DNA
<213> ORGANISM: Artificial
<220> FEATURE:
<223> OTHER INFORMATION: DNA Aptamer

<400> SEQUENCE: 19
gcacatctcc cgttcgactt ttttatcttc gagcacctaa                      40

<210> SEQ ID NO 20
<211> LENGTH: 40
<212> TYPE: DNA
<213> ORGANISM: Artificial
<220> FEATURE:
<223> OTHER INFORMATION: DNA Aptamer

<400> SEQUENCE: 20
ccatgtagca caaaacaacg atataagaac tacatttagt         40

<210> SEQ ID NO 21
<211> LENGTH: 40
<212> TYPE: DNA
<213> ORGANISM: Artificial
<220> FEATURE:
<223> OTHER INFORMATION: DNA Aptamer

<400> SEQUENCE: 21
ggctttctaa tctaacacga tctcctctcc ttacgccgtg         40

<210> SEQ ID NO 22
<211> LENGTH: 40
<212> TYPE: DNA
<213> ORGANISM: Artificial
<220> FEATURE:
<223> OTHER INFORMATION: DNA Aptamer

<400> SEQUENCE: 22
tactcttgtt taaactagaa cagtaaaata ttaattctta         40

<210> SEQ ID NO 23
<211> LENGTH: 40
<212> TYPE: DNA
<213> ORGANISM: Artificial
<220> FEATURE:
<223> OTHER INFORMATION: DNA Aptamer

<400> SEQUENCE: 23
tggagtttat aatactcgag gctagtagtg ccattttaca         40

<210> SEQ ID NO 24
<211> LENGTH: 40
<212> TYPE: DNA
<213> ORGANISM: Artificial
<220> FEATURE:
<223> OTHER INFORMATION: DNA Aptamer

<400> SEQUENCE: 24
acgcgcggct gtgggaagg tacaggttcc gaacgatgga         40

<210> SEQ ID NO 25
<211> LENGTH: 40
<212> TYPE: DNA
<213> ORGANISM: Artificial
<220> FEATURE:
<223> OTHER INFORMATION: DNA Aptamer

<400> SEQUENCE: 25
acaagaacta tttttatcaa agacgtcacc aacttaaggc         40

<210> SEQ ID NO 26
<211> LENGTH: 40
<212> TYPE: DNA
<213> ORGANISM: Artificial
<220> FEATURE:
<223> OTHER INFORMATION: DNA Aptamer

<400> SEQUENCE: 26
caaataatcg ttttataatt accaacacat tttggttaac         40

<210> SEQ ID NO 27

```
<211> LENGTH: 40
<212> TYPE: DNA
<213> ORGANISM: Artificial
<220> FEATURE:
<223> OTHER INFORMATION: DNA Aptamer

<400> SEQUENCE: 27
tttatattaa gcaactttt gagagttgat tgataattta                              40

<210> SEQ ID NO 28
<211> LENGTH: 40
<212> TYPE: DNA
<213> ORGANISM: Artificial
<220> FEATURE:
<223> OTHER INFORMATION: DNA Aptamer

<400> SEQUENCE: 28
tggcctaatc tcggagactg gccgctgtgg gcgcgggcct                             40

<210> SEQ ID NO 29
<211> LENGTH: 40
<212> TYPE: DNA
<213> ORGANISM: Artificial
<220> FEATURE:
<223> OTHER INFORMATION: DNA Aptamer

<400> SEQUENCE: 29
tctaattatg ttacaaaata attgttatgc tccgcaaata                             40

<210> SEQ ID NO 30
<211> LENGTH: 39
<212> TYPE: DNA
<213> ORGANISM: Artificial
<220> FEATURE:
<223> OTHER INFORMATION: DNA Aptamer

<400> SEQUENCE: 30
tcatttaatt gtcctaaatc tgaaaattta ttatatttc                              39

<210> SEQ ID NO 31
<211> LENGTH: 40
<212> TYPE: DNA
<213> ORGANISM: Artificial
<220> FEATURE:
<223> OTHER INFORMATION: DNA Aptamer

<400> SEQUENCE: 31
ccgggataaa ttactaagtt tcgggtattt tgacaatatt                             40

<210> SEQ ID NO 32
<211> LENGTH: 40
<212> TYPE: DNA
<213> ORGANISM: Artificial
<220> FEATURE:
<223> OTHER INFORMATION: DNA Aptamer

<400> SEQUENCE: 32
aaacctgcaa aatttagggc caatgtgtgt attgaacggg                             40

<210> SEQ ID NO 33
<211> LENGTH: 40
<212> TYPE: DNA
<213> ORGANISM: Artificial
<220> FEATURE:
<223> OTHER INFORMATION: DNA Aptamer

<400> SEQUENCE: 33
```

```
gttatagtaa tattggttct agctctcagt aatatcaaaa                              40
```

<210> SEQ ID NO 34
<211> LENGTH: 40
<212> TYPE: DNA
<213> ORGANISM: Artificial
<220> FEATURE:
<223> OTHER INFORMATION: DNA Aptamer

<400> SEQUENCE: 34

```
accctataag ctgagataag cattctgtgg acgaaaagtt                              40
```

<210> SEQ ID NO 35
<211> LENGTH: 40
<212> TYPE: DNA
<213> ORGANISM: Artificial
<220> FEATURE:
<223> OTHER INFORMATION: DNA Aptamer

<400> SEQUENCE: 35

```
aggcgttaac tcttgtcatg ttatagacgt ctaatccatc                              40
```

<210> SEQ ID NO 36
<211> LENGTH: 40
<212> TYPE: DNA
<213> ORGANISM: Artificial
<220> FEATURE:
<223> OTHER INFORMATION: DNA Aptamer

<400> SEQUENCE: 36

```
actgtaatca cttcttttaa atagtcccgg aacgatatca                              40
```

<210> SEQ ID NO 37
<211> LENGTH: 40
<212> TYPE: DNA
<213> ORGANISM: Artificial
<220> FEATURE:
<223> OTHER INFORMATION: DNA Aptamer

<400> SEQUENCE: 37

```
cttgatccat actataactt aacatttgtt catctcaagt                              40
```

<210> SEQ ID NO 38
<211> LENGTH: 40
<212> TYPE: DNA
<213> ORGANISM: Artificial
<220> FEATURE:
<223> OTHER INFORMATION: DNA Aptamer

<400> SEQUENCE: 38

```
ctaaatcgcg aaccgagttt ttgtcaaagt tctagattaa                              40
```

<210> SEQ ID NO 39
<211> LENGTH: 40
<212> TYPE: DNA
<213> ORGANISM: Artificial
<220> FEATURE:
<223> OTHER INFORMATION: DNA Aptamer

<400> SEQUENCE: 39

```
acgaactttt ttaattcgca gacatgttta tagtttcttg                              40
```

<210> SEQ ID NO 40
<211> LENGTH: 40
<212> TYPE: DNA

```
<213> ORGANISM: Artificial
<220> FEATURE:
<223> OTHER INFORMATION: DNA Aptamer

<400> SEQUENCE: 40
gagggggggg ccaggccgcc aggagcgaag gtcccggccc                              40

<210> SEQ ID NO 41
<211> LENGTH: 40
<212> TYPE: DNA
<213> ORGANISM: Artificial
<220> FEATURE:
<223> OTHER INFORMATION: DNA Aptamer

<400> SEQUENCE: 41
cgtggttgga ttgggggggcg tgttcgcctg agtgcaaggc                             40

<210> SEQ ID NO 42
<211> LENGTH: 40
<212> TYPE: DNA
<213> ORGANISM: Artificial
<220> FEATURE:
<223> OTHER INFORMATION: DNA Aptamer

<400> SEQUENCE: 42
tacgcggttt ttgtatccca aaccattgca tcatctctaa                              40

<210> SEQ ID NO 43
<211> LENGTH: 40
<212> TYPE: DNA
<213> ORGANISM: Artificial
<220> FEATURE:
<223> OTHER INFORMATION: DNA Aptamer

<400> SEQUENCE: 43
gtcattcttt tagtattaaa tttagaatta ctcctccaga                              40

<210> SEQ ID NO 44
<211> LENGTH: 40
<212> TYPE: DNA
<213> ORGANISM: Artificial
<220> FEATURE:
<223> OTHER INFORMATION: DNA Aptamer

<400> SEQUENCE: 44
caaagaaaat ggtcatgaaa tagcgtacta acatggagtc                              40

<210> SEQ ID NO 45
<211> LENGTH: 40
<212> TYPE: DNA
<213> ORGANISM: Artificial
<220> FEATURE:
<223> OTHER INFORMATION: DNA Aptamer

<400> SEQUENCE: 45
ctagtttatc ttataacgaa atgttgtttt tatgctttca                              40

<210> SEQ ID NO 46
<211> LENGTH: 38
<212> TYPE: DNA
<213> ORGANISM: Artificial
<220> FEATURE:
<223> OTHER INFORMATION: DNA Aptamer

<400> SEQUENCE: 46
tgcaaaagag ccctactctt gctctcagat cccttctc                                38
```

<210> SEQ ID NO 47
<211> LENGTH: 31
<212> TYPE: DNA
<213> ORGANISM: Artificial
<220> FEATURE:
<223> OTHER INFORMATION: DNA Aptamer

<400> SEQUENCE: 47
ttcgaattct atcaatttga gacgatttag t                              31

<210> SEQ ID NO 48
<211> LENGTH: 38
<212> TYPE: DNA
<213> ORGANISM: Artificial
<220> FEATURE:
<223> OTHER INFORMATION: DNA Aptamer

<400> SEQUENCE: 48
aggtcgttta tgactaacac tttagattcg acacacag                       38

<210> SEQ ID NO 49
<211> LENGTH: 39
<212> TYPE: DNA
<213> ORGANISM: Artificial
<220> FEATURE:
<223> OTHER INFORMATION: DNA Aptamer

<400> SEQUENCE: 49
agttgtttgg tcgatatggc ctttgctcca gggttgccg                      39

<210> SEQ ID NO 50
<211> LENGTH: 38
<212> TYPE: DNA
<213> ORGANISM: Artificial
<220> FEATURE:
<223> OTHER INFORMATION: DNA Aptamer

<400> SEQUENCE: 50
acaaaagaaa ggttgcatcg aacagataac ttacatat                       38

<210> SEQ ID NO 51
<211> LENGTH: 40
<212> TYPE: DNA
<213> ORGANISM: Artificial
<220> FEATURE:
<223> OTHER INFORMATION: DNA Aptamer

<400> SEQUENCE: 51
gagtgaatgt caggtgcatg aatgtttccg tatagcgcga                     40

<210> SEQ ID NO 52
<211> LENGTH: 38
<212> TYPE: DNA
<213> ORGANISM: Artificial
<220> FEATURE:
<223> OTHER INFORMATION: DNA Aptamer

<400> SEQUENCE: 52
tagattaatt ggatgttgta tacctagtat agccattg                       38

<210> SEQ ID NO 53
<211> LENGTH: 38
<212> TYPE: DNA
<213> ORGANISM: Artificial
<220> FEATURE:

<223> OTHER INFORMATION: DNA Aptamer

<400> SEQUENCE: 53
aagcgcgtta tcagtataaa ggaaacataa catactcg                    38

<210> SEQ ID NO 54
<211> LENGTH: 39
<212> TYPE: DNA
<213> ORGANISM: Artificial
<220> FEATURE:
<223> OTHER INFORMATION: DNA Aptamer

<400> SEQUENCE: 54
taattattta gtaatagatt aagtttctta gatgctaac                   39

<210> SEQ ID NO 55
<211> LENGTH: 40
<212> TYPE: DNA
<213> ORGANISM: Artificial
<220> FEATURE:
<223> OTHER INFORMATION: DNA Aptamer

<400> SEQUENCE: 55
agacttgaaa gcatctttac ttcgattggt aatattttg                   40

<210> SEQ ID NO 56
<211> LENGTH: 40
<212> TYPE: DNA
<213> ORGANISM: Artificial
<220> FEATURE:
<223> OTHER INFORMATION: DNA Aptamer

<400> SEQUENCE: 56
ttgaaggcgt accgtccgcg ggcggcgtgt gcgccgggcc                  40

<210> SEQ ID NO 57
<211> LENGTH: 40
<212> TYPE: DNA
<213> ORGANISM: Artificial
<220> FEATURE:
<223> OTHER INFORMATION: DNA Aptamer

<400> SEQUENCE: 57
ttgaaggcgt accgtccgcg ggcggcgtgt gcgccgggcc                  40

<210> SEQ ID NO 58
<211> LENGTH: 40
<212> TYPE: DNA
<213> ORGANISM: Artificial
<220> FEATURE:
<223> OTHER INFORMATION: DNA Aptamer

<400> SEQUENCE: 58
gggggcgcgt cgcagggggg gacgcgggaa tcgaggagca                  40

<210> SEQ ID NO 59
<211> LENGTH: 40
<212> TYPE: DNA
<213> ORGANISM: Artificial
<220> FEATURE:
<223> OTHER INFORMATION: DNA Aptamer

<400> SEQUENCE: 59
ggggccgatt cggccagtcc gggggggcccg acatcggaga                 40

```
<210> SEQ ID NO 60
<211> LENGTH: 40
<212> TYPE: DNA
<213> ORGANISM: Artificial
<220> FEATURE:
<223> OTHER INFORMATION: DNA Aptamer

<400> SEQUENCE: 60
cggaaaatta ttctgtaatt ttctaactct ggttagactt                              40

<210> SEQ ID NO 61
<211> LENGTH: 40
<212> TYPE: DNA
<213> ORGANISM: Artificial
<220> FEATURE:
<223> OTHER INFORMATION: DNA Aptamer

<400> SEQUENCE: 61
ccaatttggg atatgcttca ggatccctg agtatggttt                               40

<210> SEQ ID NO 62
<211> LENGTH: 40
<212> TYPE: DNA
<213> ORGANISM: Artificial
<220> FEATURE:
<223> OTHER INFORMATION: DNA Aptamer

<400> SEQUENCE: 62
caaacgcatt agatcgaatc taattgttgc aacaaagtca                              40

<210> SEQ ID NO 63
<211> LENGTH: 40
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (25)..(25)
<223> OTHER INFORMATION: n is a, c, g, or t

<400> SEQUENCE: 63
cagggattta tcccccatgc ggacncgtag ccacccggaa                              40

<210> SEQ ID NO 64
<211> LENGTH: 40
<212> TYPE: DNA
<213> ORGANISM: Artificial
<220> FEATURE:
<223> OTHER INFORMATION: DNA Aptamer

<400> SEQUENCE: 64
cgttagtttt ctttacgtga aaacagtttg acttacgcca                              40

<210> SEQ ID NO 65
<211> LENGTH: 40
<212> TYPE: DNA
<213> ORGANISM: Artificial
<220> FEATURE:
<223> OTHER INFORMATION: DNA Aptamer

<400> SEQUENCE: 65
cgttttatta tgggtttata aaacatcagc atcacaagat                              40

<210> SEQ ID NO 66
<211> LENGTH: 40
<212> TYPE: DNA
```

<213> ORGANISM: Artificial
<220> FEATURE:
<223> OTHER INFORMATION: DNA Aptamer

<400> SEQUENCE: 66
atttataggg tctgtattaa aacaatttta atttcactct                              40

<210> SEQ ID NO 67
<211> LENGTH: 40
<212> TYPE: DNA
<213> ORGANISM: Artificial
<220> FEATURE:
<223> OTHER INFORMATION: DNA Aptamer

<400> SEQUENCE: 67
ccacggggtg ggattctatt atttaactaa ctaatgtaca                              40

<210> SEQ ID NO 68
<211> LENGTH: 40
<212> TYPE: DNA
<213> ORGANISM: Artificial
<220> FEATURE:
<223> OTHER INFORMATION: DNA Aptamer

<400> SEQUENCE: 68
aagggatgtt tggcgttctg attaacgtta ggaaccatgt                              40

<210> SEQ ID NO 69
<211> LENGTH: 40
<212> TYPE: DNA
<213> ORGANISM: Artificial
<220> FEATURE:
<223> OTHER INFORMATION: DNA Aptamer

<400> SEQUENCE: 69
tgaaataaat tcttgaagag aaccatttat cgggtcgtca                              40

<210> SEQ ID NO 70
<211> LENGTH: 40
<212> TYPE: DNA
<213> ORGANISM: Artificial
<220> FEATURE:
<223> OTHER INFORMATION: DNA Aptamer

<400> SEQUENCE: 70
cgggggttcc ctgtaatata aagtgtcatt tagtgcgcct                              40

<210> SEQ ID NO 71
<211> LENGTH: 38
<212> TYPE: DNA
<213> ORGANISM: Artificial
<220> FEATURE:
<223> OTHER INFORMATION: DNA Aptamer

<400> SEQUENCE: 71
cgaatttagt taatgatcgt aatattacaa ataaattt                                38

<210> SEQ ID NO 72
<211> LENGTH: 40
<212> TYPE: DNA
<213> ORGANISM: Artificial
<220> FEATURE:
<223> OTHER INFORMATION: DNA Aptamer

<400> SEQUENCE: 72
gcaattttca gggtatcaac aggcccatat ggatcatcac                              40

<210> SEQ ID NO 73
<211> LENGTH: 40
<212> TYPE: DNA
<213> ORGANISM: Artificial
<220> FEATURE:
<223> OTHER INFORMATION: DNA Aptamer

<400> SEQUENCE: 73
cgaagttgag ttatttattt atctcatcta atagtcagtt                                40

<210> SEQ ID NO 74
<211> LENGTH: 40
<212> TYPE: DNA
<213> ORGANISM: Artificial
<220> FEATURE:
<223> OTHER INFORMATION: DNA Aptamer

<400> SEQUENCE: 74
catggtgttt attgatcaat ctttgaccgt agaggaatat                                40

<210> SEQ ID NO 75
<211> LENGTH: 40
<212> TYPE: DNA
<213> ORGANISM: Artificial
<220> FEATURE:
<223> OTHER INFORMATION: DNA Aptamer

<400> SEQUENCE: 75
gtagttttca aatttaagcg gcgtgaactt aataagtact                                40

<210> SEQ ID NO 76
<211> LENGTH: 39
<212> TYPE: DNA
<213> ORGANISM: Artificial
<220> FEATURE:
<223> OTHER INFORMATION: DNA Aptamer

<400> SEQUENCE: 76
ggcttttatt cgtgccgttt aacagacaaa atcattcac                                 39

<210> SEQ ID NO 77
<211> LENGTH: 40
<212> TYPE: DNA
<213> ORGANISM: Artificial
<220> FEATURE:
<223> OTHER INFORMATION: DNA Aptamer

<400> SEQUENCE: 77
aggtattatt ttacaaaaga attagctata accgaataga                                40

<210> SEQ ID NO 78
<211> LENGTH: 40
<212> TYPE: DNA
<213> ORGANISM: Artificial
<220> FEATURE:
<223> OTHER INFORMATION: DNA Aptamer

<400> SEQUENCE: 78
aggtattatt ttacaaaaga attagctata accgaataga                                40

<210> SEQ ID NO 79
<211> LENGTH: 39
<212> TYPE: DNA
<213> ORGANISM: Artificial
<220> FEATURE:

<223> OTHER INFORMATION: DNA Aptamer

<400> SEQUENCE: 79
tttaagttaa tagtagttct gaagacgatt accccgtga                                39

<210> SEQ ID NO 80
<211> LENGTH: 35
<212> TYPE: DNA
<213> ORGANISM: Artificial
<220> FEATURE:
<223> OTHER INFORMATION: DNA Aptamer

<400> SEQUENCE: 80
agctaatact ttatttcttt agagagttgt gcata                                    35

<210> SEQ ID NO 81
<211> LENGTH: 40
<212> TYPE: DNA
<213> ORGANISM: Artificial
<220> FEATURE:
<223> OTHER INFORMATION: DNA Aptamer

<400> SEQUENCE: 81
gtgttacttt tttttctggt gaacgagtta actacttcaa                               40

<210> SEQ ID NO 82
<211> LENGTH: 40
<212> TYPE: DNA
<213> ORGANISM: Artificial
<220> FEATURE:
<223> OTHER INFORMATION: DNA Aptamer

<400> SEQUENCE: 82
gttgtagttt taagattaag tgtacgcatg ttacgggtat                               40

<210> SEQ ID NO 83
<211> LENGTH: 39
<212> TYPE: DNA
<213> ORGANISM: Artificial
<220> FEATURE:
<223> OTHER INFORMATION: DNA Aptamer

<400> SEQUENCE: 83
attaatattt aatcaaggct ctcaacattt tcatactat                                39

<210> SEQ ID NO 84
<211> LENGTH: 40
<212> TYPE: DNA
<213> ORGANISM: Artificial
<220> FEATURE:
<223> OTHER INFORMATION: DNA Aptamer

<400> SEQUENCE: 84
agtactattg agattattcg tcatggaaat cggtatcgct                               40

<210> SEQ ID NO 85
<211> LENGTH: 40
<212> TYPE: DNA
<213> ORGANISM: Artificial
<220> FEATURE:
<223> OTHER INFORMATION: DNA Aptamer

<400> SEQUENCE: 85
cgaaaaaacg gttattatta tcttcttatt atctccctca                               40

```
<210> SEQ ID NO 86
<211> LENGTH: 40
<212> TYPE: DNA
<213> ORGANISM: Artificial
<220> FEATURE:
<223> OTHER INFORMATION: DNA Aptamer

<400> SEQUENCE: 86
cgattttggt attaattata tatgcggtgt ggtcgaggtt                              40

<210> SEQ ID NO 87
<211> LENGTH: 40
<212> TYPE: DNA
<213> ORGANISM: Artificial
<220> FEATURE:
<223> OTHER INFORMATION: DNA Aptamer

<400> SEQUENCE: 87
cgtttattta ttgaaccact tttgttatct agcgcttagc                              40

<210> SEQ ID NO 88
<211> LENGTH: 40
<212> TYPE: DNA
<213> ORGANISM: Artificial
<220> FEATURE:
<223> OTHER INFORMATION: DNA Aptamer

<400> SEQUENCE: 88
cttattgtta aaggtctagt tttatttcaa tctcacacct                              40

<210> SEQ ID NO 89
<211> LENGTH: 40
<212> TYPE: DNA
<213> ORGANISM: Artificial
<220> FEATURE:
<223> OTHER INFORMATION: DNA Aptamer

<400> SEQUENCE: 89
gataatttct aaggatgcgc taacataact cactcgtatt                              40

<210> SEQ ID NO 90
<211> LENGTH: 39
<212> TYPE: DNA
<213> ORGANISM: Artificial
<220> FEATURE:
<223> OTHER INFORMATION: DNA Aptamer

<400> SEQUENCE: 90
gtcgttcgtt ccctaatctt ttctccttag ttcaattca                               39

<210> SEQ ID NO 91
<211> LENGTH: 37
<212> TYPE: DNA
<213> ORGANISM: Artificial
<220> FEATURE:
<223> OTHER INFORMATION: DNA Aptamer

<400> SEQUENCE: 91
gtgagatttt ataatacttt aagcacgtat cctgatt                                 37

<210> SEQ ID NO 92
<211> LENGTH: 40
<212> TYPE: DNA
<213> ORGANISM: Artificial
<220> FEATURE:
<223> OTHER INFORMATION: DNA Aptamer
```

<400> SEQUENCE: 92
gtttaatttc gttatttttc taagtttcaa gatttgctca                                  40

<210> SEQ ID NO 93
<211> LENGTH: 40
<212> TYPE: DNA
<213> ORGANISM: Artificial
<220> FEATURE:
<223> OTHER INFORMATION: DNA Aptamer

<400> SEQUENCE: 93
tgtttgttgg aatatttatt tgaaggtccg tatatatctt                                  40

<210> SEQ ID NO 94
<211> LENGTH: 40
<212> TYPE: DNA
<213> ORGANISM: Artificial
<220> FEATURE:
<223> OTHER INFORMATION: DNA Aptamer

<400> SEQUENCE: 94
ggcgcgctgg cgcgcgaagg tggctcggag tgctccgggc                                  40

<210> SEQ ID NO 95
<211> LENGTH: 40
<212> TYPE: DNA
<213> ORGANISM: Artificial
<220> FEATURE:
<223> OTHER INFORMATION: DNA Aptamer

<400> SEQUENCE: 95
gagggcgggc cgggcccggc ccaggaggag ggaggccccg                                  40

<210> SEQ ID NO 96
<211> LENGTH: 40
<212> TYPE: DNA
<213> ORGANISM: Artificial
<220> FEATURE:
<223> OTHER INFORMATION: DNA Aptamer

<400> SEQUENCE: 96
cggataggta ggcccctcc acgggccggg tcggcccggc                                   40

<210> SEQ ID NO 97
<211> LENGTH: 40
<212> TYPE: DNA
<213> ORGANISM: Artificial
<220> FEATURE:
<223> OTHER INFORMATION: DNA Aptamer

<400> SEQUENCE: 97
cagggcgtga aaggagcggg gcaggggccc cgaaacaaac                                  40

<210> SEQ ID NO 98
<211> LENGTH: 40
<212> TYPE: DNA
<213> ORGANISM: Artificial
<220> FEATURE:
<223> OTHER INFORMATION: DNA Aptamer

<400> SEQUENCE: 98
gggttgtttt tacgaaccgg accgaataac ggcaccggcc                                  40

<210> SEQ ID NO 99
<211> LENGTH: 40

```
<212> TYPE: DNA
<213> ORGANISM: Artificial
<220> FEATURE:
<223> OTHER INFORMATION: DNA Aptamer

<400> SEQUENCE: 99
tgggagggct tgggagccag gtcgtcaagg cggggtcccc                    40

<210> SEQ ID NO 100
<211> LENGTH: 40
<212> TYPE: DNA
<213> ORGANISM: Artificial
<220> FEATURE:
<223> OTHER INFORMATION: DNA Aptamer

<400> SEQUENCE: 100
gcatcacata tcgccccgtg actgggccaa aaggccggac                    40

<210> SEQ ID NO 101
<211> LENGTH: 40
<212> TYPE: DNA
<213> ORGANISM: Artificial
<220> FEATURE:
<223> OTHER INFORMATION: DNA Aptamer

<400> SEQUENCE: 101
ccaatgaatt gagtgtgctt tttttttcga aactcaattc                    40

<210> SEQ ID NO 102
<211> LENGTH: 40
<212> TYPE: DNA
<213> ORGANISM: Artificial
<220> FEATURE:
<223> OTHER INFORMATION: DNA Aptamer

<400> SEQUENCE: 102
cagatggacg ttcgtcgtta attgttaagg cgtcgccgtc                    40

<210> SEQ ID NO 103
<211> LENGTH: 40
<212> TYPE: DNA
<213> ORGANISM: Artificial
<220> FEATURE:
<223> OTHER INFORMATION: DNA Aptamer

<400> SEQUENCE: 103
gatattctga gtgatcgatc gtacgatcaa taatctagta                    40

<210> SEQ ID NO 104
<211> LENGTH: 40
<212> TYPE: DNA
<213> ORGANISM: Artificial
<220> FEATURE:
<223> OTHER INFORMATION: DNA Aptamer

<400> SEQUENCE: 104
gggtcgattg gttttgcttc catactatat gtagcaattg                    40

<210> SEQ ID NO 105
<211> LENGTH: 40
<212> TYPE: DNA
<213> ORGANISM: Artificial
<220> FEATURE:
<223> OTHER INFORMATION: DNA Aptamer

<400> SEQUENCE: 105
```
cgatttgtaa tggtttatac catttaggtt tttcgaaaat                                    40

<210> SEQ ID NO 106
<211> LENGTH: 40
<212> TYPE: DNA
<213> ORGANISM: Artificial
<220> FEATURE:
<223> OTHER INFORMATION: DNA Aptamer

<400> SEQUENCE: 106
agctattcta tggagagtca attttcactg catagcagta                                    40

<210> SEQ ID NO 107
<211> LENGTH: 40
<212> TYPE: DNA
<213> ORGANISM: Artificial
<220> FEATURE:
<223> OTHER INFORMATION: DNA Aptamer

<400> SEQUENCE: 107
cagtaatatt ctactttccg atacggcttc gtatgcgatc                                    40

<210> SEQ ID NO 108
<211> LENGTH: 40
<212> TYPE: DNA
<213> ORGANISM: Artificial
<220> FEATURE:
<223> OTHER INFORMATION: DNA Aptamer

<400> SEQUENCE: 108
aggatttaat ctgtgtgatt agcatgttcc gacaccggcc                                    40

<210> SEQ ID NO 109
<211> LENGTH: 40
<212> TYPE: DNA
<213> ORGANISM: Artificial
<220> FEATURE:
<223> OTHER INFORMATION: DNA Aptamer

<400> SEQUENCE: 109
gtggcaaatt tatgtgttct caaaaaacac aaacaacaac                                    40

<210> SEQ ID NO 110
<211> LENGTH: 40
<212> TYPE: DNA
<213> ORGANISM: Artificial
<220> FEATURE:
<223> OTHER INFORMATION: DNA Aptamer

<400> SEQUENCE: 110
cgtaacgacc tgaaattcgg gtactacaga aatccaatta                                    40

<210> SEQ ID NO 111
<211> LENGTH: 38
<212> TYPE: DNA
<213> ORGANISM: Artificial
<220> FEATURE:
<223> OTHER INFORMATION: DNA Aptamer

<400> SEQUENCE: 111
ttgttttatg ttttttgccag actttaaggc accaagct                                     38

<210> SEQ ID NO 112
<211> LENGTH: 40
<212> TYPE: DNA
<213> ORGANISM: Artificial

```
<220> FEATURE:
<223> OTHER INFORMATION: DNA Aptamer

<400> SEQUENCE: 112
ccgattattg ttattctaga agtgagcatg atcgcacact                              40

<210> SEQ ID NO 113
<211> LENGTH: 40
<212> TYPE: DNA
<213> ORGANISM: Artificial
<220> FEATURE:
<223> OTHER INFORMATION: DNA Aptamer

<400> SEQUENCE: 113 cttgttttg aaagcatgtc gctaaatggt agttttcaat                               40

<210> SEQ ID NO 114
<211> LENGTH: 40
<212> TYPE: DNA
<213> ORGANISM: Artificial
<220> FEATURE:
<223> OTHER INFORMATION: DNA Aptamer

<400> SEQUENCE: 114
cagtggaggg gagtgcgttc tggaggagcg gcccgcagac                              40

<210> SEQ ID NO 115
<211> LENGTH: 40
<212> TYPE: DNA
<213> ORGANISM: Artificial
<220> FEATURE:
<223> OTHER INFORMATION: DNA Aptamer

<400> SEQUENCE: 115
ctaggataaa aggtaattga attaacatag gcttttaacg                              40

<210> SEQ ID NO 116
<211> LENGTH: 40
<212> TYPE: DNA
<213> ORGANISM: Artificial
<220> FEATURE:
<223> OTHER INFORMATION: DNA Aptamer

<400> SEQUENCE: 116 ggcgggggc tagcagagcg ggaacgggcg gcggcaacaa                               40

<210> SEQ ID NO 117
<211> LENGTH: 40
<212> TYPE: DNA
<213> ORGANISM: Artificial
<220> FEATURE:
<223> OTHER INFORMATION: DNA Aptamer

<400> SEQUENCE: 117
tgtacggggg gatccaagtt atggacaggc ttcaattaga                              40

<210> SEQ ID NO 118
<211> LENGTH: 40
<212> TYPE: DNA
<213> ORGANISM: Artificial
<220> FEATURE:
<223> OTHER INFORMATION: DNA Aptamer

<400> SEQUENCE: 118
ccttgtcggt aaataccagt actagtacgt tagatacgga                              40
```

<210> SEQ ID NO 119
<211> LENGTH: 40
<212> TYPE: DNA
<213> ORGANISM: Artificial
<220> FEATURE:
<223> OTHER INFORMATION: DNA Aptamer

<400> SEQUENCE: 119
ccttgtcggt aaataccagt actagtacgt tagatacgga        40

<210> SEQ ID NO 120
<211> LENGTH: 40
<212> TYPE: DNA
<213> ORGANISM: Artificial
<220> FEATURE:
<223> OTHER INFORMATION: DNA Aptamer

<400> SEQUENCE: 120
gagaagggga gatgggagg gatacacggg cccgcatatg        40

<210> SEQ ID NO 121
<211> LENGTH: 40
<212> TYPE: DNA
<213> ORGANISM: Artificial
<220> FEATURE:
<223> OTHER INFORMATION: DNA Aptamer

<400> SEQUENCE: 121
agattaaaat atgtagaccc catgttaatc aatgaacact        40

<210> SEQ ID NO 122
<211> LENGTH: 40
<212> TYPE: DNA
<213> ORGANISM: Artificial
<220> FEATURE:
<223> OTHER INFORMATION: DNA Aptamer

<400> SEQUENCE: 122
gagtttggaa tgtatgtgta tatacacgcc cttcattttt        40

<210> SEQ ID NO 123
<211> LENGTH: 39
<212> TYPE: DNA
<213> ORGANISM: Artificial
<220> FEATURE:
<223> OTHER INFORMATION: DNA Aptamer

<400> SEQUENCE: 123
gtctgaagac tagatttctt tttcaaaatg aacaggcca        39

<210> SEQ ID NO 124
<211> LENGTH: 40
<212> TYPE: DNA
<213> ORGANISM: Artificial
<220> FEATURE:
<223> OTHER INFORMATION: DNA Aptamer

<400> SEQUENCE: 124
acgaaatata gttatttagt ccttattaca tttttgcttc        40

<210> SEQ ID NO 125
<211> LENGTH: 36
<212> TYPE: DNA
<213> ORGANISM: Artificial
<220> FEATURE:
<223> OTHER INFORMATION: DNA Aptamer

<400> SEQUENCE: 125
tgttaatgat ttaaagactg tttgataacg cagtaa                                    36

<210> SEQ ID NO 126
<211> LENGTH: 40
<212> TYPE: DNA
<213> ORGANISM: Artificial
<220> FEATURE:
<223> OTHER INFORMATION: DNA Aptamer

<400> SEQUENCE: 126
caatataata aatgttgaac cgtgtaattc ataatacgac                                40

<210> SEQ ID NO 127
<211> LENGTH: 40
<212> TYPE: DNA
<213> ORGANISM: Artificial
<220> FEATURE:
<223> OTHER INFORMATION: DNA Aptamer

<400> SEQUENCE: 127
gaagaaatag cgatgataat ttcaattccg taaaccagtc                                40

<210> SEQ ID NO 128
<211> LENGTH: 40
<212> TYPE: DNA
<213> ORGANISM: Artificial
<220> FEATURE:
<223> OTHER INFORMATION: DNA Aptamer

<400> SEQUENCE: 128
tacatataaa gatgtgtcaa ctagaaatac tttccatact                                40

<210> SEQ ID NO 129
<211> LENGTH: 40
<212> TYPE: DNA
<213> ORGANISM: Artificial
<220> FEATURE:
<223> OTHER INFORMATION: DNA Aptamer

<400> SEQUENCE: 129
attctaaggc ttgaagcagt cctaacctat aactccggtg                                40

<210> SEQ ID NO 130
<211> LENGTH: 40
<212> TYPE: DNA
<213> ORGANISM: Artificial
<220> FEATURE:
<223> OTHER INFORMATION: DNA Aptamer

<400> SEQUENCE: 130
aaggtttatg agtaagtcgg atgcctacaa tatacttaat                                40

<210> SEQ ID NO 131
<211> LENGTH: 40
<212> TYPE: DNA
<213> ORGANISM: Artificial
<220> FEATURE:
<223> OTHER INFORMATION: DNA Aptamer

<400> SEQUENCE: 131
cactgtttgc ggaaagaact tgatttgagt tagtatacca                                40

<210> SEQ ID NO 132

```
<211> LENGTH: 40
<212> TYPE: DNA
<213> ORGANISM: Artificial
<220> FEATURE:
<223> OTHER INFORMATION: DNA Aptamer

<400> SEQUENCE: 132
ttaaggtgta aatttaaaaa tgtttaccta ttctttccac                              40

<210> SEQ ID NO 133
<211> LENGTH: 40
<212> TYPE: DNA
<213> ORGANISM: Artificial
<220> FEATURE:
<223> OTHER INFORMATION: DNA Aptamer

<400> SEQUENCE: 133
cgatttattt gggtaacagt ccatccacgt tatacacacg                              40

<210> SEQ ID NO 134
<211> LENGTH: 30
<212> TYPE: DNA
<213> ORGANISM: Artificial
<220> FEATURE:
<223> OTHER INFORMATION: DNA Aptamer

<400> SEQUENCE: 134
gataatagaa aagcttacgc acatctagac                                        30

<210> SEQ ID NO 135
<211> LENGTH: 40
<212> TYPE: DNA
<213> ORGANISM: Artificial
<220> FEATURE:
<223> OTHER INFORMATION: DNA Aptamer

<400> SEQUENCE: 135
taaatatgtc aattttaatt catgcacacc ccttgactcg                              40

<210> SEQ ID NO 136
<211> LENGTH: 40
<212> TYPE: DNA
<213> ORGANISM: Artificial
<220> FEATURE:
<223> OTHER INFORMATION: DNA Aptamer

<400> SEQUENCE: 136
ccgattattt atcaataaca tatgaatcct aacatccata                              40

<210> SEQ ID NO 137
<211> LENGTH: 40
<212> TYPE: DNA
<213> ORGANISM: Artificial
<220> FEATURE:
<223> OTHER INFORMATION: DNA Aptamer

<400> SEQUENCE: 137
gctattagtt gttgttcaaa tattcgtaca ttcgctgaac                              40

<210> SEQ ID NO 138
<211> LENGTH: 40
<212> TYPE: DNA
<213> ORGANISM: Artificial
<220> FEATURE:
<223> OTHER INFORMATION: DNA Aptamer

<400> SEQUENCE: 138
```

```
attatccttt gttttgaatg cattagttac taaccgctaa                    40

<210> SEQ ID NO 139
<211> LENGTH: 40
<212> TYPE: DNA
<213> ORGANISM: Artificial
<220> FEATURE:
<223> OTHER INFORMATION: DNA Aptamer

<400> SEQUENCE: 139
gtttgtattc aacaggcaca tgctataaga cactttacta                    40

<210> SEQ ID NO 140
<211> LENGTH: 40
<212> TYPE: DNA
<213> ORGANISM: Artificial
<220> FEATURE:
<223> OTHER INFORMATION: DNA Aptamer

<400> SEQUENCE: 140
caggattttt tttgttcagg attatactta cttcctccca                    40

<210> SEQ ID NO 141
<211> LENGTH: 40
<212> TYPE: DNA
<213> ORGANISM: Artificial
<220> FEATURE:
<223> OTHER INFORMATION: DNA Aptamer

<400> SEQUENCE: 141
cggattggca aagagaagac cagtttctag gttatagtgc                    40

<210> SEQ ID NO 142
<211> LENGTH: 40
<212> TYPE: DNA
<213> ORGANISM: Artificial
<220> FEATURE:
<223> OTHER INFORMATION: DNA Aptamer

<400> SEQUENCE: 142
cgggaatgaa cgaggcagac cacactagcg cagatagatt                    40

<210> SEQ ID NO 143
<211> LENGTH: 39
<212> TYPE: DNA
<213> ORGANISM: Artificial
<220> FEATURE:
<223> OTHER INFORMATION: DNA Aptamer

<400> SEQUENCE: 143
gtgatggatt ttggacagct cagttctaac tcccaggaa                     39

<210> SEQ ID NO 144
<211> LENGTH: 40
<212> TYPE: DNA
<213> ORGANISM: Artificial
<220> FEATURE:
<223> OTHER INFORMATION: DNA Aptamer

<400> SEQUENCE: 144
taataattta taaatctgag gtttgcatag tcaactctcc                    40

<210> SEQ ID NO 145
<211> LENGTH: 38
<212> TYPE: DNA
```

```
<213> ORGANISM: Artificial
<220> FEATURE:
<223> OTHER INFORMATION: DNA Aptamer

<400> SEQUENCE: 145
cttgattaac agactatatt tgttcgaatt accacacc                                38

<210> SEQ ID NO 146
<211> LENGTH: 40
<212> TYPE: DNA
<213> ORGANISM: Artificial
<220> FEATURE:
<223> OTHER INFORMATION: DNA Aptamer

<400> SEQUENCE: 146
gtcagaattt tttaggttac ttaggtgact cccatataca                              40

<210> SEQ ID NO 147
<211> LENGTH: 40
<212> TYPE: DNA
<213> ORGANISM: Artificial
<220> FEATURE:
<223> OTHER INFORMATION: DNA Aptamer

<400> SEQUENCE: 147
agaggaaatt ttattctgat ttaagtcatg accccactg                               40

<210> SEQ ID NO 148
<211> LENGTH: 39
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

<400> SEQUENCE: 148
caggtangag tcgntaagtt ttggtcatcc tntgccact                               39

<210> SEQ ID NO 149
<211> LENGTH: 40
<212> TYPE: DNA
<213> ORGANISM: Artificial
<220> FEATURE:
<223> OTHER INFORMATION: DNA Aptamer

<400> SEQUENCE: 149
gatgtattaa ggggcttcca cgttgtgcat gagtaattct                              40

<210> SEQ ID NO 150
<211> LENGTH: 40
<212> TYPE: DNA
<213> ORGANISM: Artificial
<220> FEATURE:
<223> OTHER INFORMATION: DNA Aptamer

<400> SEQUENCE: 150
tagaaaaaaa aagagtgtac tattctacaa taatctactt                              40
```

<210> SEQ ID NO 151
<211> LENGTH: 40
<212> TYPE: DNA
<213> ORGANISM: Artificial
<220> FEATURE:
<223> OTHER INFORMATION: DNA Aptamer

<400> SEQUENCE: 151
tggtgtattt tttagcataa ccttaagatc tcggtacatc                              40

<210> SEQ ID NO 152
<211> LENGTH: 40
<212> TYPE: DNA
<213> ORGANISM: Artificial
<220> FEATURE:
<223> OTHER INFORMATION: DNA Aptamer

<400> SEQUENCE: 152
actttcttta tcgtcgaata ccttaatact gctcattgag                              40

<210> SEQ ID NO 153
<211> LENGTH: 40
<212> TYPE: DNA
<213> ORGANISM: Artificial
<220> FEATURE:
<223> OTHER INFORMATION: DNA Aptamer

<400> SEQUENCE: 153
cactgtatac taacgcatat attcacattt gtcatacttc                              40

<210> SEQ ID NO 154
<211> LENGTH: 40
<212> TYPE: DNA
<213> ORGANISM: Artificial
<220> FEATURE:
<223> OTHER INFORMATION: DNA Aptamer

<400> SEQUENCE: 154
catgtaaatt taaatctttg gtaacggagt tttggccttt                              40

<210> SEQ ID NO 155
<211> LENGTH: 28
<212> TYPE: DNA
<213> ORGANISM: Artificial
<220> FEATURE:
<223> OTHER INFORMATION: DNA Aptamer

<400> SEQUENCE: 155
cgttctatct catacttcat ctccattg                                          28

<210> SEQ ID NO 156
<211> LENGTH: 40
<212> TYPE: DNA
<213> ORGANISM: Artificial
<220> FEATURE:
<223> OTHER INFORMATION: DNA Aptamer

<400> SEQUENCE: 156
ctagacaatt gtattttga tgcttccaca cccaatttac                               40

<210> SEQ ID NO 157
<211> LENGTH: 38
<212> TYPE: DNA
<213> ORGANISM: Artificial
<220> FEATURE:

<223> OTHER INFORMATION: DNA Aptamer

<400> SEQUENCE: 157
gatgtatttt cagcctaatt ctaaagtcaa tatttgtg                                      38

<210> SEQ ID NO 158
<211> LENGTH: 40
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 158
nnnngtngtt ngatganngn ngatnnnngg nagcctttac                                    40

<210> SEQ ID NO 159
<211> LENGTH: 40
<212> TYPE: DNA
<213> ORGANISM: Artificial
<220> FEATURE:
<223> OTHER INFORMATION: DNA Aptamer

<400> SEQUENCE: 159
aggaggggga tcgggcagag gcggacggga cgcccgtgga                                    40

<210> SEQ ID NO 160
<211> LENGTH: 40
<212> TYPE: DNA
<213> ORGANISM: Artificial
<220> FEATURE:
<223> OTHER INFORMATION: DNA Aptamer

<400> SEQUENCE: 160
gacggatttt ataaggttat gatataaacc tcgatcgttg                                    40

<210> SEQ ID NO 161
<211> LENGTH: 40
<212> TYPE: DNA
<213> ORGANISM: Artificial
<220> FEATURE:
<223> OTHER INFORMATION: DNA Aptamer

<400> SEQUENCE: 161
gtattgtaag agaatcttta caactacaat gtatttttat                                    40

<210> SEQ ID NO 162
<211> LENGTH: 40
<212> TYPE: DNA
<213> ORGANISM: Artificial
<220> FEATURE:
<223> OTHER INFORMATION: DNA Aptamer

<400> SEQUENCE: 162
ggttttttta aaatcgtttt ttcattcagc aattagctcg                                    40

<210> SEQ ID NO 163
<211> LENGTH: 40
<212> TYPE: DNA
<213> ORGANISM: Artificial
<220> FEATURE:
<223> OTHER INFORMATION: DNA Aptamer

<400> SEQUENCE: 163
gcgttttttc tgattttcct tatttaatcc actgatgacc                                    40

<210> SEQ ID NO 164
<211> LENGTH: 39
<212> TYPE: DNA
<213> ORGANISM: Artificial
<220> FEATURE:
<223> OTHER INFORMATION: DNA Aptamer

<400> SEQUENCE: 164
tgtaagagat aattttaatc gaattcctgt gttatagcc                                     39

<210> SEQ ID NO 165
<211> LENGTH: 39
<212> TYPE: DNA
<213> ORGANISM: Artificial
<220> FEATURE:
<223> OTHER INFORMATION: DNA Aptamer

<400> SEQUENCE: 165
aggaaacggt ctatgtacca atatttgtac tataggccc                                     39

<210> SEQ ID NO 166
<211> LENGTH: 36
<212> TYPE: DNA
<213> ORGANISM: Artificial
<220> FEATURE:
<223> OTHER INFORMATION: DNA Aptamer

<400> SEQUENCE: 166
ctaatatttt agaaaactta gtaaataggg ctactt                                        36

<210> SEQ ID NO 167
<211> LENGTH: 40
<212> TYPE: DNA
<213> ORGANISM: Artificial
<220> FEATURE:
<223> OTHER INFORMATION: DNA Aptamer

<400> SEQUENCE: 167
gttattttat ttaagccaaa cctctagata cttcactatc                                    40

<210> SEQ ID NO 168
<211> LENGTH: 40
<212> TYPE: DNA

```
<213> ORGANISM: Artificial
<220> FEATURE:
<223> OTHER INFORMATION: DNA Aptamer

<400> SEQUENCE: 168
cgtttaggtt gcctaataaa aatttctcca attttacatc                              40

<210> SEQ ID NO 169
<211> LENGTH: 39
<212> TYPE: DNA
<213> ORGANISM: Artificial
<220> FEATURE:
<223> OTHER INFORMATION: DNA Aptamer

<400> SEQUENCE: 169
ctataagaca tgtttaaata caacctactg attgttatc                               39

<210> SEQ ID NO 170
<211> LENGTH: 39
<212> TYPE: DNA
<213> ORGANISM: Artificial
<220> FEATURE:
<223> OTHER INFORMATION: DNA Aptamer

<400> SEQUENCE: 170
ggaggttaat tgggtcagag cgttaacagg taacgtttt                               39

<210> SEQ ID NO 171
<211> LENGTH: 39
<212> TYPE: DNA
<213> ORGANISM: Artificial
<220> FEATURE:
<223> OTHER INFORMATION: DNA Aptamer

<400> SEQUENCE: 171
ttttatttcg tatcctatat tttcaagtta gcttgactc                               39

<210> SEQ ID NO 172
<211> LENGTH: 40
<212> TYPE: DNA
<213> ORGANISM: Artificial
<220> FEATURE:
<223> OTHER INFORMATION: DNA Aptamer

<400> SEQUENCE: 172
ttgattttac aaaatgcttt aaagtaggta atttgtacca                              40

<210> SEQ ID NO 173
<211> LENGTH: 40
<212> TYPE: DNA
<213> ORGANISM: Artificial
<220> FEATURE:
<223> OTHER INFORMATION: DNA Aptamer

<400> SEQUENCE: 173
cgattattgc tttataaaag acccagacgt catcattatc                              40

<210> SEQ ID NO 174
<211> LENGTH: 33
<212> TYPE: DNA
<213> ORGANISM: Artificial
<220> FEATURE:
<223> OTHER INFORMATION: DNA Aptamer

<400> SEQUENCE: 174
tcaatagttt taatccctaa accgacttca atc                                     33
```

```
<210> SEQ ID NO 175
<211> LENGTH: 40
<212> TYPE: DNA
<213> ORGANISM: Artificial
<220> FEATURE:
<223> OTHER INFORMATION: DNA Aptamer

<400> SEQUENCE: 175
ggtataactc tattgtcgat aaaatccctc ttattcagca                                40

<210> SEQ ID NO 176
<211> LENGTH: 39
<212> TYPE: DNA
<213> ORGANISM: Artificial
<220> FEATURE:
<223> OTHER INFORMATION: DNA Aptamer

<400> SEQUENCE: 176
ctcttaatgt cacggctgag cctatgctgg cgtgaccga                                 39

<210> SEQ ID NO 177
<211> LENGTH: 40
<212> TYPE: DNA
<213> ORGANISM: Artificial
<220> FEATURE:
<223> OTHER INFORMATION: DNA Aptamer

<400> SEQUENCE: 177
gtttaaataa tgaatacagg tatgtatttg ggtcatcctg                                40

<210> SEQ ID NO 178
<211> LENGTH: 40
<212> TYPE: DNA
<213> ORGANISM: Artificial
<220> FEATURE:
<223> OTHER INFORMATION: DNA Aptamer

<400> SEQUENCE: 178
tggatcttta cttgtttact acaaggttat tatcgcttaa                                40

<210> SEQ ID NO 179
<211> LENGTH: 39
<212> TYPE: DNA
<213> ORGANISM: Artificial
<220> FEATURE:
<223> OTHER INFORMATION: DNA Aptamer

<400> SEQUENCE: 179
gtgggttttt tcaagctttt actgcgcccg cgtgagcgt                                 39

<210> SEQ ID NO 180
<211> LENGTH: 38
<212> TYPE: DNA
<213> ORGANISM: Artificial
<220> FEATURE:
<223> OTHER INFORMATION: DNA Aptamer

<400> SEQUENCE: 180
tgaatagtgt cgcgactggg gctggacctg cttgatgg                                  38

<210> SEQ ID NO 181
<211> LENGTH: 40
<212> TYPE: DNA
<213> ORGANISM: Artificial
<220> FEATURE:
```

<223> OTHER INFORMATION: DNA Aptamer

<400> SEQUENCE: 181
tacaaattgt cttaataatc gttatgtgta ttggagtaat					40

<210> SEQ ID NO 182
<211> LENGTH: 40
<212> TYPE: DNA
<213> ORGANISM: Artificial
<220> FEATURE:
<223> OTHER INFORMATION: DNA Aptamer

<400> SEQUENCE: 182
gggggggggc ccggccggca aggccagtgg cgcccgggc					40

<210> SEQ ID NO 183
<211> LENGTH: 40
<212> TYPE: DNA
<213> ORGANISM: Artificial
<220> FEATURE:
<223> OTHER INFORMATION: DNA Aptamer

<400> SEQUENCE: 183
gggggggacc ggggccggcc cggggccccc gcgcccggcc					40

<210> SEQ ID NO 184
<211> LENGTH: 40
<212> TYPE: DNA
<213> ORGANISM: Artificial
<220> FEATURE:
<223> OTHER INFORMATION: DNA Aptamer

<400> SEQUENCE: 184
gaataagaag aatgtcacgc ggccttgggg cctgcgcccg					40

<210> SEQ ID NO 185
<211> LENGTH: 40
<212> TYPE: DNA
<213> ORGANISM: Artificial
<220> FEATURE:
<223> OTHER INFORMATION: DNA Aptamer

<400> SEQUENCE: 185
tagtgggaat taagtgcggg tccgggcacg gcctcgccgc					40

<210> SEQ ID NO 186
<211> LENGTH: 40
<212> TYPE: DNA
<213> ORGANISM: Artificial
<220> FEATURE:
<223> OTHER INFORMATION: DNA Aptamer

<400> SEQUENCE: 186
aacgggtata agcagagatt atgatgagcc ctctctggcc					40

<210> SEQ ID NO 187
<211> LENGTH: 40
<212> TYPE: DNA
<213> ORGANISM: Artificial
<220> FEATURE:
<223> OTHER INFORMATION: DNA Aptamer

<400> SEQUENCE: 187
cgcggagtga gtaaaaattt taagcttata aacccgctta					40

<210> SEQ ID NO 188
<211> LENGTH: 40
<212> TYPE: DNA
<213> ORGANISM: Artificial
<220> FEATURE:
<223> OTHER INFORMATION: DNA Aptamer

<400> SEQUENCE: 188
ggtcttagaa aacagatatt ctagatacta atatagtgtt                              40

<210> SEQ ID NO 189
<211> LENGTH: 40
<212> TYPE: DNA
<213> ORGANISM: Artificial
<220> FEATURE:
<223> OTHER INFORMATION: DNA Aptamer

<400> SEQUENCE: 189
cagtgtatct ttagctgccg cggaatttcc tgagccggat                              40

<210> SEQ ID NO 190
<211> LENGTH: 40
<212> TYPE: DNA
<213> ORGANISM: Artificial
<220> FEATURE:
<223> OTHER INFORMATION: DNA Aptamer

<400> SEQUENCE: 190
ggtctaggtt tattatcaat attagacaca acgggtatat                              40

<210> SEQ ID NO 191
<211> LENGTH: 40
<212> TYPE: DNA
<213> ORGANISM: Artificial
<220> FEATURE:
<223> OTHER INFORMATION: DNA Aptamer

<400> SEQUENCE: 191
tccaagttca aaccttagga acaaatggat gcgcagcgat                              40

<210> SEQ ID NO 192
<211> LENGTH: 40
<212> TYPE: DNA
<213> ORGANISM: Artificial
<220> FEATURE:
<223> OTHER INFORMATION: DNA Aptamer

<400> SEQUENCE: 192 tgattttta ttgatcgtta tttgaagaca tcttccagga                               40

<210> SEQ ID NO 193
<211> LENGTH: 40
<212> TYPE: DNA
<213> ORGANISM: Artificial
<220> FEATURE:
<223> OTHER INFORMATION: DNA Aptamer

<400> SEQUENCE: 193
gacgcttacg cttgttaata agatttttgt tttcattaca                              40

<210> SEQ ID NO 194
<211> LENGTH: 40
<212> TYPE: DNA
<213> ORGANISM: Artificial
<220> FEATURE:
<223> OTHER INFORMATION: DNA Aptamer

<400> SEQUENCE: 194
tctcttttct tgaatcttgc atttaaccca tcccttcaaa        40

<210> SEQ ID NO 195
<211> LENGTH: 40
<212> TYPE: DNA
<213> ORGANISM: Artificial
<220> FEATURE:
<223> OTHER INFORMATION: DNA Aptamer

<400> SEQUENCE: 195
gtgtgaaagc tgggagagtc tgcgggcctg tgtcgcgcaa        40

<210> SEQ ID NO 196
<211> LENGTH: 33
<212> TYPE: DNA
<213> ORGANISM: Artificial
<220> FEATURE:
<223> OTHER INFORMATION: DNA Aptamer

<400> SEQUENCE: 196
cgtaggaggg agattcccac aaacgctccc cat        33

<210> SEQ ID NO 197
<211> LENGTH: 40
<212> TYPE: DNA
<213> ORGANISM: Artificial
<220> FEATURE:
<223> OTHER INFORMATION: DNA Aptamer

<400> SEQUENCE: 197
cgagatcgtt atataaggga caatctgacg attctacctt        40

<210> SEQ ID NO 198
<211> LENGTH: 40
<212> TYPE: DNA
<213> ORGANISM: Artificial
<220> FEATURE:
<223> OTHER INFORMATION: DNA Aptamer

<400> SEQUENCE: 198
atgggtgtgt ctgggtagac gttgttttgg cctggtgtta        40

<210> SEQ ID NO 199
<211> LENGTH: 40
<212> TYPE: DNA
<213> ORGANISM: Artificial
<220> FEATURE:
<223> OTHER INFORMATION: DNA Aptamer

<400> SEQUENCE: 199
tcaattaaga tcttgtgtca agtgttaaag tccgtcatga        40

<210> SEQ ID NO 200
<211> LENGTH: 40
<212> TYPE: DNA
<213> ORGANISM: Artificial
<220> FEATURE:
<223> OTHER INFORMATION: DNA Aptamer

<400> SEQUENCE: 200
aattgttcgg ttgacgcttt tctgacgctg tataccctgg        40

<210> SEQ ID NO 201
<211> LENGTH: 40

```
<212> TYPE: DNA
<213> ORGANISM: Artificial
<220> FEATURE:
<223> OTHER INFORMATION: DNA Aptamer

<400> SEQUENCE: 201
gatgctattt tgatagata catgtaacct tttagacttt                    40

<210> SEQ ID NO 202
<211> LENGTH: 40
<212> TYPE: DNA
<213> ORGANISM: Artificial
<220> FEATURE:
<223> OTHER INFORMATION: DNA Aptamer

<400> SEQUENCE: 202
gatgctattt tgatagata catgtaacct tttagacttt                    40

<210> SEQ ID NO 203
<211> LENGTH: 40
<212> TYPE: DNA
<213> ORGANISM: Artificial
<220> FEATURE:
<223> OTHER INFORMATION: DNA Aptamer

<400> SEQUENCE: 203
agctttttat ggaattattc tcacaacaca ttggaacatt                   40

<210> SEQ ID NO 204
<211> LENGTH: 40
<212> TYPE: DNA
<213> ORGANISM: Artificial
<220> FEATURE:
<223> OTHER INFORMATION: DNA Aptamer

<400> SEQUENCE: 204
tggagtgagt gacttgacta cttacagtaa cctctacagt                   40

<210> SEQ ID NO 205
<211> LENGTH: 40
<212> TYPE: DNA
<213> ORGANISM: Artificial
<220> FEATURE:
<223> OTHER INFORMATION: DNA Aptamer

<400> SEQUENCE: 205
atgtgtcaaa gatttatcga gaaacgctgt ttttattgta                   40

<210> SEQ ID NO 206
<211> LENGTH: 40
<212> TYPE: DNA
<213> ORGANISM: Artificial
<220> FEATURE:
<223> OTHER INFORMATION: DNA Aptamer

<400> SEQUENCE: 206
agatccatta gaatcaattt atttgggcat cgtattccgc                   40

<210> SEQ ID NO 207
<211> LENGTH: 40
<212> TYPE: DNA
<213> ORGANISM: Artificial
<220> FEATURE:
<223> OTHER INFORMATION: DNA Aptamer

<400> SEQUENCE: 207
```
attaacttaa aaacaatcct taatcgttgc aattaaatcc            40

<210> SEQ ID NO 208
<211> LENGTH: 40
<212> TYPE: DNA
<213> ORGANISM: Artificial
<220> FEATURE:
<223> OTHER INFORMATION: DNA Aptamer

<400> SEQUENCE: 208
cttcgttaaa tctgtatgta cccgtagcta gcttaatttc            40

<210> SEQ ID NO 209
<211> LENGTH: 39
<212> TYPE: DNA
<213> ORGANISM: Artificial
<220> FEATURE:
<223> OTHER INFORMATION: DNA Aptamer

<400> SEQUENCE: 209
cttttatctt cttatattgt ccaaggtcgt atgcaagcg            39

<210> SEQ ID NO 210
<211> LENGTH: 40
<212> TYPE: DNA
<213> ORGANISM: Artificial
<220> FEATURE:
<223> OTHER INFORMATION: DNA Aptamer

<400> SEQUENCE: 210
gattaatcag tattcccgtt cgtttctggc aacatttaca            40

<210> SEQ ID NO 211
<211> LENGTH: 39
<212> TYPE: DNA
<213> ORGANISM: Artificial
<220> FEATURE:
<223> OTHER INFORMATION: DNA Aptamer

<400> SEQUENCE: 211
taggaatcgg attatgaaat tgtggcccag gtatcgtca            39

<210> SEQ ID NO 212
<211> LENGTH: 38
<212> TYPE: DNA
<213> ORGANISM: Artificial
<220> FEATURE:
<223> OTHER INFORMATION: DNA Aptamer

<400> SEQUENCE: 212
tgattttttg agggttaact aatttatatc tgtgtttt            38

<210> SEQ ID NO 213
<211> LENGTH: 39
<212> TYPE: DNA
<213> ORGANISM: Artificial
<220> FEATURE:
<223> OTHER INFORMATION: DNA Aptamer

<400> SEQUENCE: 213
agggtcgttg gggccagggt tcacgcgccg ctccccgct            39

<210> SEQ ID NO 214
<211> LENGTH: 39
<212> TYPE: DNA
<213> ORGANISM: Artificial

```
<220> FEATURE:
<223> OTHER INFORMATION: DNA Aptamer

<400> SEQUENCE: 214
gctgattcgt tcagatctct attctcctta ttatcgaca                              39

<210> SEQ ID NO 215
<211> LENGTH: 40
<212> TYPE: DNA
<213> ORGANISM: Artificial
<220> FEATURE:
<223> OTHER INFORMATION: DNA Aptamer

<400> SEQUENCE: 215
gtgataggga agtgagtgct ggcccgtagc gaccctggaa                             40

<210> SEQ ID NO 216
<211> LENGTH: 40
<212> TYPE: DNA
<213> ORGANISM: Artificial
<220> FEATURE:
<223> OTHER INFORMATION: DNA Aptamer

<400> SEQUENCE: 216
caggagcgta ataatctcga gaacgtgtgg caaacgatac                             40

<210> SEQ ID NO 217
<211> LENGTH: 35
<212> TYPE: DNA
<213> ORGANISM: Artificial
<220> FEATURE:
<223> OTHER INFORMATION: DNA Aptamer

<400> SEQUENCE: 217
aatggtgatg attctcgtta ttcgttcagc ctcta                                  35

<210> SEQ ID NO 218
<211> LENGTH: 39
<212> TYPE: DNA
<213> ORGANISM: Artificial
<220> FEATURE:
<223> OTHER INFORMATION: DNA Aptamer

<400> SEQUENCE: 218
cggctgtccc ggccaggggg cggggcgcgg tgcgctaat                              39

<210> SEQ ID NO 219
<211> LENGTH: 39
<212> TYPE: DNA
<213> ORGANISM: Artificial
<220> FEATURE:
<223> OTHER INFORMATION: DNA Aptamer

<400> SEQUENCE: 219
gcgggcgcgc agcgccacgg gaccggcccg ccgggggc                               39

<210> SEQ ID NO 220
<211> LENGTH: 40
<212> TYPE: DNA
<213> ORGANISM: Artificial
<220> FEATURE:
<223> OTHER INFORMATION: DNA Aptamer

<400> SEQUENCE: 220
ccaatgtggt gaataggaat gtttcaccgc ttaggataaa                             40
```

<210> SEQ ID NO 221
<211> LENGTH: 40
<212> TYPE: DNA
<213> ORGANISM: Artificial
<220> FEATURE:
<223> OTHER INFORMATION: DNA Aptamer

<400> SEQUENCE: 221
cggggaaatt agggagggta tcttcgttgg tcctccggcc                              40

<210> SEQ ID NO 222
<211> LENGTH: 40
<212> TYPE: DNA
<213> ORGANISM: Artificial
<220> FEATURE:
<223> OTHER INFORMATION: DNA Aptamer

<400> SEQUENCE: 222
gttcgtcaaa aatagagtgt tttatgacac aggaatccga                              40

<210> SEQ ID NO 223
<211> LENGTH: 39
<212> TYPE: DNA
<213> ORGANISM: Artificial
<220> FEATURE:
<223> OTHER INFORMATION: DNA Aptamer

<400> SEQUENCE: 223
gaaaatggta tattcgagtt ctgtggcata tggggccat                               39

<210> SEQ ID NO 224
<211> LENGTH: 40
<212> TYPE: DNA
<213> ORGANISM: Artificial
<220> FEATURE:
<223> OTHER INFORMATION: DNA Aptamer

<400> SEQUENCE: 224
gtttgtttct ttacggcatg ggtcatctat cccaattacc                              40

<210> SEQ ID NO 225
<211> LENGTH: 40
<212> TYPE: DNA
<213> ORGANISM: Artificial
<220> FEATURE:
<223> OTHER INFORMATION: DNA Aptamer

<400> SEQUENCE: 225
ctacaaaatt gacaaatcta cttttgtgta ttcaagttat                              40

<210> SEQ ID NO 226
<211> LENGTH: 40
<212> TYPE: DNA
<213> ORGANISM: Artificial
<220> FEATURE:
<223> OTHER INFORMATION: DNA Aptamer

<400> SEQUENCE: 226
gaaggactga aagaggacgg agcgtagcgg cgtacagaac                              40

<210> SEQ ID NO 227
<211> LENGTH: 40
<212> TYPE: DNA
<213> ORGANISM: Artificial
<220> FEATURE:
<223> OTHER INFORMATION: DNA Aptamer

<400> SEQUENCE: 227
atgtgtaatt tttttaccaa agccaaagca ttttccaatg                    40

<210> SEQ ID NO 228
<211> LENGTH: 40
<212> TYPE: DNA
<213> ORGANISM: Artificial
<220> FEATURE:
<223> OTHER INFORMATION: DNA Aptamer

<400> SEQUENCE: 228
aggattgtaa tattgatatc ctgattcgtt taatttgagc                    40

<210> SEQ ID NO 229
<211> LENGTH: 40
<212> TYPE: DNA
<213> ORGANISM: Artificial
<220> FEATURE:
<223> OTHER INFORMATION: DNA Aptamer

<400> SEQUENCE: 229
tcccgtatag ttactattct tttattactg aataagcgaa                    40

<210> SEQ ID NO 230
<211> LENGTH: 40
<212> TYPE: DNA
<213> ORGANISM: Artificial
<220> FEATURE:
<223> OTHER INFORMATION: DNA Aptamer

<400> SEQUENCE: 230
ctgttctatc ttttcaagaa tgtcccatca gtcaatgccg                    40

<210> SEQ ID NO 231
<211> LENGTH: 40
<212> TYPE: DNA
<213> ORGANISM: Artificial
<220> FEATURE:
<223> OTHER INFORMATION: DNA Aptamer

<400> SEQUENCE: 231
tcgtctgtgt ctcaaaagtg tatctagtga tgccccagat                    40

<210> SEQ ID NO 232
<211> LENGTH: 39
<212> TYPE: DNA
<213> ORGANISM: Artificial
<220> FEATURE:
<223> OTHER INFORMATION: DNA Aptamer

<400> SEQUENCE: 232
gataatttat ggttaacgag ttcttcagtt gagggattt                     39

<210> SEQ ID NO 233
<211> LENGTH: 40
<212> TYPE: DNA
<213> ORGANISM: Artificial
<220> FEATURE:
<223> OTHER INFORMATION: DNA Aptamer

<400> SEQUENCE: 233
tgttctattt aatgatttgt caacacgatc ggatctactg                    40

<210> SEQ ID NO 234

```
<210> SEQ ID NO 234
<211> LENGTH: 38
<212> TYPE: DNA
<213> ORGANISM: Artificial
<220> FEATURE:
<223> OTHER INFORMATION: DNA Aptamer

<400> SEQUENCE: 234
ttctgattgg gtcttttgat gttttatgaa atcatgca                              38

<210> SEQ ID NO 235
<211> LENGTH: 39
<212> TYPE: DNA
<213> ORGANISM: Artificial
<220> FEATURE:
<223> OTHER INFORMATION: DNA Aptamer

<400> SEQUENCE: 235
gagtttttta aaagaacagt ttcatctcct cagtcttac                             39

<210> SEQ ID NO 236
<211> LENGTH: 40
<212> TYPE: DNA
<213> ORGANISM: Artificial
<220> FEATURE:
<223> OTHER INFORMATION: DNA Aptamer

<400> SEQUENCE: 236
gttcatattt aatctactgt attcctatta tatgtttagg                            40

<210> SEQ ID NO 237
<211> LENGTH: 29
<212> TYPE: DNA
<213> ORGANISM: Artificial
<220> FEATURE:
<223> OTHER INFORMATION: DNA Aptamer

<400> SEQUENCE: 237
atctggatat aattaagtgg gtcaacaga                                        29

<210> SEQ ID NO 238
<211> LENGTH: 39
<212> TYPE: DNA
<213> ORGANISM: Artificial
<220> FEATURE:
<223> OTHER INFORMATION: DNA Aptamer

<400> SEQUENCE: 238
attttcaagt attaacatta ttagatagtt tcaagagcc                             39

<210> SEQ ID NO 239
<211> LENGTH: 40
<212> TYPE: DNA
<213> ORGANISM: Artificial
<220> FEATURE:
<223> OTHER INFORMATION: DNA Aptamer

<400> SEQUENCE: 239
gatattttga aatgattatc ctagacatct gattagctat                            40

<210> SEQ ID NO 240
<211> LENGTH: 36
<212> TYPE: DNA
<213> ORGANISM: Artificial
<220> FEATURE:
<223> OTHER INFORMATION: DNA Aptamer

<400> SEQUENCE: 240
```

```
ggaaaggaga aaagagggga gcagtgagtc gtatta                                36
```

<210> SEQ ID NO 241
<211> LENGTH: 40
<212> TYPE: DNA
<213> ORGANISM: Artificial
<220> FEATURE:
<223> OTHER INFORMATION: DNA Aptamer

<400> SEQUENCE: 241

```
atatagcgca accgaggggt aggacgtgca ccccagagcc                            40
```

<210> SEQ ID NO 242
<211> LENGTH: 40
<212> TYPE: DNA
<213> ORGANISM: Artificial
<220> FEATURE:
<223> OTHER INFORMATION: DNA Aptamer

<400> SEQUENCE: 242

```
gggggatatt caagtctccc ctcattgtat ccctaccctt                            40
```

<210> SEQ ID NO 243
<211> LENGTH: 40
<212> TYPE: DNA
<213> ORGANISM: Artificial
<220> FEATURE:
<223> OTHER INFORMATION: DNA Aptamer

<400> SEQUENCE: 243

```
ataaacatga aggggtggcg ctgggcagtc ataattgaac                            40
```

<210> SEQ ID NO 244
<211> LENGTH: 40
<212> TYPE: DNA
<213> ORGANISM: Artificial
<220> FEATURE:
<223> OTHER INFORMATION: DNA Aptamer

<400> SEQUENCE: 244

```
ttccagcgag gtggtgctta atgagtcccg aaaatgttct                            40
```

<210> SEQ ID NO 245
<211> LENGTH: 40
<212> TYPE: DNA
<213> ORGANISM: Artificial
<220> FEATURE:
<223> OTHER INFORMATION: DNA Aptamer

<400> SEQUENCE: 245

```
gtcgggagta gagtggaagc gaggaagggg gcaaaacaca                            40
```

<210> SEQ ID NO 246
<211> LENGTH: 44
<212> TYPE: DNA
<213> ORGANISM: Artificial
<220> FEATURE:
<223> OTHER INFORMATION: DNA Aptamer

<400> SEQUENCE: 246

```
ccgatgtagg agtgaggcct aggttgactg cgagacgcta accc                       44
```

<210> SEQ ID NO 247
<211> LENGTH: 40
<212> TYPE: DNA

```
<213> ORGANISM: Artificial
<220> FEATURE:
<223> OTHER INFORMATION: DNA Aptamer

<400> SEQUENCE: 247
catgacaact aggtttcaaa aggtctttag ataaagtccc                          40

<210> SEQ ID NO 248
<211> LENGTH: 40
<212> TYPE: DNA
<213> ORGANISM: Artificial
<220> FEATURE:
<223> OTHER INFORMATION: DNA Aptamer

<400> SEQUENCE: 248
ccgcgggctt ccagtatctc tgggtacact actggtcagt                          40

<210> SEQ ID NO 249
<211> LENGTH: 40
<212> TYPE: DNA
<213> ORGANISM: Artificial
<220> FEATURE:
<223> OTHER INFORMATION: DNA Aptamer

<400> SEQUENCE: 249
gcgaggatgt ccaaatgcat ggaaagtaac agctccaagc                          40

<210> SEQ ID NO 250
<211> LENGTH: 44
<212> TYPE: DNA
<213> ORGANISM: Artificial
<220> FEATURE:
<223> OTHER INFORMATION: DNA Aptamer

<400> SEQUENCE: 250
ccgatgtagg agtgagaacg acaaacaatc cttgagctgc aatc                     44

<210> SEQ ID NO 251
<211> LENGTH: 46
<212> TYPE: DNA
<213> ORGANISM: Artificial
<220> FEATURE:
<223> OTHER INFORMATION: DNA Aptamer

<400> SEQUENCE: 251
ccgatgtagg agtgaggaca catgtgaaaa gacataattt attggg                   46

<210> SEQ ID NO 252
<211> LENGTH: 42
<212> TYPE: DNA
<213> ORGANISM: Artificial
<220> FEATURE:
<223> OTHER INFORMATION: DNA Aptamer

<400> SEQUENCE: 252
ccgatgtagg agtgagacaa cctgtcattg acttcttagc ta                       42

<210> SEQ ID NO 253
<211> LENGTH: 40
<212> TYPE: DNA
<213> ORGANISM: Artificial
<220> FEATURE:
<223> OTHER INFORMATION: DNA Aptamer

<400> SEQUENCE: 253
accatctcta ttgttggcac aaatttggcc tgctacattc                          40
```

<210> SEQ ID NO 254
<211> LENGTH: 48
<212> TYPE: DNA
<213> ORGANISM: Artificial
<220> FEATURE:
<223> OTHER INFORMATION: DNA Aptamer

<400> SEQUENCE: 254
ccgatgtagg agtgagaaga cgggcattgg ataccagc ttattcaa 48

<210> SEQ ID NO 255
<211> LENGTH: 50
<212> TYPE: DNA
<213> ORGANISM: Artificial
<220> FEATURE:
<223> OTHER INFORMATION: DNA Aptamer

<400> SEQUENCE: 255
ccgatgtagg agtgagaaaa acaatcgacc ctatatacca gcttattcaa 50

<210> SEQ ID NO 256
<211> LENGTH: 41
<212> TYPE: DNA
<213> ORGANISM: Artificial
<220> FEATURE:
<223> OTHER INFORMATION: DNA Aptamer

<400> SEQUENCE: 256
ccgatgtagg agtgagatgc gtgttatacc agcttattca a 41

<210> SEQ ID NO 257
<211> LENGTH: 40
<212> TYPE: DNA
<213> ORGANISM: Artificial
<220> FEATURE:
<223> OTHER INFORMATION: DNA Aptamer

<400> SEQUENCE: 257
gccgtcttcg atgtgtatct gctatgttaa ggggacgagg 40

<210> SEQ ID NO 258
<211> LENGTH: 43
<212> TYPE: DNA
<213> ORGANISM: Artificial
<220> FEATURE:
<223> OTHER INFORMATION: DNA Aptamer

<400> SEQUENCE: 258
ccgatgtagg agtgagacta accccgtata ccagcttatt caa 43

<210> SEQ ID NO 259
<211> LENGTH: 40
<212> TYPE: DNA
<213> ORGANISM: Artificial
<220> FEATURE:
<223> OTHER INFORMATION: DNA Aptamer

<400> SEQUENCE: 259
gtaagtcaaa cagtcatcta tcattcttat gtccactttt 40

<210> SEQ ID NO 260
<211> LENGTH: 40
<212> TYPE: DNA
<213> ORGANISM: Artificial
<220> FEATURE:

<223> OTHER INFORMATION: DNA Aptamer

<400> SEQUENCE: 260
gcctctttga cgtgatgttc gctcttatga ccacattcat        40

<210> SEQ ID NO 261
<211> LENGTH: 40
<212> TYPE: DNA
<213> ORGANISM: Artificial
<220> FEATURE:
<223> OTHER INFORMATION: DNA Aptamer

<400> SEQUENCE: 261
ttttcattgc tacaaagtca ttttgtaggt aacggtggat        40

<210> SEQ ID NO 262
<211> LENGTH: 40
<212> TYPE: DNA
<213> ORGANISM: Artificial
<220> FEATURE:
<223> OTHER INFORMATION: DNA Aptamer

<400> SEQUENCE: 262
atctcgggtg gcccttctag tgggagcatc tccactgaaa        40

<210> SEQ ID NO 263
<211> LENGTH: 40
<212> TYPE: DNA
<213> ORGANISM: Artificial
<220> FEATURE:
<223> OTHER INFORMATION: DNA Aptamer

<400> SEQUENCE: 263
tttcgcgtat atcacgtcgt attcaggagt aacattctaa        40

<210> SEQ ID NO 264
<211> LENGTH: 40
<212> TYPE: DNA
<213> ORGANISM: Artificial
<220> FEATURE:
<223> OTHER INFORMATION: DNA Aptamer

<400> SEQUENCE: 264
cacaatcaat gtaacattgc caatagtaaa ttgaaatcct        40

<210> SEQ ID NO 265
<211> LENGTH: 48
<212> TYPE: DNA
<213> ORGANISM: Artificial
<220> FEATURE:
<223> OTHER INFORMATION: DNA Aptamer

<400> SEQUENCE: 265
ccgatgtagg agtgaggtgc attcccggct cgtataccag cttattca        48

<210> SEQ ID NO 266
<211> LENGTH: 42
<212> TYPE: DNA
<213> ORGANISM: Artificial
<220> FEATURE:
<223> OTHER INFORMATION: DNA Aptamer

<400> SEQUENCE: 266
ccgatgtagg agtgagcgcc gaaaactgcg aaagcgacac cg        42

```
<210> SEQ ID NO 267
<211> LENGTH: 48
<212> TYPE: DNA
<213> ORGANISM: Artificial
<220> FEATURE:
<223> OTHER INFORMATION: DNA Aptamer

<400> SEQUENCE: 267
ccaatgtagg agtgagagaa agcgcggctg atataccagc ttattcaa                    48

<210> SEQ ID NO 268
<211> LENGTH: 39
<212> TYPE: DNA
<213> ORGANISM: Artificial
<220> FEATURE:
<223> OTHER INFORMATION: DNA Aptamer

<400> SEQUENCE: 268
ccgatgtagg agtgagggac gcctatacca gcttattca                              39

<210> SEQ ID NO 269
<211> LENGTH: 40
<212> TYPE: DNA
<213> ORGANISM: Artificial
<220> FEATURE:
<223> OTHER INFORMATION: DNA Aptamer

<400> SEQUENCE: 269
cacccaatgg ggtaagagtt ggaatttact aaccaccgga                             40

<210> SEQ ID NO 270
<211> LENGTH: 43
<212> TYPE: DNA
<213> ORGANISM: Artificial
<220> FEATURE:
<223> OTHER INFORMATION: DNA Aptamer

<400> SEQUENCE: 270
ccgatgtagg agtgagggtg caatggtact gcccttccct tgg                         43

<210> SEQ ID NO 271
<211> LENGTH: 40
<212> TYPE: DNA
<213> ORGANISM: Artificial
<220> FEATURE:
<223> OTHER INFORMATION: DNA Aptamer

<400> SEQUENCE: 271
aacggaaaag tcatacgcgc ttacgatatc ggttgtcgta                             40

<210> SEQ ID NO 272
<211> LENGTH: 40
<212> TYPE: DNA
<213> ORGANISM: Artificial
<220> FEATURE:
<223> OTHER INFORMATION: DNA Aptamer

<400> SEQUENCE: 272
tccgcgaatc ttataacggt tcttccctaa tgtacatagg                             40

<210> SEQ ID NO 273
<211> LENGTH: 40
<212> TYPE: DNA
<213> ORGANISM: Artificial
<220> FEATURE:
<223> OTHER INFORMATION: DNA Aptamer
<220> FEATURE:
```

```
<221> NAME/KEY: misc_feature
<222> LOCATION: (17)..(17)
<223> OTHER INFORMATION: n is a, c, g, or t

<400> SEQUENCE: 273
ctcatttaat ataaatngga ttaggtgaaa agtttcgcta                    40

<210> SEQ ID NO 274
<211> LENGTH: 40
<212> TYPE: DNA
<213> ORGANISM: Artificial
<220> FEATURE:
<223> OTHER INFORMATION: DNA Aptamer

<400> SEQUENCE: 274
atccaccaaa acggagttgc tcgtaattta ttcatcaact                    40

<210> SEQ ID NO 275
<211> LENGTH: 37
<212> TYPE: DNA
<213> ORGANISM: Artificial
<220> FEATURE:
<223> OTHER INFORMATION: DNA Aptamer

<400> SEQUENCE: 275
ccgatgtagg agtgatacgc tgtgtgtggc accaaca                       37

<210> SEQ ID NO 276
<211> LENGTH: 40
<212> TYPE: DNA
<213> ORGANISM: Artificial
<220> FEATURE:
<223> OTHER INFORMATION: DNA Aptamer

<400> SEQUENCE: 276
actgaggtct gtccgtttac tatgtgaagg tccaataatc                    40

<210> SEQ ID NO 277
<211> LENGTH: 43
<212> TYPE: DNA
<213> ORGANISM: Artificial
<220> FEATURE:
<223> OTHER INFORMATION: DNA Aptamer

<400> SEQUENCE: 277
ccgatgtagg agtgaggcta accccgtata ccagcttatt caa                43

<210> SEQ ID NO 278
<211> LENGTH: 40
<212> TYPE: DNA
<213> ORGANISM: Artificial
<220> FEATURE:
<223> OTHER INFORMATION: DNA Aptamer

<400> SEQUENCE: 278
tgtgtagaga atcccgagtt tgcacgatgt tccctagcgc                    40

<210> SEQ ID NO 279
<211> LENGTH: 52
<212> TYPE: DNA
<213> ORGANISM: Artificial
<220> FEATURE:
<223> OTHER INFORMATION: DNA Aptamer

<400> SEQUENCE: 279
ccgatgtagg agtgagggga catataacct atacctatac cagcttattc aa      52
```

```
<210> SEQ ID NO 280
<211> LENGTH: 44
<212> TYPE: DNA
<213> ORGANISM: Artificial
<220> FEATURE:
<223> OTHER INFORMATION: DNA Aptamer

<400> SEQUENCE: 280
ccgatgtagg agtgagggtt gaattggtta tcgagacatt ggcg            44

<210> SEQ ID NO 281
<211> LENGTH: 40
<212> TYPE: DNA
<213> ORGANISM: Artificial
<220> FEATURE:
<223> OTHER INFORMATION: DNA Aptamer

<400> SEQUENCE: 281
ccacagttcc aatgttcttt atactcgcgt tgaatctaag                 40

<210> SEQ ID NO 282
<211> LENGTH: 41
<212> TYPE: DNA
<213> ORGANISM: Artificial
<220> FEATURE:
<223> OTHER INFORMATION: DNA Aptamer

<400> SEQUENCE: 282
cgtaggacac cctcaagaaa aagggtattg acccgggata t               41

<210> SEQ ID NO 283
<211> LENGTH: 40
<212> TYPE: DNA
<213> ORGANISM: Artificial
<220> FEATURE:
<223> OTHER INFORMATION: DNA Aptamer

<400> SEQUENCE: 283
cccgtaattc gctaattgct agataactag aatcgactca                 40

<210> SEQ ID NO 284
<211> LENGTH: 40
<212> TYPE: DNA
<213> ORGANISM: Artificial
<220> FEATURE:
<223> OTHER INFORMATION: DNA Aptamer

<400> SEQUENCE: 284
gtgaacggat atctttattc ggcatcttag gtagtcttaa                 40

<210> SEQ ID NO 285
<211> LENGTH: 40
<212> TYPE: DNA
<213> ORGANISM: Artificial
<220> FEATURE:
<223> OTHER INFORMATION: DNA Aptamer

<400> SEQUENCE: 285
ttcattcatt agcagaccca actgtaattc agcctgtatg                 40

<210> SEQ ID NO 286
<211> LENGTH: 41
<212> TYPE: DNA
<213> ORGANISM: Artificial
<220> FEATURE:
```

<223> OTHER INFORMATION: DNA Aptamer

<400> SEQUENCE: 286
ccgatgtagg agtaagaccg cgtgtatacc agcttattca a                    41

<210> SEQ ID NO 287
<211> LENGTH: 40
<212> TYPE: DNA
<213> ORGANISM: Artificial
<220> FEATURE:
<223> OTHER INFORMATION: DNA Aptamer

<400> SEQUENCE: 287
tttgctatga cataaaagga ttttcgaaca ggaggcccaa                      40

<210> SEQ ID NO 288
<211> LENGTH: 40
<212> TYPE: DNA
<213> ORGANISM: Artificial
<220> FEATURE:
<223> OTHER INFORMATION: DNA Aptamer

<400> SEQUENCE: 288
ccacttgtaa tttcgataca ttgcgtactt tctgcaggca                      40

<210> SEQ ID NO 289
<211> LENGTH: 39
<212> TYPE: DNA
<213> ORGANISM: Artificial
<220> FEATURE:
<223> OTHER INFORMATION: DNA Aptamer

<400> SEQUENCE: 289
ctgaagtggc cttaacctca gtggcaattt gtaaaagta                       39

<210> SEQ ID NO 290
<211> LENGTH: 40
<212> TYPE: DNA
<213> ORGANISM: Artificial
<220> FEATURE:
<223> OTHER INFORMATION: DNA Aptamer

<400> SEQUENCE: 290
ttgctcgcta aatttgttta tgcctctttt tgccagtata                      40

<210> SEQ ID NO 291
<211> LENGTH: 40
<212> TYPE: DNA
<213> ORGANISM: Artificial
<220> FEATURE:
<223> OTHER INFORMATION: DNA Aptamer

<400> SEQUENCE: 291
ctcgatccgg ataaaaagca tcttccactc tttctactaa                      40

<210> SEQ ID NO 292
<211> LENGTH: 40
<212> TYPE: DNA
<213> ORGANISM: Artificial
<220> FEATURE:
<223> OTHER INFORMATION: DNA Aptamer

<400> SEQUENCE: 292
gattataatt attaattatt gtcacggtaa gtccaaagtc                      40

```
<210> SEQ ID NO 293
<211> LENGTH: 40
<212> TYPE: DNA
<213> ORGANISM: Artificial
<220> FEATURE:
<223> OTHER INFORMATION: DNA Aptamer

<400> SEQUENCE: 293
tcgcatttag ataattgtca ttttacgact tcataccttta                          40

<210> SEQ ID NO 294
<211> LENGTH: 40
<212> TYPE: DNA
<213> ORGANISM: Artificial
<220> FEATURE:
<223> OTHER INFORMATION: DNA Aptamer

<400> SEQUENCE: 294
ggatgtttaa cggttgtcta tatccctctt acaccaatca                           40

<210> SEQ ID NO 295
<211> LENGTH: 29
<212> TYPE: DNA
<213> ORGANISM: Artificial
<220> FEATURE:
<223> OTHER INFORMATION: DNA Aptamer

<400> SEQUENCE: 295
cttgattttt aatgactcag taaaatgtc                                       29

<210> SEQ ID NO 296
<211> LENGTH: 40
<212> TYPE: DNA
<213> ORGANISM: Artificial
<220> FEATURE:
<223> OTHER INFORMATION: DNA Aptamer

<400> SEQUENCE: 296
cggtttatgg tcgtaaaaac tttacgctta cccttctttt                           40

<210> SEQ ID NO 297
<211> LENGTH: 40
<212> TYPE: DNA
<213> ORGANISM: Artificial
<220> FEATURE:
<223> OTHER INFORMATION: DNA Aptamer

<400> SEQUENCE: 297
gtgttttgaa tttattaaat tggaaactac ccgtgcactt                           40

<210> SEQ ID NO 298
<211> LENGTH: 35
<212> TYPE: DNA
<213> ORGANISM: Artificial
<220> FEATURE:
<223> OTHER INFORMATION: DNA Aptamer

<400> SEQUENCE: 298
cgtaagaggg agattcctac aaacgctccc catcc                                35

<210> SEQ ID NO 299
<211> LENGTH: 39
<212> TYPE: DNA
<213> ORGANISM: Artificial
<220> FEATURE:
<223> OTHER INFORMATION: DNA Aptamer
```

-continued

<400> SEQUENCE: 299 ggtcttttttt tttttgaata cttgggtcga gtttcgcca                              39

<210> SEQ ID NO 300
<211> LENGTH: 40
<212> TYPE: DNA
<213> ORGANISM: Artificial
<220> FEATURE:
<223> OTHER INFORMATION: DNA Aptamer

<400> SEQUENCE: 300
cgatttttat tgtaatccat tggtcaccaa cggttcaaga                              40

<210> SEQ ID NO 301
<211> LENGTH: 40
<212> TYPE: DNA
<213> ORGANISM: Artificial
<220> FEATURE:
<223> OTHER INFORMATION: DNA Aptamer

<400> SEQUENCE: 301
aaggttttta accctctcga aaagtatca tcctcaatcc                               40

<210> SEQ ID NO 302
<211> LENGTH: 38
<212> TYPE: DNA
<213> ORGANISM: Artificial
<220> FEATURE:
<223> OTHER INFORMATION: DNA Aptamer

<400> SEQUENCE: 302
gcgttaaatg aataattctt tttaatttct tttacttg                                38

<210> SEQ ID NO 303
<211> LENGTH: 38
<212> TYPE: DNA
<213> ORGANISM: Artificial
<220> FEATURE:
<223> OTHER INFORMATION: DNA Aptamer

<400> SEQUENCE: 303
gcggaatgat ttgttttaat acgtcgacag cattgcaa                                38

<210> SEQ ID NO 304
<211> LENGTH: 40
<212> TYPE: DNA
<213> ORGANISM: Artificial
<220> FEATURE:
<223> OTHER INFORMATION: DNA Aptamer

<400> SEQUENCE: 304
gaattttttt cttaaaagct aatttccctt cgctcacatc                              40

<210> SEQ ID NO 305
<211> LENGTH: 38
<212> TYPE: DNA
<213> ORGANISM: Artificial
<220> FEATURE:
<223> OTHER INFORMATION: DNA Aptamer

<400> SEQUENCE: 305
cgattttttg gaataagtca ctgtgaatgg aaacatat                                38

<210> SEQ ID NO 306
<211> LENGTH: 38

```
<212> TYPE: DNA
<213> ORGANISM: Artificial
<220> FEATURE:
<223> OTHER INFORMATION: DNA Aptamer

<400> SEQUENCE: 306
tgttaagata attaagtgtc accgtctata ctaaattt                              38

<210> SEQ ID NO 307
<211> LENGTH: 38
<212> TYPE: DNA
<213> ORGANISM: Artificial
<220> FEATURE:
<223> OTHER INFORMATION: DNA Aptamer

<400> SEQUENCE: 307
tagttgttta tttattctca tgtttcggag cgttaact                              38

<210> SEQ ID NO 308
<211> LENGTH: 39
<212> TYPE: DNA
<213> ORGANISM: Artificial
<220> FEATURE:
<223> OTHER INFORMATION: DNA Aptamer

<400> SEQUENCE: 308
caaagatttg atagttaacg gttattgatt ttcactctc                             39

<210> SEQ ID NO 309
<211> LENGTH: 38
<212> TYPE: DNA
<213> ORGANISM: Artificial
<220> FEATURE:
<223> OTHER INFORMATION: DNA Aptamer

<400> SEQUENCE: 309
aatttttcga gttatgaata tttcgcctct tactcttt                              38

<210> SEQ ID NO 310
<211> LENGTH: 40
<212> TYPE: DNA
<213> ORGANISM: Artificial
<220> FEATURE:
<223> OTHER INFORMATION: DNA Aptamer

<400> SEQUENCE: 310
gtattttttt ggttgtaaaa aaaagtatca cactaatttg                            40

<210> SEQ ID NO 311
<211> LENGTH: 26
<212> TYPE: DNA
<213> ORGANISM: Artificial
<220> FEATURE:
<223> OTHER INFORMATION: DNA Aptamer

<400> SEQUENCE: 311
ggaaagggga aaggggggga gcggtg                                           26

<210> SEQ ID NO 312
<211> LENGTH: 38
<212> TYPE: DNA
<213> ORGANISM: Artificial
<220> FEATURE:
<223> OTHER INFORMATION: DNA Aptamer

<400> SEQUENCE: 312
```
cgtaggaggg agttccaatg atacatccta accgatac					38

<210> SEQ ID NO 313
<211> LENGTH: 40
<212> TYPE: DNA
<213> ORGANISM: Artificial
<220> FEATURE:
<223> OTHER INFORMATION: DNA Aptamer

<400> SEQUENCE: 313
gttctttttt ttacactaac ggtttagtaa actcttcgcc					40

<210> SEQ ID NO 314
<211> LENGTH: 40
<212> TYPE: DNA
<213> ORGANISM: Artificial
<220> FEATURE:
<223> OTHER INFORMATION: DNA Aptamer

<400> SEQUENCE: 314
gttctttttt ttacactaac ggtttagtaa actcttcgcc					40

<210> SEQ ID NO 315
<211> LENGTH: 39
<212> TYPE: DNA
<213> ORGANISM: Artificial
<220> FEATURE:
<223> OTHER INFORMATION: DNA Aptamer

<400> SEQUENCE: 315
aataattatg ttcagcgata cttctatttc caactagcg					39

<210> SEQ ID NO 316
<211> LENGTH: 40
<212> TYPE: DNA
<213> ORGANISM: Artificial
<220> FEATURE:
<223> OTHER INFORMATION: DNA Aptamer

<400> SEQUENCE: 316
cagttttatg ttggtttaat cctggggcat agcgcgtttt					40

<210> SEQ ID NO 317
<211> LENGTH: 25
<212> TYPE: DNA
<213> ORGANISM: Artificial
<220> FEATURE:
<223> OTHER INFORMATION: DNA Aptamer

<400> SEQUENCE: 317
gttatttctt aaaatataat acttc					25

<210> SEQ ID NO 318
<211> LENGTH: 40
<212> TYPE: DNA
<213> ORGANISM: Artificial
<220> FEATURE:
<223> OTHER INFORMATION: DNA Aptamer

<400> SEQUENCE: 318
cgcttaaaat ttctctgttt tctggtagta gcgcaataag					40

<210> SEQ ID NO 319
<211> LENGTH: 40
<212> TYPE: DNA
<213> ORGANISM: Artificial

```
<220> FEATURE:
<223> OTHER INFORMATION: DNA Aptamer

<400> SEQUENCE: 319
gttctttatt aagatgtatt ctataagtat ttcaagttaa                              40

<210> SEQ ID NO 320
<211> LENGTH: 40
<212> TYPE: DNA
<213> ORGANISM: Artificial
<220> FEATURE:
<223> OTHER INFORMATION: DNA Aptamer

<400> SEQUENCE: 320
caaaagattt tagtaacatc tagatggcac gtgatatttc                              40

<210> SEQ ID NO 321
<211> LENGTH: 39
<212> TYPE: DNA
<213> ORGANISM: Artificial
<220> FEATURE:
<223> OTHER INFORMATION: DNA Aptamer

<400> SEQUENCE: 321 tcctttcaa tatttcttca actgaacctt cgtcattca                                39

<210> SEQ ID NO 322
<211> LENGTH: 40
<212> TYPE: DNA
<213> ORGANISM: Artificial
<220> FEATURE:
<223> OTHER INFORMATION: DNA Aptamer

<400> SEQUENCE: 322
ggaatatttt atggcactta ttaaacaatt ggtcaaagtc                              40

<210> SEQ ID NO 323
<211> LENGTH: 40
<212> TYPE: DNA
<213> ORGANISM: Artificial
<220> FEATURE:
<223> OTHER INFORMATION: DNA Aptamer

<400> SEQUENCE: 323
ggtcttcttt gagtattcct agttctttgg ggcattagta                              40

<210> SEQ ID NO 324
<211> LENGTH: 41
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 324
ngagtttnng tttttagaca tttttaccta actagcacgt a                            41

<210> SEQ ID NO 325
<211> LENGTH: 40
<212> TYPE: DNA
```

```
<213> ORGANISM: Artificial
<220> FEATURE:
<223> OTHER INFORMATION: DNA Aptamer

<400> SEQUENCE: 325
ccatgttatt ttaatcctat tttcagtacg actattacct                            40

<210> SEQ ID NO 326
<211> LENGTH: 40
<212> TYPE: DNA
<213> ORGANISM: Artificial
<220> FEATURE:
<223> OTHER INFORMATION: DNA Aptamer

<400> SEQUENCE: 326
gttagtaacg gtcagtttaa ttaagaacat ttgctacgac                            40

<210> SEQ ID NO 327
<211> LENGTH: 40
<212> TYPE: DNA
<213> ORGANISM: Artificial
<220> FEATURE:
<223> OTHER INFORMATION: DNA Aptamer

<400> SEQUENCE: 327
ctaatgatgg ttttcgcaat taacgccatc gaacaagatc                            40

<210> SEQ ID NO 328
<211> LENGTH: 40
<212> TYPE: DNA
<213> ORGANISM: Artificial
<220> FEATURE:
<223> OTHER INFORMATION: DNA Aptamer

<400> SEQUENCE: 328
cttatttaat tgacttttag taaatgtttt tcagttttaa                            40

<210> SEQ ID NO 329
<211> LENGTH: 40
<212> TYPE: DNA
<213> ORGANISM: Artificial
<220> FEATURE:
<223> OTHER INFORMATION: DNA Aptamer

<400> SEQUENCE: 329
ctaattttaa atcagtattt ttttcattct atcgcactat                            40

<210> SEQ ID NO 330
<211> LENGTH: 40
<212> TYPE: DNA
<213> ORGANISM: Artificial
<220> FEATURE:
<223> OTHER INFORMATION: DNA Aptamer

<400> SEQUENCE: 330
gtctgatctc tttgaatctt ttaccgcata tactgttcgt                            40

<210> SEQ ID NO 331
<211> LENGTH: 40
<212> TYPE: DNA
<213> ORGANISM: Artificial
<220> FEATURE:
<223> OTHER INFORMATION: DNA Aptamer

<400> SEQUENCE: 331
accatttgat ggttttccct aattaccagt ttaatattaa                            40
```

<210> SEQ ID NO 332
<211> LENGTH: 40
<212> TYPE: DNA
<213> ORGANISM: Artificial
<220> FEATURE:
<223> OTHER INFORMATION: DNA Aptamer

<400> SEQUENCE: 332 cggatttttta gagtcttgaa atagttttct gtctccagac                    40

<210> SEQ ID NO 333
<211> LENGTH: 24
<212> TYPE: DNA
<213> ORGANISM: Artificial
<220> FEATURE:
<223> OTHER INFORMATION: DNA Aptamer

<400> SEQUENCE: 333
cgtaggaggg agatccctac aaac                                      24

<210> SEQ ID NO 334
<211> LENGTH: 39
<212> TYPE: DNA
<213> ORGANISM: Artificial
<220> FEATURE:
<223> OTHER INFORMATION: DNA Aptamer

<400> SEQUENCE: 334
cttttttatg aattcccttt aacgctcttt gatacattc                      39

<210> SEQ ID NO 335
<211> LENGTH: 24
<212> TYPE: DNA
<213> ORGANISM: Artificial
<220> FEATURE:
<223> OTHER INFORMATION: DNA Aptamer

<400> SEQUENCE: 335
cgtaggaggg agattcctac aaac                                      24

<210> SEQ ID NO 336
<211> LENGTH: 24
<212> TYPE: DNA
<213> ORGANISM: Artificial
<220> FEATURE:
<223> OTHER INFORMATION: DNA Aptamer

<400> SEQUENCE: 336
cgtaggaggg aggttcctgc aaac                                      24

<210> SEQ ID NO 337
<211> LENGTH: 24
<212> TYPE: DNA
<213> ORGANISM: Artificial
<220> FEATURE:
<223> OTHER INFORMATION: DNA Aptamer

<400> SEQUENCE: 337
cgtaggaggg agattcctac gaac                                      24

<210> SEQ ID NO 338
<211> LENGTH: 24
<212> TYPE: DNA
<213> ORGANISM: Artificial
<220> FEATURE:

<223> OTHER INFORMATION: DNA Aptamer

<400> SEQUENCE: 338
cgtaggaggg agattcctac aaac                                            24

<210> SEQ ID NO 339
<211> LENGTH: 24
<212> TYPE: DNA
<213> ORGANISM: Artificial
<220> FEATURE:
<223> OTHER INFORMATION: DNA Aptamer

<400> SEQUENCE: 339
cgtaggaggg agattcctac aaac                                            24

<210> SEQ ID NO 340
<211> LENGTH: 24
<212> TYPE: DNA
<213> ORGANISM: Artificial
<220> FEATURE:
<223> OTHER INFORMATION: DNA Aptamer

<400> SEQUENCE: 340
cgtaggaggg agattcctac aaac                                            24

<210> SEQ ID NO 341
<211> LENGTH: 24
<212> TYPE: DNA
<213> ORGANISM: Artificial
<220> FEATURE:
<223> OTHER INFORMATION: DNA Aptamer

<400> SEQUENCE: 341
cgtagggggg agattcctac aaac                                            24

<210> SEQ ID NO 342
<211> LENGTH: 24
<212> TYPE: DNA
<213> ORGANISM: Artificial
<220> FEATURE:
<223> OTHER INFORMATION: DNA Aptamer

<400> SEQUENCE: 342
cgtaggaggg agattcctac aaac                                            24

<210> SEQ ID NO 343
<211> LENGTH: 24
<212> TYPE: DNA
<213> ORGANISM: Artificial
<220> FEATURE:
<223> OTHER INFORMATION: DNA Aptamer

<400> SEQUENCE: 343
cgtaggaggg agattcctgc aaac                                            24

<210> SEQ ID NO 344
<211> LENGTH: 30
<212> TYPE: DNA
<213> ORGANISM: Artificial
<220> FEATURE:
<223> OTHER INFORMATION: DNA Aptamer

<400> SEQUENCE: 344
ctattcttgg tttaacggct tattataacc                                      30

```
<210> SEQ ID NO 345
<211> LENGTH: 24
<212> TYPE: DNA
<213> ORGANISM: Artificial
<220> FEATURE:
<223> OTHER INFORMATION: DNA Aptamer

<400> SEQUENCE: 345
cgtaagaggg agattcctac aaac                                          24

<210> SEQ ID NO 346
<211> LENGTH: 40
<212> TYPE: DNA
<213> ORGANISM: Artificial
<220> FEATURE:
<223> OTHER INFORMATION: DNA Aptamer

<400> SEQUENCE: 346
caagggtttt taagtggttc ggcgaagtga cacgtcgttt                          40

<210> SEQ ID NO 347
<211> LENGTH: 24
<212> TYPE: DNA
<213> ORGANISM: Artificial
<220> FEATURE:
<223> OTHER INFORMATION: DNA Aptamer

<400> SEQUENCE: 347
cgtaggaggg agattcctac aagc                                          24

<210> SEQ ID NO 348
<211> LENGTH: 38
<212> TYPE: DNA
<213> ORGANISM: Artificial
<220> FEATURE:
<223> OTHER INFORMATION: DNA Aptamer

<400> SEQUENCE: 348
gtttaaaatt attaactgtg ttgtcctagt cttgttca                            38

<210> SEQ ID NO 349
<211> LENGTH: 37
<212> TYPE: DNA
<213> ORGANISM: Artificial
<220> FEATURE:
<223> OTHER INFORMATION: DNA Aptamer

<400> SEQUENCE: 349
gtttaagtgg ttattgagac atttttaatc cgaaatc                             37

<210> SEQ ID NO 350
<211> LENGTH: 33
<212> TYPE: DNA
<213> ORGANISM: Artificial
<220> FEATURE:
<223> OTHER INFORMATION: DNA Aptamer

<400> SEQUENCE: 350
gtgatttatt aggaatcaag tctaagagca tat                                 33

<210> SEQ ID NO 351
<211> LENGTH: 24
<212> TYPE: DNA
<213> ORGANISM: Artificial
<220> FEATURE:
<223> OTHER INFORMATION: DNA Aptamer
```

```
<400> SEQUENCE: 351
cgtaggaggg agattcctac aagc                                          24

<210> SEQ ID NO 352
<211> LENGTH: 27
<212> TYPE: DNA
<213> ORGANISM: Artificial
<220> FEATURE:
<223> OTHER INFORMATION: DNA Aptamer

<400> SEQUENCE: 352 ctttttaag ttgagtatat gggtaaa                                        27

<210> SEQ ID NO 353
<211> LENGTH: 30
<212> TYPE: DNA
<213> ORGANISM: Artificial
<220> FEATURE:
<223> OTHER INFORMATION: DNA Aptamer

<400> SEQUENCE: 353
ggatatcttt ttttgatact ctgatgaatc                                    30

<210> SEQ ID NO 354
<211> LENGTH: 24
<212> TYPE: DNA
<213> ORGANISM: Artificial
<220> FEATURE:
<223> OTHER INFORMATION: DNA Aptamer

<400> SEQUENCE: 354
cgtaggaggg ggattcctac aaac                                          24

<210> SEQ ID NO 355
<211> LENGTH: 32
<212> TYPE: DNA
<213> ORGANISM: Artificial
<220> FEATURE:
<223> OTHER INFORMATION: DNA Aptamer

<400> SEQUENCE: 355
cgtaggaggg agattcctac aaacgctccc ca                                 32

<210> SEQ ID NO 356
<211> LENGTH: 27
<212> TYPE: DNA
<213> ORGANISM: Artificial
<220> FEATURE:
<223> OTHER INFORMATION: DNA Aptamer

<400> SEQUENCE: 356
cgaaatagtt ttaattgttg tatcccg                                       27

<210> SEQ ID NO 357
<211> LENGTH: 34
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
```

<400> SEQUENCE: 357
nntgatttat taggaatcaa gtctaanagc atat                    34

<210> SEQ ID NO 358
<211> LENGTH: 24
<212> TYPE: DNA
<213> ORGANISM: Artificial
<220> FEATURE:
<223> OTHER INFORMATION: DNA Aptamer

<400> SEQUENCE: 358
cgaaggaggg agattcctac aaac                               24

<210> SEQ ID NO 359
<211> LENGTH: 38
<212> TYPE: DNA
<213> ORGANISM: Artificial
<220> FEATURE:
<223> OTHER INFORMATION: DNA Aptamer

<400> SEQUENCE: 359
tcgattttgt ataattcttt atacctttg gtcttgtc                 38

<210> SEQ ID NO 360
<211> LENGTH: 24
<212> TYPE: DNA
<213> ORGANISM: Artificial
<220> FEATURE:
<223> OTHER INFORMATION: DNA Aptamer

<400> SEQUENCE: 360
cgtaggaggg agattcctac aaac                               24

<210> SEQ ID NO 361
<211> LENGTH: 24
<212> TYPE: DNA
<213> ORGANISM: Artificial
<220> FEATURE:
<223> OTHER INFORMATION: DNA Aptamer

<400> SEQUENCE: 361
cgtaggaggg agattcctac aaac                               24

<210> SEQ ID NO 362
<211> LENGTH: 24
<212> TYPE: DNA
<213> ORGANISM: Artificial
<220> FEATURE:
<223> OTHER INFORMATION: DNA Aptamer

<400> SEQUENCE: 362
cgtaggaggg agattcctac aaac                               24

<210> SEQ ID NO 363
<211> LENGTH: 24
<212> TYPE: DNA
<213> ORGANISM: Artificial
<220> FEATURE:
<223> OTHER INFORMATION: DNA Aptamer

<400> SEQUENCE: 363
cgtaggaggg agattcctac aaac                               24

<210> SEQ ID NO 364

```
<211> LENGTH: 24
<212> TYPE: DNA
<213> ORGANISM: Artificial
<220> FEATURE:
<223> OTHER INFORMATION: DNA Aptamer

<400> SEQUENCE: 364
cgtaggaggg agattcctgc aaac                                          24

<210> SEQ ID NO 365
<211> LENGTH: 24
<212> TYPE: DNA
<213> ORGANISM: Artificial
<220> FEATURE:
<223> OTHER INFORMATION: DNA Aptamer

<400> SEQUENCE: 365
cgtaggaggg aggttcctac aaac                                          24

<210> SEQ ID NO 366
<211> LENGTH: 24
<212> TYPE: DNA
<213> ORGANISM: Artificial
<220> FEATURE:
<223> OTHER INFORMATION: DNA Aptamer

<400> SEQUENCE: 366
cgtaggaggg agattcctgc aaac                                          24

<210> SEQ ID NO 367
<211> LENGTH: 28
<212> TYPE: DNA
<213> ORGANISM: Artificial
<220> FEATURE:
<223> OTHER INFORMATION: DNA Aptamer

<400> SEQUENCE: 367
gggagggagg gggcgacggc caggagcg                                      28

<210> SEQ ID NO 368
<211> LENGTH: 35
<212> TYPE: DNA
<213> ORGANISM: Artificial
<220> FEATURE:
<223> OTHER INFORMATION: DNA Aptamer

<400> SEQUENCE: 368
cgtaggaggg agattcctac aaacgctctc catcc                              35

<210> SEQ ID NO 369
<211> LENGTH: 24
<212> TYPE: DNA
<213> ORGANISM: Artificial
<220> FEATURE:
<223> OTHER INFORMATION: DNA Aptamer

<400> SEQUENCE: 369
cgtagggggg agatttctgc aaac                                          24

<210> SEQ ID NO 370
<211> LENGTH: 24
<212> TYPE: DNA
<213> ORGANISM: Artificial
<220> FEATURE:
<223> OTHER INFORMATION: DNA Aptamer

<400> SEQUENCE: 370
```
cgtaggaggg agattcctgc aaac                                          24

<210> SEQ ID NO 371
<211> LENGTH: 24
<212> TYPE: DNA
<213> ORGANISM: Artificial
<220> FEATURE:
<223> OTHER INFORMATION: DNA Aptamer

<400> SEQUENCE: 371
cgtaggaggg ggattcctac aaac                                          24

<210> SEQ ID NO 372
<211> LENGTH: 24
<212> TYPE: DNA
<213> ORGANISM: Artificial
<220> FEATURE:
<223> OTHER INFORMATION: DNA Aptamer

<400> SEQUENCE: 372
cgtaggaggg agattcctac aaac                                          24

<210> SEQ ID NO 373
<211> LENGTH: 28
<212> TYPE: DNA
<213> ORGANISM: Artificial
<220> FEATURE:
<223> OTHER INFORMATION: DNA Aptamer

<400> SEQUENCE: 373
cgtaggaggg agattcctac aagcactc                                      28

<210> SEQ ID NO 374
<211> LENGTH: 24
<212> TYPE: DNA
<213> ORGANISM: Artificial
<220> FEATURE:
<223> OTHER INFORMATION: DNA Aptamer

<400> SEQUENCE: 374
cgtaggaggg agattcctac aaac                                          24

<210> SEQ ID NO 375
<211> LENGTH: 36
<212> TYPE: DNA
<213> ORGANISM: Artificial
<220> FEATURE:
<223> OTHER INFORMATION: DNA Aptamer

<400> SEQUENCE: 375
tctaatatgt tttataaact cggttttacc gtctcg                             36

<210> SEQ ID NO 376
<211> LENGTH: 24
<212> TYPE: DNA
<213> ORGANISM: Artificial
<220> FEATURE:
<223> OTHER INFORMATION: DNA Aptamer

<400> SEQUENCE: 376
cgtaggaggg agattcctac aaac                                          24

<210> SEQ ID NO 377
<211> LENGTH: 40
<212> TYPE: DNA

```
<213> ORGANISM: Artificial
<220> FEATURE:
<223> OTHER INFORMATION: DNA Aptamer

<400> SEQUENCE: 377
tgatcttatt tagaaactcc cttccgttgg gagggaccag                    40

<210> SEQ ID NO 378
<211> LENGTH: 22
<212> TYPE: DNA
<213> ORGANISM: Artificial
<220> FEATURE:
<223> OTHER INFORMATION: DNA Aptamer

<400> SEQUENCE: 378
ccgatgtagg agtgaggaga gc                                      22

<210> SEQ ID NO 379
<211> LENGTH: 45
<212> TYPE: DNA
<213> ORGANISM: Artificial
<220> FEATURE:
<223> OTHER INFORMATION: DNA Aptamer

<400> SEQUENCE: 379
ccgatgtagg agtgaggtct tgcctcggga ttacagatgc gcccg             45

<210> SEQ ID NO 380
<211> LENGTH: 45
<212> TYPE: DNA
<213> ORGANISM: Artificial
<220> FEATURE:
<223> OTHER INFORMATION: DNA Aptamer

<400> SEQUENCE: 380
ccgatgtagg agtgagtaat gatcaaagtc aggaaccgcg ttccc             45

<210> SEQ ID NO 381
<211> LENGTH: 22
<212> TYPE: DNA
<213> ORGANISM: Artificial
<220> FEATURE:
<223> OTHER INFORMATION: DNA Aptamer

<400> SEQUENCE: 381
ccgatgtagg agtgagccgg at                                      22

<210> SEQ ID NO 382
<211> LENGTH: 46
<212> TYPE: DNA
<213> ORGANISM: Artificial
<220> FEATURE:
<223> OTHER INFORMATION: DNA Aptamer

<400> SEQUENCE: 382
ccgatgtagg agtgagggct ccagtattct ataccagctt attcaa            46

<210> SEQ ID NO 383
<211> LENGTH: 45
<212> TYPE: DNA
<213> ORGANISM: Artificial
<220> FEATURE:
<223> OTHER INFORMATION: DNA Aptamer

<400> SEQUENCE: 383
ccgatgtagg agtgaggtgg actaaccata taccagctta ttcaa             45
```

<210> SEQ ID NO 384
<211> LENGTH: 45
<212> TYPE: DNA
<213> ORGANISM: Artificial
<220> FEATURE:
<223> OTHER INFORMATION: DNA Aptamer

<400> SEQUENCE: 384
ccgatgtagg agtgaggtgg actaaccata taccagctta ttcaa          45

<210> SEQ ID NO 385
<211> LENGTH: 45
<212> TYPE: DNA
<213> ORGANISM: Artificial
<220> FEATURE:
<223> OTHER INFORMATION: DNA Aptamer

<400> SEQUENCE: 385
ccgatgtagg agtgaggaag atttccacta taccagctta ttcaa          45

<210> SEQ ID NO 386
<211> LENGTH: 46
<212> TYPE: DNA
<213> ORGANISM: Artificial
<220> FEATURE:
<223> OTHER INFORMATION: DNA Aptamer

<400> SEQUENCE: 386
ccgatgtagg agtgaggata cgttcgaatg gcttacatca taccccc          46

<210> SEQ ID NO 387
<211> LENGTH: 43
<212> TYPE: DNA
<213> ORGANISM: Artificial
<220> FEATURE:
<223> OTHER INFORMATION: DNA Aptamer

<400> SEQUENCE: 387
ccgatgtagg agtgaggcta accccgtata ccagcttatt caa            43

<210> SEQ ID NO 388
<211> LENGTH: 41
<212> TYPE: DNA
<213> ORGANISM: Artificial
<220> FEATURE:
<223> OTHER INFORMATION: DNA Aptamer

<400> SEQUENCE: 388
ccgatgtagg agtgaggcta accccgtata ccagcttatt c              41

<210> SEQ ID NO 389
<211> LENGTH: 41
<212> TYPE: DNA
<213> ORGANISM: Artificial
<220> FEATURE:
<223> OTHER INFORMATION: DNA Aptamer

<400> SEQUENCE: 389
ccgatgtagg agtgaggcta accccgtata ccagcttatt c              41

<210> SEQ ID NO 390
<211> LENGTH: 23
<212> TYPE: DNA
<213> ORGANISM: Artificial
<220> FEATURE:

-continued

<223> OTHER INFORMATION: DNA Aptamer

<400> SEQUENCE: 390
ccgatgtagg agtgagaccg ctg                                           23

<210> SEQ ID NO 391
<211> LENGTH: 42
<212> TYPE: DNA
<213> ORGANISM: Artificial
<220> FEATURE:
<223> OTHER INFORMATION: DNA Aptamer

<400> SEQUENCE: 391
ccgatgtagg agtgagggcc tgttttatac cagcttattc aa                      42

<210> SEQ ID NO 392
<211> LENGTH: 22
<212> TYPE: DNA
<213> ORGANISM: Artificial
<220> FEATURE:
<223> OTHER INFORMATION: DNA Aptamer

<400> SEQUENCE: 392
ccgatgtagg agtgagccca gt                                            22

<210> SEQ ID NO 393
<211> LENGTH: 22
<212> TYPE: DNA
<213> ORGANISM: Artificial
<220> FEATURE:
<223> OTHER INFORMATION: DNA Aptamer

<400> SEQUENCE: 393
ccgatgtagg agtgagccca gt                                            22

<210> SEQ ID NO 394
<211> LENGTH: 22
<212> TYPE: DNA
<213> ORGANISM: Artificial
<220> FEATURE:
<223> OTHER INFORMATION: DNA Aptamer

<400> SEQUENCE: 394
ccgatgtagg agtgagccca gt                                            22

<210> SEQ ID NO 395
<211> LENGTH: 22
<212> TYPE: DNA
<213> ORGANISM: Artificial
<220> FEATURE:
<223> OTHER INFORMATION: DNA Aptamer

<400> SEQUENCE: 395
ccgatgtagg agtgagccca gt                                            22

<210> SEQ ID NO 396
<211> LENGTH: 22
<212> TYPE: DNA
<213> ORGANISM: Artificial
<220> FEATURE:
<223> OTHER INFORMATION: DNA Aptamer

<400> SEQUENCE: 396
ccgatgtagg agtgagccca gt                                            22

```
<210> SEQ ID NO 397
<211> LENGTH: 22
<212> TYPE: DNA
<213> ORGANISM: Artificial
<220> FEATURE:
<223> OTHER INFORMATION: DNA Aptamer

<400> SEQUENCE: 397
ccgatgtagg agtgagccca gt                                              22

<210> SEQ ID NO 398
<211> LENGTH: 22
<212> TYPE: DNA
<213> ORGANISM: Artificial
<220> FEATURE:
<223> OTHER INFORMATION: DNA Aptamer

<400> SEQUENCE: 398
ccgatgtagg agtgagccca gt                                              22

<210> SEQ ID NO 399
<211> LENGTH: 41
<212> TYPE: DNA
<213> ORGANISM: Artificial
<220> FEATURE:
<223> OTHER INFORMATION: DNA Aptamer

<400> SEQUENCE: 399
ccgatgtagg agtgaggctg gcagtatacc agcttattca a                         41

<210> SEQ ID NO 400
<211> LENGTH: 24
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (9)..(9)
<223> OTHER INFORMATION: n is a, c, g, or t

<400> SEQUENCE: 400
ccgatgtang agtgagctaa taaa                                            24

<210> SEQ ID NO 401
<211> LENGTH: 40
<212> TYPE: DNA
<213> ORGANISM: Artificial
<220> FEATURE:
<223> OTHER INFORMATION: DNA Aptamer

<400> SEQUENCE: 401
caatatgtct aatttttta catggcggca tggtattggc                            40

<210> SEQ ID NO 402
<211> LENGTH: 40
<212> TYPE: DNA
<213> ORGANISM: Artificial
<220> FEATURE:
<223> OTHER INFORMATION: DNA Aptamer

<400> SEQUENCE: 402
caatacaata ctatatttgt gtcaatctcg tacttctgac                           40

<210> SEQ ID NO 403
<211> LENGTH: 40
<212> TYPE: DNA
```

```
<213> ORGANISM: Artificial
<220> FEATURE:
<223> OTHER INFORMATION: DNA Aptamer

<400> SEQUENCE: 403
taattatctc cttaatcatg gttattcttt gaatctatca                              40

<210> SEQ ID NO 404
<211> LENGTH: 40
<212> TYPE: DNA
<213> ORGANISM: Artificial
<220> FEATURE:
<223> OTHER INFORMATION: DNA Aptamer

<400> SEQUENCE: 404
atagtctaat acaacttaaa gcaattccat gattataaat                              40

<210> SEQ ID NO 405
<211> LENGTH: 40
<212> TYPE: DNA
<213> ORGANISM: Artificial
<220> FEATURE:
<223> OTHER INFORMATION: DNA Aptamer

<400> SEQUENCE: 405
attcgtttac attattcggc aattcttatt tctgttggag                              40

<210> SEQ ID NO 406
<211> LENGTH: 39
<212> TYPE: DNA
<213> ORGANISM: Artificial
<220> FEATURE:
<223> OTHER INFORMATION: DNA Aptamer

<400> SEQUENCE: 406
agaggcggct gagatcaatc tccgctcagg gagcgagta                               39

<210> SEQ ID NO 407
<211> LENGTH: 40
<212> TYPE: DNA
<213> ORGANISM: Artificial
<220> FEATURE:
<223> OTHER INFORMATION: DNA Aptamer

<400> SEQUENCE: 407
gtaataggtg atttcctcaa tttgaattag atcacaaaat                              40

<210> SEQ ID NO 408
<211> LENGTH: 40
<212> TYPE: DNA
<213> ORGANISM: Artificial
<220> FEATURE:
<223> OTHER INFORMATION: DNA Aptamer

<400> SEQUENCE: 408
catgtgatgc tcacggtggc accccaggcg agtacgcagt                              40

<210> SEQ ID NO 409
<211> LENGTH: 40
<212> TYPE: DNA
<213> ORGANISM: Artificial
<220> FEATURE:
<223> OTHER INFORMATION: DNA Aptamer

<400> SEQUENCE: 409
gatggtgttt gtacacaact ttacatttta gtcctacaag                              40
```

<210> SEQ ID NO 410
<211> LENGTH: 40
<212> TYPE: DNA
<213> ORGANISM: Artificial
<220> FEATURE:
<223> OTHER INFORMATION: DNA Aptamer

<400> SEQUENCE: 410
caagagtgtt agacattatc tcagcgctgc caattatatt                          40

<210> SEQ ID NO 411
<211> LENGTH: 40
<212> TYPE: DNA
<213> ORGANISM: Artificial
<220> FEATURE:
<223> OTHER INFORMATION: DNA Aptamer

<400> SEQUENCE: 411
ccttgcgaca aaccctcgg gacctctatc aagccaacgt                           40

<210> SEQ ID NO 412
<211> LENGTH: 39
<212> TYPE: DNA
<213> ORGANISM: Artificial
<220> FEATURE:
<223> OTHER INFORMATION: DNA Aptamer

<400> SEQUENCE: 412
accatatgaa tacaacacca ttcagtttat tatcctttt                           39

<210> SEQ ID NO 413
<211> LENGTH: 40
<212> TYPE: DNA
<213> ORGANISM: Artificial
<220> FEATURE:
<223> OTHER INFORMATION: DNA Aptamer

<400> SEQUENCE: 413
aagatcttta ttaagcaaac aatgttaact atagagcgtt                          40

<210> SEQ ID NO 414
<211> LENGTH: 40
<212> TYPE: DNA
<213> ORGANISM: Artificial
<220> FEATURE:
<223> OTHER INFORMATION: DNA Aptamer

<400> SEQUENCE: 414
gaattacatt caaaattttt cttctggcat ctgtaatacc                          40

<210> SEQ ID NO 415
<211> LENGTH: 40
<212> TYPE: DNA
<213> ORGANISM: Artificial
<220> FEATURE:
<223> OTHER INFORMATION: DNA Aptamer

<400> SEQUENCE: 415
acaatgtata attatatcga ttcagattag tctacaggac                          40

<210> SEQ ID NO 416
<211> LENGTH: 40
<212> TYPE: DNA
<213> ORGANISM: Artificial
<220> FEATURE:

<223> OTHER INFORMATION: DNA Aptamer

<400> SEQUENCE: 416
cacagaatgt ggatattttc ttgcatctct tcctttagt                             40

<210> SEQ ID NO 417
<211> LENGTH: 40
<212> TYPE: DNA
<213> ORGANISM: Artificial
<220> FEATURE:
<223> OTHER INFORMATION: DNA Aptamer

<400> SEQUENCE: 417
tagcgcaatt cgtagtttca ggtatctgga ttcaggccgt                             40

<210> SEQ ID NO 418
<211> LENGTH: 40
<212> TYPE: DNA
<213> ORGANISM: Artificial
<220> FEATURE:
<223> OTHER INFORMATION: DNA Aptamer

<400> SEQUENCE: 418
gtaatcgcgt tactactatc tctccgtcca ctttcaatac                             40

<210> SEQ ID NO 419
<211> LENGTH: 40
<212> TYPE: DNA
<213> ORGANISM: Artificial
<220> FEATURE:
<223> OTHER INFORMATION: DNA Aptamer

<400> SEQUENCE: 419
caaagtaaaa ttaacagata gtacgttctc aatctcgcga                             40

<210> SEQ ID NO 420
<211> LENGTH: 40
<212> TYPE: DNA
<213> ORGANISM: Artificial
<220> FEATURE:
<223> OTHER INFORMATION: DNA Aptamer

<400> SEQUENCE: 420
ctgggcattt ctaaggagtc atacaactat ttcaggttat                             40

<210> SEQ ID NO 421
<211> LENGTH: 40
<212> TYPE: DNA
<213> ORGANISM: Artificial
<220> FEATURE:
<223> OTHER INFORMATION: DNA Aptamer

<400> SEQUENCE: 421
tgatacaaat actctcaatc aaagccaata tgtcgcaaaa                             40

<210> SEQ ID NO 422
<211> LENGTH: 40
<212> TYPE: DNA
<213> ORGANISM: Artificial
<220> FEATURE:
<223> OTHER INFORMATION: DNA Aptamer

<400> SEQUENCE: 422
gcagggcgcg actcggcgtg gaacgaggtt caatagtcca                             40

<210> SEQ ID NO 423
<211> LENGTH: 40
<212> TYPE: DNA
<213> ORGANISM: Artificial
<220> FEATURE:
<223> OTHER INFORMATION: DNA Aptamer

<400> SEQUENCE: 423
atcaagaatt gataatttta ggaattgcgt atcgctgcta                              40

<210> SEQ ID NO 424
<211> LENGTH: 40
<212> TYPE: DNA
<213> ORGANISM: Artificial
<220> FEATURE:
<223> OTHER INFORMATION: DNA Aptamer

<400> SEQUENCE: 424
tagtttatca ggagcgatca ctgatcatga gtaacttta                               40

<210> SEQ ID NO 425
<211> LENGTH: 40
<212> TYPE: DNA
<213> ORGANISM: Artificial
<220> FEATURE:
<223> OTHER INFORMATION: DNA Aptamer

<400> SEQUENCE: 425
gtttagttaa aatccgtttg agaacaaatt acaaaccta                               40

<210> SEQ ID NO 426
<211> LENGTH: 40
<212> TYPE: DNA
<213> ORGANISM: Artificial
<220> FEATURE:
<223> OTHER INFORMATION: DNA Aptamer

<400> SEQUENCE: 426
aaaagtcgta atagcccggg acaacgccag ctaaagaaa                               40

<210> SEQ ID NO 427
<211> LENGTH: 39
<212> TYPE: DNA
<213> ORGANISM: Artificial
<220> FEATURE:
<223> OTHER INFORMATION: DNA Aptamer

<400> SEQUENCE: 427
ccgcatttat cagtttaccg ccccataaac ataaccgct                               39

<210> SEQ ID NO 428
<211> LENGTH: 40
<212> TYPE: DNA
<213> ORGANISM: Artificial
<220> FEATURE:
<223> OTHER INFORMATION: DNA Aptamer

<400> SEQUENCE: 428
atgtacttca cttcagtttt ctttaaacac gtttcacata                              40

<210> SEQ ID NO 429
<211> LENGTH: 40
<212> TYPE: DNA
<213> ORGANISM: Artificial
<220> FEATURE:
<223> OTHER INFORMATION: DNA Aptamer

<400> SEQUENCE: 429
cgtcagtctg ctttcttggc ttgtgtactt aataataagg                40

<210> SEQ ID NO 430
<211> LENGTH: 40
<212> TYPE: DNA
<213> ORGANISM: Artificial
<220> FEATURE:
<223> OTHER INFORMATION: DNA Aptamer

<400> SEQUENCE: 430
aaccagtaag gtcagagtaa tagtatgcca gtcttgatct                40

<210> SEQ ID NO 431
<211> LENGTH: 40
<212> TYPE: DNA
<213> ORGANISM: Artificial
<220> FEATURE:
<223> OTHER INFORMATION: DNA Aptamer

<400> SEQUENCE: 431
aattatgctc atgattttct tcaaaaaggc tcgcgcaatt                40

<210> SEQ ID NO 432
<211> LENGTH: 40
<212> TYPE: DNA
<213> ORGANISM: Artificial
<220> FEATURE:
<223> OTHER INFORMATION: DNA Aptamer

<400> SEQUENCE: 432 agaatttta agggttatct caagtcttga acatctaacg                40

<210> SEQ ID NO 433
<211> LENGTH: 40
<212> TYPE: DNA
<213> ORGANISM: Artificial
<220> FEATURE:
<223> OTHER INFORMATION: DNA Aptamer

<400> SEQUENCE: 433
ggctgttaaa cttacttttc ttcagtaatt gccgttgaca                40

<210> SEQ ID NO 434
<211> LENGTH: 39
<212> TYPE: DNA
<213> ORGANISM: Artificial
<220> FEATURE:
<223> OTHER INFORMATION: DNA Aptamer

<400> SEQUENCE: 434
tcttcttgca catattttc tccgtgagac atgtaaata                39

<210> SEQ ID NO 435
<211> LENGTH: 40
<212> TYPE: DNA
<213> ORGANISM: Artificial
<220> FEATURE:
<223> OTHER INFORMATION: DNA Aptamer

<400> SEQUENCE: 435
cgtctaatca atattgttta atgtattttg ccagacacta                40

<210> SEQ ID NO 436
<211> LENGTH: 40

```
<212> TYPE: DNA
<213> ORGANISM: Artificial
<220> FEATURE:
<223> OTHER INFORMATION: DNA Aptamer

<400> SEQUENCE: 436
cccagaatgt agcttacctt ttttgatcgt cccagtcctt                               40

<210> SEQ ID NO 437
<211> LENGTH: 40
<212> TYPE: DNA
<213> ORGANISM: Artificial
<220> FEATURE:
<223> OTHER INFORMATION: DNA Aptamer

<400> SEQUENCE: 437
gtgtgcccgg tcaacgcgtg ggccgcgtgg tacggggcgt                               40

<210> SEQ ID NO 438
<211> LENGTH: 40
<212> TYPE: DNA
<213> ORGANISM: Artificial
<220> FEATURE:
<223> OTHER INFORMATION: DNA Aptamer

<400> SEQUENCE: 438
agcgcgatat tacggtctcg aaccaaaacc atcacggttc                               40

<210> SEQ ID NO 439
<211> LENGTH: 40
<212> TYPE: DNA
<213> ORGANISM: Artificial
<220> FEATURE:
<223> OTHER INFORMATION: DNA Aptamer

<400> SEQUENCE: 439
atcgacttaa tttaaagtga aaagatccct ttccacaaat                               40

<210> SEQ ID NO 440
<211> LENGTH: 40
<212> TYPE: DNA
<213> ORGANISM: Artificial
<220> FEATURE:
<223> OTHER INFORMATION: DNA Aptamer

<400> SEQUENCE: 440
tcgttattag gttgagtaac ccattctctt agccgctata                               40

<210> SEQ ID NO 441
<211> LENGTH: 40
<212> TYPE: DNA
<213> ORGANISM: Artificial
<220> FEATURE:
<223> OTHER INFORMATION: DNA Aptamer

<400> SEQUENCE: 441
tggtgtttta caaatgagt acgtttttaa tctcgcccgg                                40

<210> SEQ ID NO 442
<211> LENGTH: 40
<212> TYPE: DNA
<213> ORGANISM: Artificial
<220> FEATURE:
<223> OTHER INFORMATION: DNA Aptamer

<400> SEQUENCE: 442
```
ccagggtaca catcacgaaa tatctaacct gattgcaaac       40

<210> SEQ ID NO 443
<211> LENGTH: 40
<212> TYPE: DNA
<213> ORGANISM: Artificial
<220> FEATURE:
<223> OTHER INFORMATION: DNA Aptamer

<400> SEQUENCE: 443
tatcgtttag tttacaactt tcaaatttaa taaatcgaat       40

<210> SEQ ID NO 444
<211> LENGTH: 40
<212> TYPE: DNA
<213> ORGANISM: Artificial
<220> FEATURE:
<223> OTHER INFORMATION: DNA Aptamer

<400> SEQUENCE: 444
aactgtgttt taggacttca ttgtcttaat tctcttccct       40

<210> SEQ ID NO 445
<211> LENGTH: 40
<212> TYPE: DNA
<213> ORGANISM: Artificial
<220> FEATURE:
<223> OTHER INFORMATION: DNA Aptamer

<400> SEQUENCE: 445
cgtatatata ggacgttttt gacagtttta tttattaaat       40

<210> SEQ ID NO 446
<211> LENGTH: 40
<212> TYPE: DNA
<213> ORGANISM: Artificial
<220> FEATURE:
<223> OTHER INFORMATION: DNA Aptamer

<400> SEQUENCE: 446
cgttcattgt tggtatagtt aagttctgac agatcaataa       40

<210> SEQ ID NO 447
<211> LENGTH: 38
<212> TYPE: DNA
<213> ORGANISM: Artificial
<220> FEATURE:
<223> OTHER INFORMATION: DNA Aptamer

<400> SEQUENCE: 447
atagtttaaa tttaatcttc tgccaccctt cactttca       38

<210> SEQ ID NO 448
<211> LENGTH: 40
<212> TYPE: DNA
<213> ORGANISM: Artificial
<220> FEATURE:
<223> OTHER INFORMATION: DNA Aptamer

<400> SEQUENCE: 448
ccctggccag gcgggcgccc ggccgcgggc gtggggacg       40

<210> SEQ ID NO 449
<211> LENGTH: 40
<212> TYPE: DNA
<213> ORGANISM: Artificial

<220> FEATURE:
<223> OTHER INFORMATION: DNA Aptamer

<400> SEQUENCE: 449
tttatattaa gcaacttttt gagagttgat tgataattta          40

<210> SEQ ID NO 450
<211> LENGTH: 40
<212> TYPE: DNA
<213> ORGANISM: Artificial
<220> FEATURE:
<223> OTHER INFORMATION: DNA Aptamer

<400> SEQUENCE: 450
ggtggataac tgtgtctgct tgccagacta cgtcctcaga          40

<210> SEQ ID NO 451
<211> LENGTH: 40
<212> TYPE: DNA
<213> ORGANISM: Artificial
<220> FEATURE:
<223> OTHER INFORMATION: DNA Aptamer

<400> SEQUENCE: 451
acgcgcggct gtggggaagg tacaggttcc gaacgatgga          40

<210> SEQ ID NO 452
<211> LENGTH: 40
<212> TYPE: DNA
<213> ORGANISM: Artificial
<220> FEATURE:
<223> OTHER INFORMATION: DNA Aptamer

<400> SEQUENCE: 452
aaaagagagg aaccggtctt ggcctgctct aagattttgt          40

<210> SEQ ID NO 453
<211> LENGTH: 40
<212> TYPE: DNA
<213> ORGANISM: Artificial
<220> FEATURE:
<223> OTHER INFORMATION: DNA Aptamer

<400> SEQUENCE: 453
ccgatattgg atctaagtgt tgcatcaaca ttaattcaga          40

<210> SEQ ID NO 454
<211> LENGTH: 40
<212> TYPE: DNA
<213> ORGANISM: Artificial
<220> FEATURE:
<223> OTHER INFORMATION: DNA Aptamer

<400> SEQUENCE: 454
ttccttcgtc ttaatactgt tgccagttaa ttaatttgcg          40

<210> SEQ ID NO 455
<211> LENGTH: 40
<212> TYPE: DNA
<213> ORGANISM: Artificial
<220> FEATURE:
<223> OTHER INFORMATION: DNA Aptamer

<400> SEQUENCE: 455
acaaaggatg atcttcttat ccttcaacta gatccggtcc          40

<210> SEQ ID NO 456
<211> LENGTH: 40
<212> TYPE: DNA
<213> ORGANISM: Artificial
<220> FEATURE:
<223> OTHER INFORMATION: DNA Aptamer

<400> SEQUENCE: 456
tggagtttat aatactcgag gctagtagtg ccattttaca                              40

<210> SEQ ID NO 457
<211> LENGTH: 40
<212> TYPE: DNA
<213> ORGANISM: Artificial
<220> FEATURE:
<223> OTHER INFORMATION: DNA Aptamer

<400> SEQUENCE: 457
caaataatcg ttttataatt accaacacat tttggttaac                              40

<210> SEQ ID NO 458
<211> LENGTH: 40
<212> TYPE: DNA
<213> ORGANISM: Artificial
<220> FEATURE:
<223> OTHER INFORMATION: DNA Aptamer

<400> SEQUENCE: 458
acagctctca cgctccgtca agaccaattt ccattcggtt                              40

<210> SEQ ID NO 459
<211> LENGTH: 40
<212> TYPE: DNA
<213> ORGANISM: Artificial
<220> FEATURE:
<223> OTHER INFORMATION: DNA Aptamer

<400> SEQUENCE: 459
gcacatctcc cgttcgactt ttttatcttc gagcacctaa                              40

<210> SEQ ID NO 460
<211> LENGTH: 40
<212> TYPE: DNA
<213> ORGANISM: Artificial
<220> FEATURE:
<223> OTHER INFORMATION: DNA Aptamer

<400> SEQUENCE: 460
ccatgtagca caaaacaacg atataagaac tacatttagt                              40

<210> SEQ ID NO 461
<211> LENGTH: 40
<212> TYPE: DNA
<213> ORGANISM: Artificial
<220> FEATURE:
<223> OTHER INFORMATION: DNA Aptamer

<400> SEQUENCE: 461
tactcttgtt taaactagaa cagtaaaata ttaattctta                              40

<210> SEQ ID NO 462
<211> LENGTH: 40
<212> TYPE: DNA
<213> ORGANISM: Artificial
<220> FEATURE:
<223> OTHER INFORMATION: DNA Aptamer

```
<400> SEQUENCE: 462
ggctttctaa tctaacacga tctcctctcc ttacgccgtg                              40

<210> SEQ ID NO 463
<211> LENGTH: 39
<212> TYPE: DNA
<213> ORGANISM: Artificial
<220> FEATURE:
<223> OTHER INFORMATION: DNA Aptamer

<400> SEQUENCE: 463
taaaatggat gttttgaaaa ttctggtatc tcgagtgtc                               39

<210> SEQ ID NO 464
<211> LENGTH: 40
<212> TYPE: DNA
<213> ORGANISM: Artificial
<220> FEATURE:
<223> OTHER INFORMATION: DNA Aptamer

<400> SEQUENCE: 464
tatacattga gataaaaccg atcttgaaat tttccgcacg                              40

<210> SEQ ID NO 465
<211> LENGTH: 40
<212> TYPE: DNA
<213> ORGANISM: Artificial
<220> FEATURE:
<223> OTHER INFORMATION: DNA Aptamer

<400> SEQUENCE: 465
acaagaacta ttttatcaa agacgtcacc aacttaaggc                               40

<210> SEQ ID NO 466
<211> LENGTH: 40
<212> TYPE: DNA
<213> ORGANISM: Artificial
<220> FEATURE:
<223> OTHER INFORMATION: DNA Aptamer

<400> SEQUENCE: 466
gcttagtaaa attctttctt gtcaatttcg ttataagtcc                              40

<210> SEQ ID NO 467
<211> LENGTH: 40
<212> TYPE: DNA
<213> ORGANISM: Artificial
<220> FEATURE:
<223> OTHER INFORMATION: DNA Aptamer

<400> SEQUENCE: 467
tggcctaatc tcggagactg gccgctgtgg gcgcgggcct                              40

<210> SEQ ID NO 468
<211> LENGTH: 40
<212> TYPE: DNA
<213> ORGANISM: Artificial
<220> FEATURE:
<223> OTHER INFORMATION: DNA Aptamer

<400> SEQUENCE: 468
ggtcaatgtc tagttattaa aatatgtttt cataacaaat                              40

<210> SEQ ID NO 469
```

```
<210> SEQ ID NO 469
<211> LENGTH: 40
<212> TYPE: DNA
<213> ORGANISM: Artificial
<220> FEATURE:
<223> OTHER INFORMATION: DNA Aptamer

<400> SEQUENCE: 469
atattgtaaa tactcttccc tcatacagat gatccggtaa                          40

<210> SEQ ID NO 470
<211> LENGTH: 40
<212> TYPE: DNA
<213> ORGANISM: Artificial
<220> FEATURE:
<223> OTHER INFORMATION: DNA Aptamer

<400> SEQUENCE: 470
cgagaaacct acttatctta ttcttcaatt cgatttatta                          40

<210> SEQ ID NO 471
<211> LENGTH: 39
<212> TYPE: DNA
<213> ORGANISM: Artificial
<220> FEATURE:
<223> OTHER INFORMATION: DNA Aptamer

<400> SEQUENCE: 471
gcttacctta acaaaattgc aacccaaccc ttcaccggc                           39

<210> SEQ ID NO 472
<211> LENGTH: 40
<212> TYPE: DNA
<213> ORGANISM: Artificial
<220> FEATURE:
<223> OTHER INFORMATION: DNA Aptamer

<400> SEQUENCE: 472
gtgacggtga tggtacccgc actgcggcgg cggccagcag                          40

<210> SEQ ID NO 473
<211> LENGTH: 40
<212> TYPE: DNA
<213> ORGANISM: Artificial
<220> FEATURE:
<223> OTHER INFORMATION: DNA Aptamer

<400> SEQUENCE: 473
tctaattatg ttacaaaata attgttatgc tccgcaaata                          40

<210> SEQ ID NO 474
<211> LENGTH: 40
<212> TYPE: DNA
<213> ORGANISM: Artificial
<220> FEATURE:
<223> OTHER INFORMATION: DNA Aptamer

<400> SEQUENCE: 474
ctgccaagtc attacagaat attaaaattt gtcatgtatt                          40

<210> SEQ ID NO 475
<211> LENGTH: 39
<212> TYPE: DNA
<213> ORGANISM: Artificial
<220> FEATURE:
<223> OTHER INFORMATION: DNA Aptamer

<400> SEQUENCE: 475
```

```
tcatttaatt gtcctaaatc tgaaaattta ttatatttc                              39

<210> SEQ ID NO 476
<211> LENGTH: 40
<212> TYPE: DNA
<213> ORGANISM: Artificial
<220> FEATURE:
<223> OTHER INFORMATION: DNA Aptamer

<400> SEQUENCE: 476
aaacctgcaa aatttagggc caatgtgtgt attgaacggg                              40

<210> SEQ ID NO 477
<211> LENGTH: 40
<212> TYPE: DNA
<213> ORGANISM: Artificial
<220> FEATURE:
<223> OTHER INFORMATION: DNA Aptamer

<400> SEQUENCE: 477
atcagaagct tcgatctatt cgcctcattc actcactcta                              40

<210> SEQ ID NO 478
<211> LENGTH: 40
<212> TYPE: DNA
<213> ORGANISM: Artificial
<220> FEATURE:
<223> OTHER INFORMATION: DNA Aptamer

<400> SEQUENCE: 478
accctataag ctgagataag cattctgtgg acgaaaagtt                              40

<210> SEQ ID NO 479
<211> LENGTH: 40
<212> TYPE: DNA
<213> ORGANISM: Artificial
<220> FEATURE:
<223> OTHER INFORMATION: DNA Aptamer

<400> SEQUENCE: 479
ggtcgaaaca gagaagcctc aaacttaaac ttccaatgtg                              40

<210> SEQ ID NO 480
<211> LENGTH: 38
<212> TYPE: DNA
<213> ORGANISM: Artificial
<220> FEATURE:
<223> OTHER INFORMATION: DNA Aptamer

<400> SEQUENCE: 480
aatttcattc tttaaattgt tttcttaatt ttagctta                                38

<210> SEQ ID NO 481
<211> LENGTH: 40
<212> TYPE: DNA
<213> ORGANISM: Artificial
<220> FEATURE:
<223> OTHER INFORMATION: DNA Aptamer

<400> SEQUENCE: 481
tcgtatttac ccctattaac atcagatcgt gtcataacgc                              40

<210> SEQ ID NO 482
<211> LENGTH: 40
<212> TYPE: DNA
```

```
<213> ORGANISM: Artificial
<220> FEATURE:
<223> OTHER INFORMATION: DNA Aptamer

<400> SEQUENCE: 482
gttatagtaa tattggttct agctctcagt aatatcaaaa                              40

<210> SEQ ID NO 483
<211> LENGTH: 40
<212> TYPE: DNA
<213> ORGANISM: Artificial
<220> FEATURE:
<223> OTHER INFORMATION: DNA Aptamer

<400> SEQUENCE: 483
acggagattg attctgttta aaacggtact atatcttgtt                              40

<210> SEQ ID NO 484
<211> LENGTH: 40
<212> TYPE: DNA
<213> ORGANISM: Artificial
<220> FEATURE:
<223> OTHER INFORMATION: DNA Aptamer

<400> SEQUENCE: 484
gcactatttt tgacgtaact cttccaatat aaaatctgct                              40

<210> SEQ ID NO 485
<211> LENGTH: 40
<212> TYPE: DNA
<213> ORGANISM: Artificial
<220> FEATURE:
<223> OTHER INFORMATION: DNA Aptamer

<400> SEQUENCE: 485
aggcgttaac tcttgtcatg ttatagacgt ctaatccatc                              40

<210> SEQ ID NO 486
<211> LENGTH: 39
<212> TYPE: DNA
<213> ORGANISM: Artificial
<220> FEATURE:
<223> OTHER INFORMATION: DNA Aptamer

<400> SEQUENCE: 486
atagatttta tttttttta attcaaattc gctacagaa                                39

<210> SEQ ID NO 487
<211> LENGTH: 40
<212> TYPE: DNA
<213> ORGANISM: Artificial
<220> FEATURE:
<223> OTHER INFORMATION: DNA Aptamer

<400> SEQUENCE: 487
cgttagcgtc gtttatactg caagtacaaa cttgtaattg                              40

<210> SEQ ID NO 488
<211> LENGTH: 40
<212> TYPE: DNA
<213> ORGANISM: Artificial
<220> FEATURE:
<223> OTHER INFORMATION: DNA Aptamer

<400> SEQUENCE: 488
atggaatatc agccatcgtg aattgctcag actcgaaacg                              40
```

<210> SEQ ID NO 489
<211> LENGTH: 40
<212> TYPE: DNA
<213> ORGANISM: Artificial
<220> FEATURE:
<223> OTHER INFORMATION: DNA Aptamer

<400> SEQUENCE: 489
actgtaatca cttctttaa atagtcccgg aacgatatca                              40

<210> SEQ ID NO 490
<211> LENGTH: 40
<212> TYPE: DNA
<213> ORGANISM: Artificial
<220> FEATURE:
<223> OTHER INFORMATION: DNA Aptamer

<400> SEQUENCE: 490
cttgatccat actataactt aacatttgtt catctcaagt                              40

<210> SEQ ID NO 491
<211> LENGTH: 40
<212> TYPE: DNA
<213> ORGANISM: Artificial
<220> FEATURE:
<223> OTHER INFORMATION: DNA Aptamer

<400> SEQUENCE: 491
agtttttgaa atgcattaca gtataaacat ttcacacatc                              40

<210> SEQ ID NO 492
<211> LENGTH: 40
<212> TYPE: DNA
<213> ORGANISM: Artificial
<220> FEATURE:
<223> OTHER INFORMATION: DNA Aptamer

<400> SEQUENCE: 492
ctaaatcgcg aaccgagttt ttgtcaaagt tctagattaa                              40

<210> SEQ ID NO 493
<211> LENGTH: 40
<212> TYPE: DNA
<213> ORGANISM: Artificial
<220> FEATURE:
<223> OTHER INFORMATION: DNA Aptamer

<400> SEQUENCE: 493
atttgagaag tttgactgca gtcgcacact cccattttg                               40

<210> SEQ ID NO 494
<211> LENGTH: 40
<212> TYPE: DNA
<213> ORGANISM: Artificial
<220> FEATURE:
<223> OTHER INFORMATION: DNA Aptamer

<400> SEQUENCE: 494
atgtgtatcg atatggccta acctagcttt agaactggtc                              40

<210> SEQ ID NO 495
<211> LENGTH: 38
<212> TYPE: DNA
<213> ORGANISM: Artificial
<220> FEATURE:

<223> OTHER INFORMATION: DNA Aptamer

<400> SEQUENCE: 495
attacttaaa gatttgtcat ctctttaaag ctttgtta                              38

<210> SEQ ID NO 496
<211> LENGTH: 38
<212> TYPE: DNA
<213> ORGANISM: Artificial
<220> FEATURE:
<223> OTHER INFORMATION: DNA Aptamer

<400> SEQUENCE: 496
ccaaaaatag tgatcacatt ttgtgttcga taataact                              38

<210> SEQ ID NO 497
<211> LENGTH: 40
<212> TYPE: DNA
<213> ORGANISM: Artificial
<220> FEATURE:
<223> OTHER INFORMATION: DNA Aptamer

<400> SEQUENCE: 497
acgaactttt ttaattcgca gacatgttta tagtttcttg                            40

<210> SEQ ID NO 498
<211> LENGTH: 40
<212> TYPE: DNA
<213> ORGANISM: Artificial
<220> FEATURE:
<223> OTHER INFORMATION: DNA Aptamer

<400> SEQUENCE: 498
acgaactttt ttaattcgca gacatgttta tagtttcttg                            40

<210> SEQ ID NO 499
<211> LENGTH: 40
<212> TYPE: DNA
<213> ORGANISM: Artificial
<220> FEATURE:
<223> OTHER INFORMATION: DNA Aptamer

<400> SEQUENCE: 499
ataggaaggg attcagcacg ggctgtcgta gacttcaagc                            40

<210> SEQ ID NO 500
<211> LENGTH: 39
<212> TYPE: DNA
<213> ORGANISM: Artificial
<220> FEATURE:
<223> OTHER INFORMATION: DNA Aptamer

<400> SEQUENCE: 500
agggtccgct agacgtaggg gagagccaga aatctcaac                             39

<210> SEQ ID NO 501
<211> LENGTH: 40
<212> TYPE: DNA
<213> ORGANISM: Artificial
<220> FEATURE:
<223> OTHER INFORMATION: DNA Aptamer

<400> SEQUENCE: 501
cataccaagt agagaccata ctctcagagg actggacgcg                            40

<210> SEQ ID NO 502
<211> LENGTH: 40
<212> TYPE: DNA
<213> ORGANISM: Artificial
<220> FEATURE:
<223> OTHER INFORMATION: DNA Aptamer

<400> SEQUENCE: 502
ttttcattgc tacaaagtca ttttgtaggt aacggtggat            40

<210> SEQ ID NO 503
<211> LENGTH: 39
<212> TYPE: DNA
<213> ORGANISM: Artificial
<220> FEATURE:
<223> OTHER INFORMATION: DNA Aptamer

<400> SEQUENCE: 503
agggtcgttg gggccagggt tcacgcgccg ctccccgct             39

<210> SEQ ID NO 504
<211> LENGTH: 40
<212> TYPE: DNA
<213> ORGANISM: Artificial
<220> FEATURE:
<223> OTHER INFORMATION: DNA Aptamer

<400> SEQUENCE: 504
gtgataggga agtgagtgct ggcccgtagc gaccctggaa            40

<210> SEQ ID NO 505
<211> LENGTH: 40
<212> TYPE: DNA
<213> ORGANISM: Artificial
<220> FEATURE:
<223> OTHER INFORMATION: DNA Aptamer

<400> SEQUENCE: 505
gtgataggga agtgagtgct ggcccgtagc gaccctggaa            40

<210> SEQ ID NO 506
<211> LENGTH: 40
<212> TYPE: DNA
<213> ORGANISM: Artificial
<220> FEATURE:
<223> OTHER INFORMATION: DNA Aptamer

<400> SEQUENCE: 506
ggcgcgctgg cgcgcgaagg tggctcggag tgctccgggc            40

<210> SEQ ID NO 507
<211> LENGTH: 40
<212> TYPE: DNA
<213> ORGANISM: Artificial
<220> FEATURE:
<223> OTHER INFORMATION: DNA Aptamer

<400> SEQUENCE: 507
caagagtgtt agacattatc tcagcgctgc caattatatt           40

<210> SEQ ID NO 508
<211> LENGTH: 42
<212> TYPE: DNA
<213> ORGANISM: Artificial
<220> FEATURE:
<223> OTHER INFORMATION: DNA Aptamer

<400> SEQUENCE: 508
agacttgaaa gcatctttac ttcgattggt aatattttg at    42

<210> SEQ ID NO 509
<211> LENGTH: 42
<212> TYPE: DNA
<213> ORGANISM: Artificial
<220> FEATURE:
<223> OTHER INFORMATION: DNA Aptamer

<400> SEQUENCE: 509
ttgaaattca atcgcttaag tcccgtttat aggaataacg at    42

<210> SEQ ID NO 510
<211> LENGTH: 40
<212> TYPE: DNA
<213> ORGANISM: Artificial
<220> FEATURE:
<223> OTHER INFORMATION: DNA Aptamer

<400> SEQUENCE: 510
tggcctaatc tcggagactg gccgctgtgg gcgcgggcct    40

<210> SEQ ID NO 511
<211> LENGTH: 39
<212> TYPE: DNA
<213> ORGANISM: Artificial
<220> FEATURE:
<223> OTHER INFORMATION: DNA Aptamer

<400> SEQUENCE: 511
ttttatttcg tatcctatat tttcaagtta gcttgactc    39

<210> SEQ ID NO 512
<211> LENGTH: 39
<212> TYPE: DNA
<213> ORGANISM: Artificial
<220> FEATURE:
<223> OTHER INFORMATION: DNA Aptamer

<400> SEQUENCE: 512
ttttatttcg tatcctatat tttcaagtta gcttgactc    39

<210> SEQ ID NO 513
<211> LENGTH: 40
<212> TYPE: DNA
<213> ORGANISM: Artificial
<220> FEATURE:
<223> OTHER INFORMATION: DNA Aptamer

<400> SEQUENCE: 513
ttgaaggcgt accgtccgcg ggcggcgtgt gcgccgggcc    40

<210> SEQ ID NO 514
<211> LENGTH: 39
<212> TYPE: DNA
<213> ORGANISM: Artificial
<220> FEATURE:
<223> OTHER INFORMATION: DNA Aptamer

<400> SEQUENCE: 514
ctcttaatgt cacggctgag cctatgctgg cgtgaccga    39

<210> SEQ ID NO 515
<211> LENGTH: 40

```
<212> TYPE: DNA
<213> ORGANISM: Artificial
<220> FEATURE:
<223> OTHER INFORMATION: DNA Aptamer

<400> SEQUENCE: 515
gtgtgaaagc tgggagagtc tgcgggcctg tgtcgcgcaa                              40

<210> SEQ ID NO 516
<211> LENGTH: 40
<212> TYPE: DNA
<213> ORGANISM: Artificial
<220> FEATURE:
<223> OTHER INFORMATION: DNA Aptamer

<400> SEQUENCE: 516
atgggtgtgt ctgggtagac gttgttttgg cctggtgtta                              40

<210> SEQ ID NO 517
<211> LENGTH: 40
<212> TYPE: DNA
<213> ORGANISM: Artificial
<220> FEATURE:
<223> OTHER INFORMATION: DNA Aptamer

<400> SEQUENCE: 517
gtgtgaaagc tgggagagtc tgcgggcctg tgtcgcgcaa                              40

<210> SEQ ID NO 518
<211> LENGTH: 40
<212> TYPE: DNA
<213> ORGANISM: Artificial
<220> FEATURE:
<223> OTHER INFORMATION: DNA Aptamer

<400> SEQUENCE: 518
atgggtgtgt ctgggtagac gttgttttgg cctggtgtta                              40

<210> SEQ ID NO 519
<211> LENGTH: 35
<212> TYPE: DNA
<213> ORGANISM: Artificial
<220> FEATURE:
<223> OTHER INFORMATION: DNA Aptamer

<400> SEQUENCE: 519
cgtaagaggg agattcctac aaacgctccc catcc                                   35

<210> SEQ ID NO 520
<211> LENGTH: 40
<212> TYPE: DNA
<213> ORGANISM: Artificial
<220> FEATURE:
<223> OTHER INFORMATION: DNA Aptamer

<400> SEQUENCE: 520
cccgcaatcc acgacacaga cgactgccgt ggaccaccga                              40

<210> SEQ ID NO 521
<211> LENGTH: 38
<212> TYPE: DNA
<213> ORGANISM: Artificial
<220> FEATURE:
<223> OTHER INFORMATION: DNA Aptamer

<400> SEQUENCE: 521
```

```
cgtaggaggg agttccaatg atacatccta accgatac                                  38

<210> SEQ ID NO 522
<211> LENGTH: 40
<212> TYPE: DNA
<213> ORGANISM: Artificial
<220> FEATURE:
<223> OTHER INFORMATION: DNA Aptamer

<400> SEQUENCE: 522
gcggggggtt gtgcccgta aaggcttgcc aagcgccgca                                 40

<210> SEQ ID NO 523
<211> LENGTH: 40
<212> TYPE: DNA
<213> ORGANISM: Artificial
<220> FEATURE:
<223> OTHER INFORMATION: DNA Aptamer

<400> SEQUENCE: 523
ggtcaggtac agaagactgg tgtatgaaga tgcctgctac                                40

<210> SEQ ID NO 524
<211> LENGTH: 40
<212> TYPE: DNA
<213> ORGANISM: Artificial
<220> FEATURE:
<223> OTHER INFORMATION: DNA Aptamer

<400> SEQUENCE: 524
ctaatgatgg ttttcgcaat taacgccatc gaacaagatc                                40

<210> SEQ ID NO 525
<211> LENGTH: 32
<212> TYPE: DNA
<213> ORGANISM: Artificial
<220> FEATURE:
<223> OTHER INFORMATION: DNA Aptamer

<400> SEQUENCE: 525
ccgcgcagat atacaacgta cctctgtgcg ca                                        32

<210> SEQ ID NO 526
<211> LENGTH: 32
<212> TYPE: DNA
<213> ORGANISM: Artificial
<220> FEATURE:
<223> OTHER INFORMATION: DNA Aptamer

<400> SEQUENCE: 526
ctgtgaggcg tactgcggtg agcctctcat ta                                        32

<210> SEQ ID NO 527
<211> LENGTH: 32
<212> TYPE: DNA
<213> ORGANISM: Artificial
<220> FEATURE:
<223> OTHER INFORMATION: DNA Aptamer

<400> SEQUENCE: 527
ccccccgaat cacatgactt gggcgggggt cg                                        32

<210> SEQ ID NO 528
<211> LENGTH: 32
<212> TYPE: DNA
<213> ORGANISM: Artificial
```

```
<220> FEATURE:
<223> OTHER INFORMATION: DNA Aptamer

<400> SEQUENCE: 528
ggccgcgcat tctctgccgg ctggtgtacg gt                          32

<210> SEQ ID NO 529
<211> LENGTH: 32
<212> TYPE: DNA
<213> ORGANISM: Artificial
<220> FEATURE:
<223> OTHER INFORMATION: DNA Aptamer

<400> SEQUENCE: 529
tgacggccat acgttcatcg tatgtagtct tc                          32

<210> SEQ ID NO 530
<211> LENGTH: 32
<212> TYPE: DNA
<213> ORGANISM: Artificial
<220> FEATURE:
<223> OTHER INFORMATION: DNA Aptamer

<400> SEQUENCE: 530
ggcgcagggg ggggcccaga gtatggggcc tg                          32

<210> SEQ ID NO 531
<211> LENGTH: 31
<212> TYPE: DNA
<213> ORGANISM: Artificial
<220> FEATURE:
<223> OTHER INFORMATION: DNA Aptamer

<400> SEQUENCE: 531
cgaggggcgt gggcttcggg cacccagcgg g                           31

<210> SEQ ID NO 532
<211> LENGTH: 32
<212> TYPE: DNA
<213> ORGANISM: Artificial
<220> FEATURE:
<223> OTHER INFORMATION: DNA Aptamer

<400> SEQUENCE: 532
atggctcggg tcttacaccc tggaggaccg tg                          32

<210> SEQ ID NO 533
<211> LENGTH: 32
<212> TYPE: DNA
<213> ORGANISM: Artificial
<220> FEATURE:
<223> OTHER INFORMATION: DNA Aptamer

<400> SEQUENCE: 533
ggggcgggca ctgccttcga gttgctcggt gt                          32

<210> SEQ ID NO 534
<211> LENGTH: 32
<212> TYPE: DNA
<213> ORGANISM: Artificial
<220> FEATURE:
<223> OTHER INFORMATION: DNA Aptamer

<400> SEQUENCE: 534
cgcatgggta ccagtgagcg atggaccctg gc                          32
```

<210> SEQ ID NO 535
<211> LENGTH: 32
<212> TYPE: DNA
<213> ORGANISM: Artificial
<220> FEATURE:
<223> OTHER INFORMATION: DNA Aptamer

<400> SEQUENCE: 535
cgcagtgtcg taccgtcgat gcggggatgc cg                          32

<210> SEQ ID NO 536
<211> LENGTH: 32
<212> TYPE: DNA
<213> ORGANISM: Artificial
<220> FEATURE:
<223> OTHER INFORMATION: DNA Aptamer

<400> SEQUENCE: 536
cgcagaaggc gtcggataga cccgcaatca cg                          32

<210> SEQ ID NO 537
<211> LENGTH: 40
<212> TYPE: DNA
<213> ORGANISM: Artificial
<220> FEATURE:
<223> OTHER INFORMATION: DNA Aptamer

<400> SEQUENCE: 537
gcggtgaact gctcgtaaag cggggcaaga ccagagggat                  40

<210> SEQ ID NO 538
<211> LENGTH: 41
<212> TYPE: DNA
<213> ORGANISM: Artificial
<220> FEATURE:
<223> OTHER INFORMATION: DNA Aptamer

<400> SEQUENCE: 538
atgcgattgt ctcctaatta tcactcgctt actgggtcaa t                41

<210> SEQ ID NO 539
<211> LENGTH: 49
<212> TYPE: DNA
<213> ORGANISM: Artificial
<220> FEATURE:
<223> OTHER INFORMATION: DNA Aptamer

<400> SEQUENCE: 539
ccgatgtagg agtgaggttg ggcagcgggc ccagccgagg cactccccg        49

<210> SEQ ID NO 540
<211> LENGTH: 40
<212> TYPE: DNA
<213> ORGANISM: Artificial
<220> FEATURE:
<223> OTHER INFORMATION: DNA Aptamer
<220> FEATURE:
<221> NAME/KEY: misc_feature
<222> LOCATION: (30)..(30)
<223> OTHER INFORMATION: n is a, c, g, or t

<400> SEQUENCE: 540
gtatcaagct ttagtggaga gtaccactcn cactaaaaca                  40

<210> SEQ ID NO 541
<211> LENGTH: 40

-continued

```
<212> TYPE: DNA
<213> ORGANISM: Artificial
<220> FEATURE:
<223> OTHER INFORMATION: DNA Aptamer

<400> SEQUENCE: 541
cctacagtat agatgagtcg accattagaa acaatggtcc                               40

<210> SEQ ID NO 542
<211> LENGTH: 32
<212> TYPE: DNA
<213> ORGANISM: Artificial
<220> FEATURE:
<223> OTHER INFORMATION: DNA Aptamer

<400> SEQUENCE: 542
gccgtccccg cgtttggtac gcggtaggag ac                                      32

<210> SEQ ID NO 543
<211> LENGTH: 32
<212> TYPE: DNA
<213> ORGANISM: Artificial
<220> FEATURE:
<223> OTHER INFORMATION: DNA Aptamer

<400> SEQUENCE: 543
ggcgcttagt tagactaacg ttgctagggg cg                                      32

<210> SEQ ID NO 544
<211> LENGTH: 39
<212> TYPE: DNA
<213> ORGANISM: Artificial
<220> FEATURE:
<223> OTHER INFORMATION: DNA Aptamer

<400> SEQUENCE: 544
ctcgatcagt acacagatcg cctaatggag attttttca                               39

<210> SEQ ID NO 545
<211> LENGTH: 40
<212> TYPE: DNA
<213> ORGANISM: Artificial
<220> FEATURE:
<223> OTHER INFORMATION: DNA Aptamer

<400> SEQUENCE: 545
cactggggtc ggagatttct cgttgtggcg gccgccggcg                              40

<210> SEQ ID NO 546
<211> LENGTH: 40
<212> TYPE: DNA
<213> ORGANISM: Artificial
<220> FEATURE:
<223> OTHER INFORMATION: DNA Aptamer

<400> SEQUENCE: 546
attaatatct aactagcgcg ctcgtctcaa tatcggcaag                              40

<210> SEQ ID NO 547
<211> LENGTH: 40
<212> TYPE: DNA
<213> ORGANISM: Artificial
<220> FEATURE:
<223> OTHER INFORMATION: DNA Aptamer
```

```
<400> SEQUENCE: 547
gtttgtgtat tacagttatg ttaccctcat ttttctgaac                    40
```

FUNCTIONAL LIGANDS TO TARGET MOLECULES

CROSS-REFERENCE TO RELATED APPLICATIONS

This application is a continuation-in-part of U.S. utility patent application Ser. No. 13/493,996, filed Jun. 11, 2012, entitled "FUNCTIONAL LIGANDS TO TARGET MOLECULES", which is still pending, which is a non-provisional of U.S. provisional patent application Ser. No. 61/495,976, entitled "FUNCTIONAL LIGANDS TO TARGET MOLECULES", filed Jun. 11, 2011, and is a continuation-in-part of U.S. utility patent application Ser. No. 12/683,429, filed Jan. 7, 2010, entitled "METHODS FOR SIMULTANEOUS GENERATION OF FUNCTIONAL LIGANDS", which issued as U.S. Pat. No. 8,314,052 on Nov. 20, 2012, which claims the benefit of U.S. provisional patent application Ser. No. 61/162,394, filed Mar. 23, 2009, entitled "METHODS FOR SIMULTANEOUS GENERATION OF FUNCTIONAL LIGANDS", and U.S. Pat. No. 8,034,569, filed Jun. 6, 2009, entitled "METHODS FOR MOLECULAR DETECTION", which claims the benefit of U.S. provisional patent application Ser. No. 61/059,435, filed Jun. 6, 2008, entitled "METHODS FOR MOLECULAR DETECTION", the contents of all of which are hereby incorporated by reference in their entireties.

SEQUENCE LISTING

Deoxyribonucleic acid sequences are included in the ASCII text file entitled "PSEQ1_P1011US05.txt", created May 28, 2013, of 96 kilobytes in size, which is hereby incorporated by reference in its entirety.

FIELD OF THE INVENTION

This invention relates to functional ligands to target molecules, particularly to functional nucleic acids and modifications thereof and methods for generating functional ligands, particularly to methods for generating multiple functional nucleic acids against multiple different target molecules simultaneously.

BACKGROUND OF THE INVENTION

Aptamers, which are nucleic acid ligands capable of binding to molecular targets, have recently attracted increased attention for their potential application in many areas of biology and biotechnology. They may be used as sensors, therapeutic tools, to regulate cellular processes, as well as to guide drugs to their specific cellular target(s). Contrary to the actual genetic material, their specificity and characteristics are not directly determined by their primary sequence, but instead by their tertiary structure. Aptamers have been recently investigated as immobilized capture elements in a microarray format. Others have recently selected aptamers against whole cells and complex biological mixtures.

Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Once multiple rounds (typically 10-15) of SELEX are completed, the nucleic acid sequences are identified by conventional cloning and sequencing. Aptamers have most famously been developed as ligands to important proteins, rivaling antibodies in both affinity and specificity, and the first aptamer-based therapeutics are now emerging. More recently, however, aptamers have been also developed to bind small organic molecules and cellular toxins, viruses, and even targets as small as heavy metal ions.

SUMMARY OF THE INVENTION

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules. The present invention further relates to methods for generating, for example, functional biomolecules, particularly to functional nucleic acids, that bind with functional activity to another biomolecule, such as a receptor molecule. More than one or multiple targets as used herein may generally include different types of targets, and/or may also include a multitude of a singular type of targets at different conditions, such as, for example, temperature, pH, chemical environment, and/or any other appropriate conditions.

In general, a method for generating functional biomolecules includes obtaining a library, such as a diverse or randomized library, for example, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. The method for generating functional biomolecules further includes contacting the library of biomolecules with more than one target, such as, for example, a molecular target, material and/or substance. In general, the members of the library that do not bind with some affinity to the more than one target may be washed or otherwise partitioned from the remainder of the library, which may have a given level of binding affinity to the more than one target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity, such biomolecules generally referred to as aptamers or ligands.

In one exemplary aspect of the invention, generation of functional biomolecules may be performed against more than one or multiple targets simultaneously within a single system, such as the generation of functional nucleic acid ligands within a single reaction volume. In general, more than one or a plurality of targets may be disposed within in a single reaction volume, and a library of biomolecules, such as a nucleic acid library, may be applied to the reaction volume. The members of the library that do not bind to any of the plurality of targets under given conditions may then be partitioned, such as by washing. One or more rounds of binding and partitioning of the members of the library may be performed, such as, for example, to obtain a remainder of members of the library with a given affinity for their targets. The remaining members that bind to the plurality of targets of the library may then be marked and/or tagged, such as to identify the particular target or targets to which the member(s) of the library binds. The binding members of the library may then be isolated and, by virtue of the marking or tagging, be matched to a particular target or targets. This is desirable as high capacity, multiplexed identification procedures may save time, expense, and physical space for the process over single target identification processes. The present method may also be desirable as it may be utilized to identify and/or eliminate biomolecules that bind or have a tendency to bind to multiple targets.

In an exemplary embodiment, a plurality of target molecules are affixed to a substrate within a single reaction volume, such as, for example, by attaching the targets to a substrate of an array. It may generally be appreciated that a single reaction volume may refer to or include multiple reaction sub-volumes, such as, for example, discrete or semi-discrete fluid droplets. In general, the targets may be disposed with multiple copies of each target in clusters or "spots" such that a given array may have an ordered deposition of targets on the substrate, with each target identifiable by the location of a particular spot on the substrate. A library of nucleic acids may then be contacted or applied to the array and the non-binding members of the library may be partitioned or washed off the array. The binding and washing steps may be repeated and may also utilize an amplification step to generate additional copies of any remaining binding members of the library. The array may then be marked or tagged with a plurality of identifiers, such as, for example, a plurality of oligonucleotides which may universally bind through Watson-Crick interactions to the members of the library of nucleic acids. The marking or tagging may be, for example, accomplished by manually applying identifiers, such as by pipetting or the like, utilizing microcontact pins, applying membranes/films with identifiers, printing, for example, inkjet printing, and/or other similar tagging methods, of identifier containing solutions to the array. The identifiers may further include a unique or semi-unique sequence which may be utilized to correspond to the spots and thus the targets of the array. For example, a unique or semi-unique identifier sequence may be utilized that identifies each spatial location on an array, such as each particular target spot. The identifier may then be associated with and/or attached to the nucleic acid members bound to a particular spot. Thus, the nucleic acids, for example, bound to a particular target spot may be identified by the sequence of the associated identifier. In some embodiments, the identifiers may further be primers and may be utilized with a nucleic acid amplification reaction on the array to generate additional copies of the bound nucleic acids. The unique or semi-unique identifier sequence may also be incorporated into the members of the library amplified. This may be desirable for associating a given member with a target or targets while preserving the particular sequence of the member as the locational identifying sequence is appended to the sequence of the library member. This may be particularly desirable for resolving multiple binders to a single target or members of the library that bind to multiple targets.

In general, the starting library of biomolecules, such as nucleic acids, may be the product of at least one round of a previous SELEX protocol. For example, at least one round of SELEX may be performed with a library of biomolecules against multiple targets, such as, for example, in a solution. The targets in the solution may be substantially identical to the targets disposed on an array. This may be desirable as multiple rounds of selection may be performed with a library prior to applying the remaining members to an array for marking/tagging. Complex target arrays may generally be more expensive and/or difficult to make or utilize than solutions of target molecules, so performing only the final binding and marking/tagging procedure on the array may be desirable.

In other embodiments, identifiers may be predisposed on the array substrate in substantial proximity to the spots such that they may bind to, for example, nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the target spot.

In still other embodiments, identifiers may be disposed and/or synthesized on a separate substrate, such as a membrane, in a spatial disposition that substantially matches the spatial disposition of spots on the array, i.e. the identifiers may be arranged such that they may be readily superimposed onto the target spots on the array. The identifier substrate may then be contacted with the array with locational matching of the spots with identifiers. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof. The separate substrate may also be soluble, erodible, substantially permeable to the identifiers, and/or otherwise adapted for facilitating migration of the identifiers to the array.

In yet still other embodiments, the array substrate may be physically divided and/or partitioned for separate collection of the, for example, nucleic acids bound to the spots. The spots may, for example, also be controllably removable from the substrate such that they may be individually recovered and sorted.

In still yet other embodiments, identifiers may be disposed and/or synthesized on a separate substrate, such as a membrane, in a spatial disposition that substantially matches the spatial disposition of spots on the array, i.e. the identifiers may be arranged such that may be readily superimposed onto the target spots on the array. The separate substrate may be kept separately while the array substrate maybe physically divided and/or partitioned for separate collection of the nucleic acids bound to the spots. In this manner, the location of the different nucleic acids maybe maintained even when the array substrate is no longer intact, if the locations are of value. The identifiers may also be selectively applied to particular locations on the array and/or applied in a particular order or in groups.

In some embodiments, identifiers may only be applied to spots with bound nucleic acids. The spots with bound nucleic acids may be detected, for example, by detecting the presence of nucleic acids, such as by applying nucleic acid binding dyes, such as SYBR dyes, ethidium bromide and/or other appropriate dyes. The members of the nucleic acid library may also include detectable portions, such as, for example, fluorescent moieties, radioactive tags and/or other appropriate detectable portions.

In some embodiments, the identifiers may be applied to the bound nucleic acids together with other materials, such as for example, components of a nucleic acid amplification reaction, a nucleic acid ligation reaction, photo-linking reagents, and/or any other appropriate material, such as those materials that may facilitate attachment or association of the identifiers to the bound nucleic acids.

In yet another embodiment, identifiers may be ligated to the, for example, bound nucleic acids. For example, a nucleic acid ligase may be utilized to covalently link an identifier sequence to the bound nucleic acid. Further nucleic acid fragments may be utilized to facilitate ligase action, such as appropriate complementary fragments that may aid the formation of a substantially double-stranded nucleic acid complex compatible with a ligase. For another example, photo-ligation may be used to attach the identifiers to the, for example, bound nucleic acids. Photo-ligation may be especially useful when certain substrates are used. For example, macro-porous substrates.

In general, methods may be applied that may facilitate binding or other interactions between the identifiers and the, for example, nucleic acids bound to the spots. For example, the temperature may be increased to dissociate the nucleic acids from the spots. The temperature may subsequently be lowered such that, for example, base pairing may occur between the nucleic acids and the identifiers. Further in general, it may be desirable to apply the identifiers in a manner that physically separates and/or isolates the individual target spots such that cross-marking due to identifier diffusion/migration may be minimized. For example, the identifiers may be applied in individual fluid droplets such that there is no continuous fluid contact between individual identifier containing fluids. For further example, the substrate of the array may be absorbent and/or porous such that the identifiers may be absorbed into the substrate material. The substrate material may also block lateral diffusion while allowing vertical diffusion, such that identifiers may be applied and absorbed into the substrate while minimizing diffusion across the plane of the substrate, such as to other target spots.

In a further embodiment, a method for generating functional biomolecules includes obtaining a library of peptide sequences and contacting the library with a plurality of targets. In some exemplary embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

Other methods of peptide selection may include, but are not limited to, mRNA display, ribosome display, and/or any other appropriate peptide display method or combination thereof.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration×time, analysis measures the annealing time of particular oligonucleotides while in solution with other nucleic acids, such as the members of the library of biomolecules. In general, the annealing time will be faster the lower the diversity of the library.

The present invention together with the above and other advantages may best be understood from the following detailed description of the embodiments of the invention illustrated in the drawings.

BRIEF DESCRIPTION OF THE FIGURES

FIGS. 6, 6a, 6b and 6c illustrate embodiments of identifiers and ligation of identifiers to a library member;

FIGS. 7 and 7a illustrate phage display for a target;

FIG. 7b illustrates an mRNA display fusion product;

FIG. 7c illustrates a ribosome display fusion product; and

DETAILED DESCRIPTION OF THE INVENTION

Figure 1:
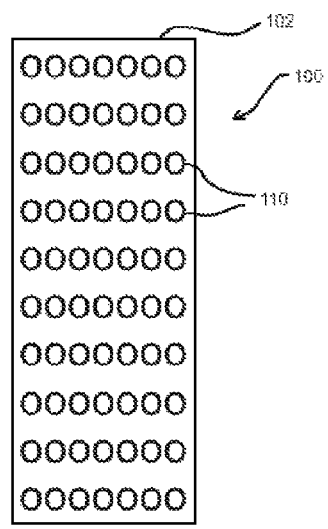
FIG. 1 illustrates an embodiment of a multiple target array.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules. The present invention further relates to methods for simultaneously generating different functional biomolecules, particularly to functional nucleic acids, that bind with functional activity to another biomolecule, such as a receptor molecule.

In general, a method for generating functional biomolecules includes obtaining a library, such as a diverse or randomized library, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. The method for generating functional biomolecules further includes contacting the library of biomolecules with at least one target, such as, for example, a molecular target, material and/or substance. In general, the members of the library that do not bind with some affinity to the target may be washed or otherwise partitioned from the remainder of the library, which may have a given level of binding affinity to the target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity. The basic SELEX protocol and aptamers are described in U.S. Pat. No. 5,270,163, entitled "Methods for identifying nucleic acid ligands," the entire contents of which are hereby incorporated by reference.

In one exemplary aspect of the invention, generation of functional biomolecules may be performed against multiple targets simultaneously within a single system, such as the generation of functional nucleic acid ligands within a single reaction volume. In general, a plurality of targets may be disposed within in a single reaction volume and a library of biomolecules, such as a nucleic acid library, may be applied to the reaction volume. The targets may be, for example, proteins, cells, small molecules, biomolecules, and/or combinations or portions thereof. The members of the library that do not bind to any of the plurality of targets under given conditions may then be partitioned, such as by washing. The remaining members of the library may then be marked and/or tagged, such as to identify the particular target or targets to which the member of the library binds. The binding members of the library may then be isolated and, by virtue of the marking or tagging, be matched to a particular target or targets. This may be desirable as high capacity, multiplexed identification procedures may save time, expense, and physical space for the process over single target identification processes. The present method may also be desirable as it may be utilized to identify and/or eliminate molecules that bind to multiple targets.

Figure 2:
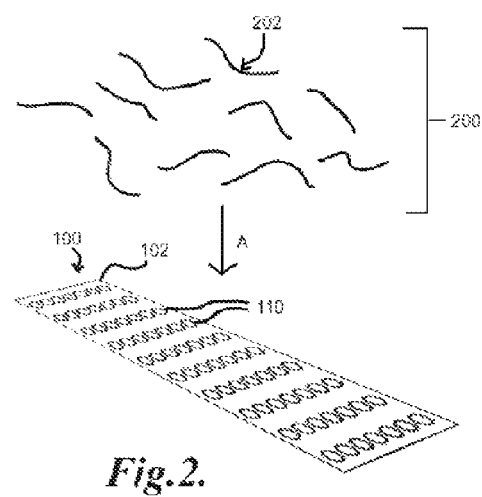
FIG. 2 illustrates the application of a library of biomolecules to a target array.
Figure 2A:
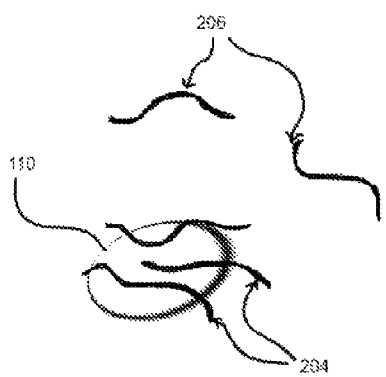
FIG. 2a illustrates the binding of members of a library of biomolecules to a target spot.
Figure 3:
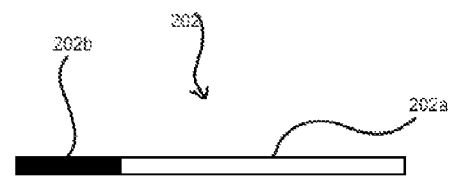
FIGS. 3 and 3a illustrate embodiments of biomolecule library members.
Figure 3A:
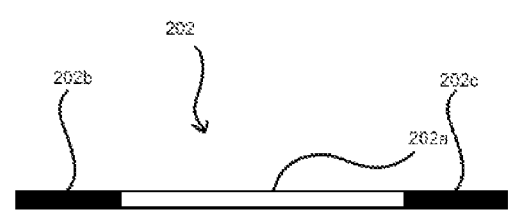
Figure 3B:
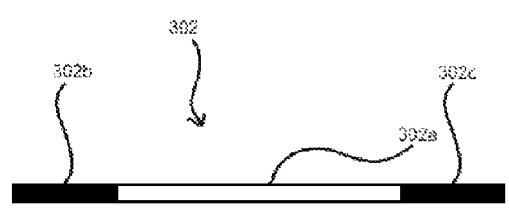
FIG. 3b illustrates an embodiment of an identifier.
Figure 4:
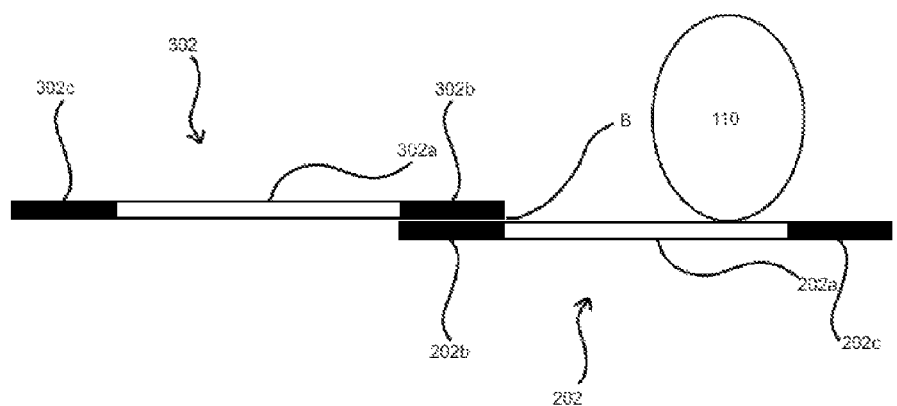
FIG. 4 illustrates the tagging of a library member bound to target with an identifier.
Figure 4A:
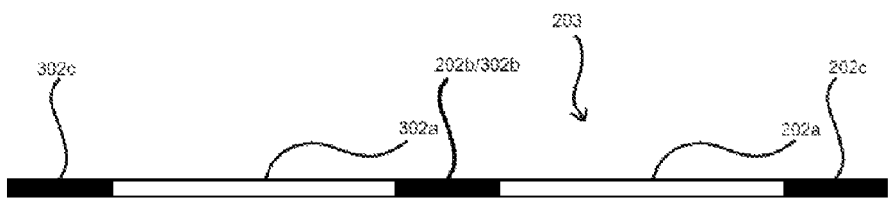
FIG. 4a illustrates a tagged library member product.

In an exemplary embodiment, a plurality of target molecules are affixed to a substrate within a single reaction volume, such as, for example, by attaching the targets to a substrate of an array. As illustrated in FIG. 1, the targets may be disposed with multiple copies of each target, such as target molecules, in clusters or "spots" 110 on the substrate 102 of an array 100 such that a given array 100 may have an ordered deposition of targets on the substrate 102, with each target identifiable by the location of a particular spot 110 on the substrate 102. Each spot 110 may be a unique target or there may be multiple spots 110 of at least one target on a given array 100. In general, high content target arrays, such as high content protein or antibody arrays, may be utilized. A library 200 of, for example, nucleic acids 202 may then be applied A to array 100, as illustrated in FIG. 2. Particular members 204 of the library 200 may then bind to target spots 110, such as illustrated in FIG. 2a. The non-binding members 206 of the library 200 may be partitioned or washed off the array 100. The binding and washing steps may be repeated and may also utilize an amplification step to generate additional copies of any remaining binding members 204 of the library 200. The array 100 may then be marked or tagged with a plurality of identifiers, such as, for example, a plurality of oligonucleotides which may universally bind through Watson-Crick interactions to the members of the library of, for example, nucleic acids. In one embodiment, each member 202 of the library 200 may include a potential binding sequence 202a and at least one conserved region 202b which may bind an identifier oligonucleotide, such as illustrated in FIG. 3. A further conserved region 202c may also be included to facilitate priming for amplification reactions, such as Polymerase Chain Reaction (PCR), as illustrated in FIG. 3a. In general the conserved regions 202b, 202c may flank the potential binding sequence 202a, such as to facilitate priming for amplification. An identifier 302 may then include a unique or semi-unique sequence 302a, such as illustrated in FIG. 3b, which may be utilized to correspond to the spots 110 and thus the targets of the array 100 by location of the a spot 110 on the substrate 102. The identifiers 302 may further include conserved region 302b which may bind to the conserved region 202b of the library members 202 by Watson-Crick base pairing. The identifiers 302 may also include a further conserved region 302c which may facilitate priming for amplification. The identifiers 302 may be, for example, applied to the spots 110 by printing, for example, inkjet printing, using micro-contact pins, and/or otherwise applying solutions containing identifiers 302 to the substrate 102 of the array 100, such as, for example, by pipetting or the like, onto the spots 110. A library member 202 bound to a target spot 110 may then be tagged with an identifier 302 via base pairing B at regions 202b, 302b, as illustrated in FIG. 4. Thus, the nucleic acids 202 bound to a particular target spot 110 may be identified by the sequence 302a of the identifier 302. In an exemplary embodiment, nucleic acid amplification, such as PCR, may be utilized to generate copies of the members 202 bound to the spots 110, incorporating the identifier sequence 302a (or more its complementary sequence) into the product 203, as illustrated in FIG. 4a. This may be desirable for associating a given member 202 with a target or targets 110 while preserving the particular sequence of the member 202. This may be particularly desirable for resolving multiple binders to a single target or members of the library that bind to multiple targets. Subsequent amplifications may utilize primers for the sequences 202c, 302c such that only the products 203 containing both the sequences 202a, 302a are amplified. It may be understood that references to nucleic acid sequences, such as above, may generally refer to either a particular sequence or the corresponding complementary nucleic acid sequence. In general, it may be desirable for single droplets and/or otherwise separated volumes of solutions containing identifiers 302 for each spot 110 on the array 100 such that the possibility of mistagging may be reduced.

In one aspect, the identifiers may be printed on all the targets. In another aspect, the identifiers may be printed only on targets with bound biomolecules.

Figure 8:
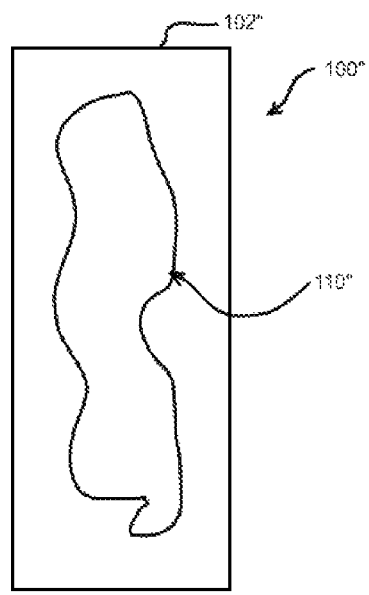
FIG. 8 illustrates an example of a histology section target.

In another embodiment, a histology section, such as the section 110" on substrate 102" of histology slide 100" in FIG. 8, may be utilized as a target set. The section 110" may be, for example, a tissue section, a cell mass, and/or any other appropriate biological sample which may generally have structurally significant features. As with the array 100, a library of biomolecules, such as nucleic acids, may be applied which may bind to specific locations on the section 110", the locations on which may, for example, represent separate targets to generate affinity binding nucleic acids. Identifiers may then be disposed on the slide 100" as described above, or as in the embodiments below, such that identifiers may be utilized to correspond to specific features of the section 110".

Figure 5:
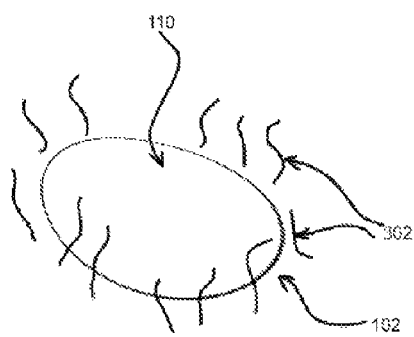
FIG. 5 illustrates a target spot with nearby identifiers on a substrate.

In other embodiments, identifiers may be predisposed on the array substrate in substantial proximity to the spots, such as illustrated with identifiers 302 disposed on substrate 102 in proximity to spot 110 in FIG. 5, such that they may bind to nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the spot.

Figure 5A:
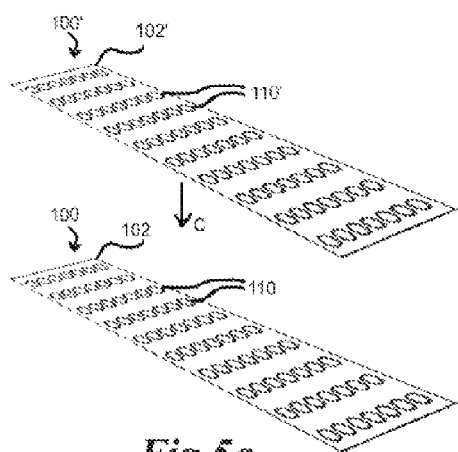
FIG. 5a illustrates the application of an identifier sheet to a target array.

In still other embodiments, identifiers may be disposed and/or synthesized on a separate substrate, such as a membrane, in a spatial disposition that matches the spatial disposition of spots on the array. FIG. 5a illustrates an example of an identifier sheet 100' with membrane 102' which may include identifier spots 110' which may substantially correspond to target spots 110 of the array 100. The identifier sheet 100' may then be contacted C with the array 100 with locational matching of the target spots 110 with identifier spots 110'. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof.

In some embodiments, the membrane may be soluble and/or substantially erodible. For example, the membrane may include a film forming and/or soluble material. Identifiers and/or other materials, such as components of a nucleic acid amplification or ligation reaction, may be included such that a film is formed containing the desired materials. The membrane may then be applied to the substrate and a suitable solvent, such as water or ethanol, may be utilized to dissolve and/or erode the film, which may then release the included materials, such as the identifiers, to the substrate. Suitable materials for the film may include hydrophilic materials including polysaccharides such as carrageenan, chondroitin sulfate, glucosamine, pullulan, soluble cellulose derivatives such as hydroxypropyl cellulose and hydroxymethyl cellulose, polyacrylic acid, polyvinyl alcohol, polyethylene glycol (PEG), polyethylene oxide (PEO), ethylene oxide-propylene oxide co-polymer, polyvinylpyrrolidone (PVP), polycaprolactone, polyorthoesters, polyphosphazene, polyvinyl acetate, and polyisobutylene.

The membrane may further be adapted to have a desirable rate of erosion and/or dissolution. The rate may be modified by the inclusion of hydrophobic and/or less soluble additives. Suitable materials may include, but are not limited to, those from the family of quaternary ammonium acrylate/methacrylate co-polymers, (Eudragit RS), cellulose and its lower solubility derivatives, such as butyl cellulose, hydroxybutyl cellulose and ethylhydroxyethyl cellulose, high molecular weight PEG or PEO or a combination thereof.

In yet still other embodiments, the array substrate may be physically divided and/or partitioned for separate collection of the nucleic acids bound to the spots. The spots may, for example, also be controllably removable from the substrate such that they may be individually recovered and sorted. The array itself may also be perforated and/or otherwise easily and/or conveniently partitionable.

In another embodiment, identifiers may be ligated to the bound nucleic acids. For example, a nucleic acid ligase may be utilized to covalently link an identifier sequence to the bound nucleic acid. In general, nucleic acid ligases are enzymes that covalently join two nucleic acids by catalyzing the formation of phosphodiester bonds at the ends of the phosphate backbone of the nucleic acids. Examples of appropriate nucleic acid ligases may include, but are not limited to, E. coli DNA ligase, T4 DNA ligase, T4 RNA ligase, strand break DNA repair enzymes, and/or any other appropriate ligase, modified enzyme, and/or a combination thereof. In general the ligase utilized may be selected based on the form of ligation performed, such as ligation of blunt ends, compatible overhang ("sticky") ends, single stranded DNA, singe stranded RNA and/or any other form of ligation. Further in general, the steps in ligating two nucleic acids together is a one step process that may be carried out at or near room temperature. Further nucleic acid fragments may be utilized to facilitate ligase action, such as appropriate complementary fragments that may aid the formation of a substantially double-stranded nucleic acid complex compatible with a ligase. In general, double stranded ligation may be employed and may utilize substantially compatible overhang fragments to facilitate ligation, or also blunt end ligation may be utilized, such as with either the nucleic acid end or the identifier having a phosphorylated end while the other is unphosphorylated for ligation. Single stranded ligation may also be employed.

Photo ligation may also be employed. Photo ligation may, for example, include covalently linking adjacent nucleic acids by application of electromagnetic energy, such as ultraviolet or visible light. Coupling agents may also be utilized to facilitate the formation of covalent linkages.

In some embodiments, dyes may be included into the identifiers. In one aspect, the identifiers may be doped with dyes. In another aspect, the identifier solutions may be mixed with dyes. According to one embodiment, the dyes may be photosensitive and may be fluorescent. According to another embodiment, the dyes maybe photosensitive and may be phosphorescent.

The substrates used may be glass, ceramic or polymeric, as long as their surfaces promote adhesion between the substrates and the targets. Polymers may include synthetic polymers as well as purified biological polymers. The substrate may also be any film, which may be non-porous or macroporous.

The substrate may be generally planar and may be of any appropriate geometry such as, for example, rectangular, square, circular, elliptical, triangular, other polygonal shape, irregular and/or any other appropriate geometry. The substrate may also be of other forms, such as cylindrical, spherical, irregular and/or any other appropriate form.

Appropriate ceramics may include, for example, hydroxyapatite, alumina, graphite and pyrolytic carbon.

Appropriate synthetic materials may include polymers such as polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymers may be woven or knitted into a mesh to form a matrix or similar structure. Alternatively, the synthetic polymer materials can be molded or cast into appropriate forms.

Biological polymers may be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Any suitable substrate may be susceptible to adhesion, attachment or adsorption by targets. The susceptibility may be inherent or modified. In one example, the surfaces of substrates may be susceptible to adhesion, attachment or adsorption to proteins. In another example, the surfaces of substrates may be susceptible to adhesion, attachment or adsorption to proteins and not to nucleic acids.

In one exemplary embodiment, a glass substrate may have a layer or coating of a material that promotes adhesion with targets, such as proteins, materials that maybe charged, such as those that are positively charged, for binding target materials. Examples of charged materials include cellulosic materials, for example, nitrocellulose, methylcelluose, ethylcellulose, carboxymethyl cellulose, hydroxyethyl cellulose, methylhydroxypropyl cellulose; epoxies, PVDF (polyvinylidene fluoride); partially or fully hydrolyzed poly(vinyl alcohol); poly(vinylpyrrolidone); poly(ethyloxazoline); poly(ethylene oxide)-co-poly(propylene oxide) block copolymers; polyamines; polyacrylamide; hydroxypropylmethacrylate; polysucrose; hyaluronic acid; alginate; chitosan; dextran; gelatin and mixtures and copolymers thereof.

In another exemplary embodiment, if the substrate is not susceptible for attachment by charged materials, or may be susceptible only for attachment by wrongly charged materials, some areas of the substrate may have adhesives, binding agents, or similar attached, adsorbed or coated thereon. Examples of adhesives may include any suitable adhesives that bind the charged materials.

The targets may be present on the substrate discretely or in clusters. The distance between the discrete targets may be close or may be far apart and may usually be of different targets. Clusters may be used for multiple spots of a single target.

In one embodiment, the substrate may be macroporous. Macroporous substrates may be desirable, for example, if the different targets are very close together. When the targets are close by, there may not be sufficient distance between different targets to distinguish which target a biomolecule may be binding to. Closely packed targets may increase the efficiency of the generating of biomolecules. A macroporous substrate may be suited for balancing between efficiency and separation. For a macroporous substrate, the walls of the pores may be sufficient to separate even closely packed targets if the pores are large enough to enable the binding process to occur within the pores.

Also, for macroporous substrates, the pores may have an average diameter greater than the average size of the target material such that the target material may enter or partly enter the pores to anchor. Hydrogels may also be useful for binding or anchoring targets to the pores. Hydrogels may also fill the pores under fluid conditions and present a smooth surface for fluid flow while at the same time may keep the fluid from flowing through the pores.

The plurality of targets may be arranged in any appropriate manner such as, for example, in circular or elliptical spots, square or rectangular spots, stripes, concentric rings and/or any other appropriate arrangement on the subject.

According to one exemplary embodiment, the substrate may be at ambient temperature throughout.

According to another exemplary embodiment, the substrate may include a temperature affecting system that generally produces at least one desired temperature on the surface of the substrate and the adjacent fluid. The desired temperature may facilitate the biomolecule generating process.

According to a further exemplary embodiment, the substrate may include a temperature affecting system for producing a range of desired temperatures on the surface of the substrate and the adjacent fluid. This may be particularly useful when employing a set of targets having a significant range of, for example Tms, or melting temperatures. In one embodiment, the system may include a plurality of temperature affecting devices that are in thermal communication with the substrate. The plurality of devices may generally be disposed such that they may each produce a desired temperature in a given locality on the surface of the substrate. The set of targets may also be distributed on the surface of the substrate such that the temperature at the location of a target is substantially at the Tm of the target.

Temperature affecting devices may be any appropriate device that may substantially produce a desired temperature on a substrate and may include, but are not limited to, thermoelectric devices such as Peltier junction devices, semiconductor heating devices, resistive heating devices, inductive heating devices, heating/cooling pumps, electromagnetic radiation sources and/or any other appropriate devices. Temperature may also be affected by other systems, such as, for example, fluid flows including, but not limited to, water flows, air flows, and/or any other appropriate fluid flows.

In an exemplary embodiment, a plurality of Peltier junction devices may be utilized to generate desired temperatures at localities on the surface of the substrate. Peltier junction devices are particularly useful since they are able to both heat and cool using electrical current. This enables Peltier junction devices to generate temperatures above and below the ambient temperature of a system. They may also be useful in maintaining given temperature conditions at a steady state by adding and removing heat as necessary from the system.

In general, the placement of the temperature affecting devices may determine the temperature profile on the surface of the substrate and the adjacent fluid in the chamber. The temperature affecting devices may thus be disposed at appropriate positions such that given temperatures may be produced and maintained at known positions on the substrate.

The substrate may in general have a given thermal conductivity such that the application of at least one temperature affecting device may substantially generate a temperature gradient profile on the surface of the substrate. In general, the temperature on the surface of the substrate may change as a function of the distance from the position of the at least one temperature affecting device. Substrate materials with a relatively low thermal conductivity may generally produce highly localized temperature variations around a temperature affecting device. Substrate materials with a relatively high thermal conductivity may generally produce more gradual variations in temperature over a given distance from a temperature affecting device. It may be understood that at steady state, the effect of the thermal conductivity of the substrate may not contribute to the temperature profile of the system.

In some embodiments, at least one temperature affecting device may be utilized to produce a particular temperature gradient profile on the surface of the substrate. In general, a temperature gradient may be generated by utilizing at least one temperature affecting device producing a temperature different from the ambient temperature of the system. Multiple temperature affecting devices with at least two producing different temperatures may be utilized to generate a temperature gradient without reliance on the ambient temperature of the system.

The positions and temperatures of multiple temperature affecting devices may be utilized to calculate a resulting temperature gradient profile on the surface of a substrate using standard heat transfer equations. An algorithm may then be utilized to calculate the optimal positions and/or temperatures for a plurality of temperature affecting devices to produce a desired temperature gradient profile on the surface of a substrate. The algorithm may be, for example, applied using a computational assisting system, such as a computer and or other calculatory device. This may be performed to tailor a temperature gradient profile to a particular substrate with a known disposition of targets of known and/or calculated Tm. Similarly, a set of targets of known and/or calculated Tm may be arranged on a substrate based on a temperature gradient profile. This may be desirable as placement of a target at a given location on a substrate may be accomplished more easily than tailoring a temperature profile to pre-existing locations of targets on a substrate. In general, a target may be disposed on the substrate at a temperature address within the temperature profile gradient. The temperature address may, for example, be substantially at the Tm of the target during operation of the molecular hybridization system, and/or any other appropriate temperature.

In another aspect, the molecular hybridization system includes an adjustable system for generating a temperature profile. The adjustable system generally includes a plurality of temperature affecting devices, each affecting the temperature at a particular location of a substrate.

Details of the temperature affecting systems may be found in, for example, U.S. utility patent application Ser. No. 12/249,525, filed on Oct. 10, 2008, entitled "METHODS AND DEVICES FOR MOLECULAR ASSOCIATION AND IMAGING", the contents of all of which are hereby incorporated by reference.

Figure 6:
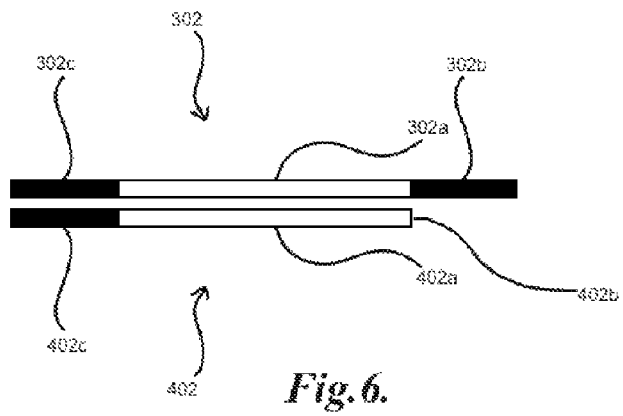
Figure 6A:
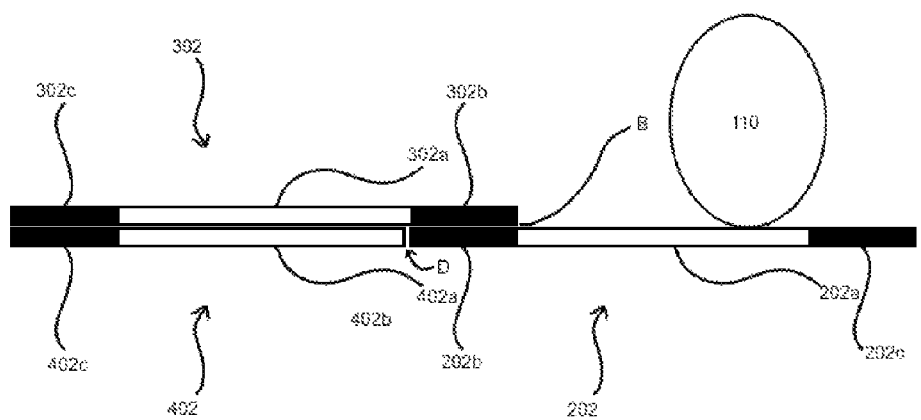
Figure 6B:
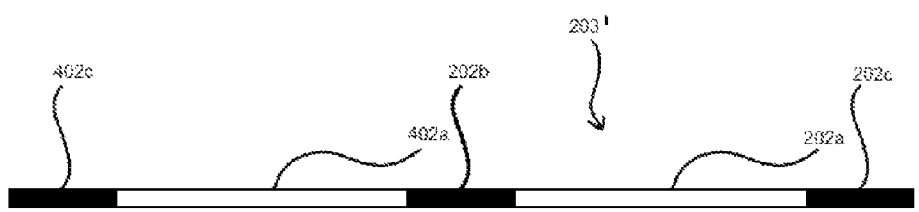

FIG. 6 illustrates an example of an identifier sequence 302 and a complement identifier sequence 402. The complement sequence 402 may include a complement identifier region 402a which may be substantially complementary to identifier region 302a such that they may base pair bind. The complement sequence 402 may further include a primer region 402c which may also be complementary to primer region 302c of the identifier 302. Further, the complement sequence 402 may include a compatible end 402b which may be compatible with ligation to the end of another nucleic acid. As shown in FIG. 6a, a nucleic acid library member 202 may be bound to a spot 110. An identifier 302 and a complement sequence 402 may then be applied to the member 202 such that the identifier 302 binds to the member 202 at region 202b, 302b. The complement sequence 402 may bind to the identifier 302 at regions 302a/402a, 302c/402c. The compatible end 402b may then be ligated to the end D of the member 202 by an appropriate ligase and/or other appropriate method. A product 203', as illustrated in FIG. 6b, may then be generated including the primer region 202c, binding sequence 202a, region 202b, complement identifier region 402a, and complement primer region 402c. The product 203' may then be amplified, such as with the product 203 discussed above in FIG. 4a. The product 203' may also be generated by single-stranded ligation of the member 202 and the complement sequence 402, where in general the either the member 202 or the complement sequence 402 may have a phosphorylated end while the other may be unphosphorylated for end to end ligation.

In another example, as illustrated in FIG. 6c, a further complementary fragment 502 may be included that may base pair bind to a complementary region 202d of the nucleic acid library member 202. This may be desirable as some nucleic acid ligases may generally join double stranded nucleic acids. The addition of the complementary fragment 502 may generally generate a substantially double stranded nucleic acid, such as illustrated spanning from region 302c to the end of complementary fragment 502. There may further be a double stranded "break" at points D and E. In general, the sizing of the fragments may be tailored to generate a suitably long stretch of double stranded nucleic acid for ligase action. In general, the complementary region 202d may be the same for all members 202 of the library 200 such that the same complementary fragment 502 may be utilized, such as, for example, convenience, cost and/or ease of use.

In general, methods may be applied that may facilitate binding or other interactions between the identifiers and the nucleic acids bound to the spots. For example, the temperature may be increased to dissociate the nucleic acids from the spots. The temperature may subsequently be lowered such that, for example, base pairing may occur between the nucleic acids and the identifiers. Temperature changes may also, for example, denature the target such that the nucleic acids may no longer bind and/or bind with lower affinity to the targets. This may be desirable in that it may aid in binding of the nucleic acids to the identifiers.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration×time, analysis measures the annealing time of particular oligonucleotides while in solution with other nucleic acids, such as the members of the library of biomolecules. In general, the annealing time will be faster the lower the diversity of the library.

In one embodiment, a Cot-standard curve for measuring the sequence diversity of the aptamer library at any point during the multiplex SELEX process may be utilized. For example, a group of DNA oligonucleotides with a 5'- and 3'-constant region of ~20 bases identical to the initial SELEX library may be utilized. The oligos may then be converted to dsDNA by standard methods. Briefly, after annealing a primer to the oligos, Exo-minus Klenow Taq polymerase (Epicentre, Madison, Wis.) may be used in conjunction with dNTPs to fill in the ssDNA to create a dsDNA or mixture thereof. Using a standard quantitative PCR thermal cycler, a temperature profile for melting and controlled annealing of each DNA mixture may be programmed. Standard SYBR Green I specific for double-stranded DNA (dsDNA) may be utilized to report the amount of re-annealed dsDNA. At one extreme, the annealing time for a single sequence will be measured. At the other extreme, the annealing time for the initial SELEX pool, such as containing approximately 1 nmol of sequence diversity, may be measured. Annealing times of intermediate diversity may also be measured to establish a very specific Cot-standard-curve for the SELEX library. Using this standard curve, at any point during SELEX, the sequence diversity of the evolving library of aptamers may be determined by comparison to the curve.

In a further embodiment, a method for generating functional biomolecules includes obtaining a library of peptide sequences and contacting the library with a plurality of targets. In some embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Phages employed may include, but are not limited to, M13 phage, fd filamentous phage, T4 phage, T7 phage, λ phage, and/or any other appropriate phage. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

In FIG. 7, an example of a phage 600 may include a nucleic acid 610 which may generally encode, among other things, and be encapsulated by a protein coat 602, which may contain a binding region for a target 110. The nucleic acid 610 may further include a region 612 which may identify the phage and/or encode the binding region for a target. A bound phage 600, as illustrated in FIGS. 7 and 7a, may then be heated, disrupted and/or otherwise treated such that an identifier 302 may contact F the region 612. For example, the protein coat 602 may be broken and/or otherwise disrupted for entry of the identifier 302. In general, an amplification reaction and/or other method, such as those discussed above, may be utilized to tag, mark and/or otherwise introduce identifier information to the sequence of region 612. Further in general, the identifier 302 and region 612 may incorporate any, all or a combination of the elements discussed above in regards to nucleic acid library members, identifiers and/or other nucleic acid fragments. As also discussed above, the phage 600 may also be physically removed and/or partitioned in a manner that may preserve the identity of the target 110 the phage 600 was associated.

In other embodiments, other methods of incorporating and/or linking nucleic acids to peptides may be utilized, such as, for example, mRNA display, ribosome display, and/or any other appropriate method. In general, in mRNA display, as illustrated in FIG. 7b, a fusion product 600' of a messenger RNA (mRNA) 610' may be linked to a peptide 602' that the mRNA 610' encodes, such as with a puromycin-ended mRNA 612' which may generally cause fusion of the mRNA 610' to the nascent peptide 602' in a ribosome, which may then be contacted with targets such as described above with phage display. Also in general, in ribosome display, as illustrated in FIG. 7c, a fusion product 600" of a modified mRNA 610" may be utilized that codes for a peptide 602", but lacks a stop codon and may also incorporate a spacer sequence 612" which may occupy the channel of the ribosome 620" during translation and allow the peptide 602" assembled at the ribosome 620" to fold, which may result in the peptide 602" attached to the ribosome 620" and also attached to the mRNA 610". This product 600" may then be contacted with targets such as described above with phage display. Other methods may include, but are not limited to, yeast display, bacterial display, and/or any other appropriate method.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties. For example, it may be expected that multiple aptamer sequences bound to a single target may potentially share sequence motifs and/or other common features which may be at least partially elucidated by sequence sorting and/or comparison. Specific binding affinities of resultant sequences may also be determined through affinity assays. In some embodiments, surface plasmon resonance may be utilized to determine binding of an aptamer to a target. For example, sensors which monitor the refractive index of a surface bound to a target may be utilized, where the refractive index may change as a result of binding of an aptamer to the target. In general, aside from standard sequencing methods, parallel sequencing methods, such as, for example, massively parallel sequencing such as 454 Clonal Sequencing (Roche, Branford, Conn.), massively parallel clonal array sequencing, Solexa Sequencing (Illumina, San Diego, Calif.), and/or any other appropriate sequencing method may be employed.

Example of Multiplexed Selex Protocol

As a demonstration of parallel, de novo selection of aptamers against multiple targets, a combinatorial DNA library containing a core randomized sequence of 40 nts flanked by two nt conserved primer binding sites is used as the starting point for an aptamer pool. The primer sequences are designed and optimized using Vector NTI's (Invitrogen) oligo analysis module. Typically, such a library is expected to contain approximately $10^{15}$ unique sequences. The primer binding sites are used to amplify the core sequences during the SELEX process. The single stranded DNA pool dissolved in binding buffer is denatured by heating at 95° C. for 5 min, cooled on ice for 10 min and exposed to multiple protein targets fixed onto a nitrocellulose coated glass slide (e.g., Whatman).

Example of DNA Library Selex

An example DNA library consists of a random sequence of 40 nucleotides flanked by conserved primers. In the first round of SELEX, 500 pmol of the ssDNA pool is incubated with each slide in binding buffer (PBS with 0.1 mg/ml yeast tRNA and 1 mg/ml BSA) for 30 minutes at 37° C. The slide is then washed in 1 ml of binding buffer for one minute. To elute specifically bound aptamers the slide is heated to 95° C. in binding buffer. The eluted ssDNA is subsequently be precipitated using a high salt solution and ethanol. After precipitation, the aptamer pellet is resuspended in water and amplified by PCR with a 3'-biotin-labeled primer and a 5'-fluorescein (FITC)-labeled primer (20 cycles of 30 sec at 95° C., 30 sec at 52° C., and 30 sec at 72° C., followed by a 10 min extension at 72° C.). The selected FITC-labeled sense ssDNA is separated from the biotinylated antisense ssDNA by streptavidin-coated Sepharose beads (Promega, Madison, Wis.) for use in the next round. Alternatively, "asymmetric PCR" may be utilized for generating a large excess of an intended strand of a PCR product in SELEX procedures. Also alternatively, the undesired strand may be digested by λ-exonuclease, such as, for example, when a phosphorylated PCR primer is employed.

The labeling of individual aptamers with fluorescein isothiocyanate (FITC) facilitates the monitoring of the SELEX procedure. FITC is also compatible with scanning in the green (cy3) channel of standard microarray scanners. The sense primer used to amplify the ssDNA aptamers after each round of selection is fluorescently labeled, resulting in fluorescently labeled aptamers. The protein spotted nitrocellulose-coated slides are scanned in a microarray scanner. Alternatively, proteins may be spotted on epoxy-coated glass slides. While epoxy slides may have less protein binding capacity than 3-D nitrocellulose pads, it has been observed that there may be less non-specific binding of nucleic acid aptamer pools to the background of the slide (blocked or not). Blocking may be employed to reduce background fluorescence.

In each round of the SELEX process, the slide is incubated for 30 min at 37° C. to allow binding of the aptamers to their targets. The slides are then washed in binding buffer before the specifically bound DNAs are eluted by heating the slide at 95° C. in 7M urea. Nucleic acids from the eluate are phenol-chloroform purified and precipitated, and the concentrated single stranded DNA molecules will be amplified by PCR. In order to increase stringency throughout the SELEX process, the washes are gradually increased in volume (from approximately 1-10 ml). After a given point in the selection, such as, for example, after the final round of selection, the aptamers may be tagged, marked and/or partitioned.

Example of In Situ Hybridization of Identifiers

An example of in situ hybridization of identifiers to aptamers was performed with short, ssDNA sequence tags to the 3' end of aptamers bound to their protein target. These synthetic ssDNA tag oligonucleotides consists of three regions, as illustrated in FIG. 3b with identifier 302: (i) the C2 region, region 302c of the identifier 302, at the 3' end of the oligonucleotide consists of a 17-20 nucleotide sequence complementary to a corresponding region on all of the used aptamers, (ii) the C1 region, region 302b at the 5' end of the oligonucleotide 302 contains a 17-20 nt primer binding site, used during the amplification of the tag:aptamer hybrid, prior to sequencing and (iii) a variable region 302a in the center of the tag oligonucleotide (V) that serves a as a unique identifier for each locus on the glass slide surface. A variable sequence of 8 nucleotides will allow 48 (65,536) unique sequences to be generated, sufficient for many complex protein arrays (8000 samples) on the market.

As outlined above, after the final round of the SELEX procedure (typically, round 10) the specific aptamers are bound to their protein targets, fixed to a glass slide. While the 40 nt core sequence of each aptamer are unique, its terminal sequences have not been subject to any kind of selection during the procedure. After each round of binding to their protein targets, the aptamers were amplified using conserved primers, requiring the maintenance of corresponding regions at their distal ends (P1, P2). The 3'-region of each aptamer, for instance, can thus serve as a binding site (via standard hybridization) for the C2 region of the proposed tag oligonucleotide. Given the unique variable sequence (V) of each tag oligonucleotide, each aptamer will now be tagged with a sequence that can be traced back to the location of the aptamer on the glass slide, and thus the protein spotted at that location.

Example of 16-Plex Selex Procedure

An example of a 16-plex (16 targets) SELEX procedure was performed with 16 unique targets: (1) fibrinogen, (2) collagen, (3) fibronectin, (4) acetyl-bovine serum albumin (BSA), (5) heparan sulfate, (6) prolactin inhibiting factor (PIF), (7) ribonuclease A (RNase A), (8) laminin, (9) interleukin-7 cat 200-7 (IL-7 cat 200-7), (10) IL-15 cat 200-15, (11) IL-21 cat 200-21, (12) IL-7R cat 306-IR, (13) IL-15R, (14) IL-21R, (15) IgG2a (anti-CD19), and (16) anti-CD20. The 16 targets were arranged as a spotted array on a blocked nitrocellulose slide. A DNA aptamer library as discussed above was applied to the slide. Non-binding members of the library were washed off and the slide was labeled with 16 unique identifier nucleic acid sequences, one per target spot, as described above. The identifiers were briefly incubated at 60° C. and then allowed to hybridize to the aptamers on the spots at 37° C. for 30 minutes. Exo-Klenow Taq polymerase and dNTPs were added and extension of the identifiers was performed for 1 hour at 37° C. The Taq was inactivated at 60° C. for 10 minutes. The dsDNA was eluted with near boiling 7M urea and then precipitated with 3M sodium acetate at pH 5.0 and ice cold ethanol. The recovered dsDNA was sequenced by standard methods.

Identifier sequences in the sequenced DNA were utilized to identify the target of the aptamer sequence. The following aptamer sequences were identified for the targets (identifier sequences and priming sequences removed):

Target 1:
(SEQ ID NO.: 1)
5'-CAAGAGTGTTAGACATTATCTCAGCGCTGCCAATTATATT-3'

Target 2:
(SEQ ID NO.: 2)
5'-AGAGGCGGCTGAGATCAATCTCCGCTCAGGGAGCGAGTA-3'

Target 3:
(SEQ ID NO.: 3)
5'-CAATACAATACTATATTTGTGTCAATCTCGTACTTCTGAC-3'

(SEQ ID NO.: 4)
5'-CAATATGTCTAATTTTTTTACATGGCGGCATGGTATTGGC-3'

Target 4:
(SEQ ID NO.: 5)
5'-AAGATCTTTATTAAGCAAACAATGTTAACTATAGAGCGTT-3'

(SEQ ID NO.: 6)
5'-GAATTACATTCAAAAATTTTCTTCTGGCATCTGTAATACCG-3'

Target 5:
(SEQ ID NO.: 7)
5'-TGATACAAATACTCTCAATCAAAGCCAATATGTCGCAAAA-3'

(SEQ ID NO.: 8)
5'-CAAAGTAAAATTAACAGATAGTACGTTCTCAATCTCGCGA-3'

Target 6:
(SEQ ID NO.: 9)
5'-TCTTCTTGCACATATTTTTCTCCGTGAGACATGTAAATAA-3'

(SEQ ID NO.: 10)
5'-ATGTACTTCACTTCAGTTTTCTTTAAACACGTTTCACATA-3'

(SEQ ID NO.: 11)
5'-CCGCATTTATCAGTTTACCGCCCCATAAACATAACCGCT-3'

(SEQ ID NO.: 12)
5'-AATTATGCTCATGATTTTCTTCAAAAAGGCTCGCGCAATT-3'

(SEQ ID NO.: 13)
5'-GGCTGTTAAACTTACTTTTCTTCAGTAATTGCCGTTGACA-3'

(SEQ ID NO.: 14)
5'-TAGTTTATCAGGAGCGATCACTGATCATGAGTAACTTTTA-3'

(SEQ ID NO.: 15)
5'-ATCAAGAATTGATAATTTTAGGAATTGCGTATCGCTGCTA-3'

Target 7:
(SEQ ID NO.: 16)
5'-AACTGTGTTTTAGGACTTCATTGTCTTAATTCTCTTCCCT-3'

(SEQ ID NO.: 17)
5'-AGCGCGATATTACGGTCTCGAACCAAAACCATCACGGTTC-3'

(SEQ ID NO.: 18)
5'-ATAGTTTAAATTTAATCTTCTGCCACCCTTCACTTTCA-3'

Target 8:
(SEQ ID NO.: 19)
5'-GCACATCTCCCGTTCGACTTTTTTATCTTCGAGCACCTAA-3'

(SEQ ID NO.: 20)
5'-CCATGTAGCACAAAACAACGATATAAGAACTACATTTAGT-3'

(SEQ ID NO.: 21)
5'-GGCTTTCTAATCTAACACGATCTCCTCTCCTTACGCCGTG-3'

(SEQ ID NO.: 22)
5'-TACTCTTGTTTAAACTAGAACAGTAAAATATTAATTCTTA-3'

(SEQ ID NO.: 23)
5'-TGGAGTTTATAATACTCGAGGCTAGTAGTGCCATTTTACA-3'

(SEQ ID NO.: 24)
5'-ACGCGCGGCTGTGGGGAAGGTACAGGTTCCGAACGATGGA-3'

(SEQ ID NO.: 25)
5'-ACAAGAACTATTTTTATCAAAGACGTCACCAACTTAAGGC-3'

(SEQ ID NO.: 26)
5'-CAAATAATCGTTTTATAATTACCAACACATTTTGGTTAAC-3'

(SEQ ID NO.: 27)
5'-TTTATATTAAGCAACTTTTTGAGAGTTGATTGATAATTTA-3'

Target 9:
(SEQ ID NO.: 28)
5'-TGGCCTAATCTCGGAGACTGGCCGCTGTGGGCGCGGGCCT-3'

Target 10:
(SEQ ID NO.: 29)
5'-TCTAATTATGTTACAAAATAATTGTTATGCTCCGCAAATA-3'

(SEQ ID NO.: 30)
5'-TCATTTAATTGTCCTAAATCTGAAAATTTATTATATTTC-3'

Target 11:
(SEQ ID NO.: 31)
5'-CCGGGATAAATTACTAAGTTTCGGGTATTTTGACAATATT-3'

(SEQ ID NO.: 32)
5'-AAACCTGCAAAATTTAGGGCCAATGTGTGTATTGAACGGG-3'

(SEQ ID NO.: 33)
5'-GTTATAGTAATATTGGTTCTAGCTCTCAGTAATATCAAAA-3'

(SEQ ID NO.: 34)
5'-ACCCTATAAGCTGAGATAAGCATTCTGTGGACGAAAAGTT-3'

Target 13:
(SEQ ID NO.: 35)
5'-AGGCGTTAACTCTTGTCATGTTATAGACGTCTAATCCATC-3'

Target 14:
(SEQ ID NO.: 36)
5'-ACTGTAATCACTTCTTTTAAATAGTCCCGGAACGATATCA-3'

(SEQ ID NO.: 37)
5'-CTTGATCCATACTATAACTTAACATTTGTTCATCTCAAGT-3'

Target 15:
(SEQ ID NO.: 38)
5'-CTAAATCGCGAACCGAGTTTTTGTCAAAGTTCTAGATTAA-3'

Target 16:
(SEQ ID NO.: 39)
5'-ACGAACTTTTTTAATTCGCAGACATGTTTATAGTTTCTTG-3'

No aptamers were recovered for target 12 (IL-7R cat 306-IR).

Example of Aptamers to Target Molecules

Examples of aptamer sequences to target molecules are illustrated in the following table showing, for example, the target molecule and the aptamer sequence in 5' to 3' DNA sequence. The sequences may also include any modifications, concatenations, and/or truncations thereto and in general may include any sequence with substantial or significant homology or sequence identity with the aptamer sequence shown in the figures. Unless otherwise notated, the targets in the table are generally human-derived proteins. For example, LAP (TGF-b) stands for latency-associated protein, hCG stands for human chorionic gonadotropin, IgM-BAS and IgM-BAG are both immunoglobulin M, IgC-FC stands for IgG, Fc constant region, and murine monoclonal anti-Hen Egg Lysozyme antibody (an IgG).

TABLE 1

| | TARGET | 5' to 3' Sequence |
|---|---|---|
| SEQ ID NO.: 40 | IgM-BAG | GAGGGGGGGGCCAGGCCGCCAGGAGCGAAGGTCCCGGCCC |
| SEQ ID NO.: 41 | IgM-BAG | CGTGGTTGGATTGGGGGGCGTGTTCGCCTGAGTGCAAGGC |
| SEQ ID NO.: 42 | IgM-BAG | TACGCGGTTTTTGTATCCCAAACCATTGCATCATCTCTAA |
| SEQ ID NO.: 43 | IgM-BAG | GTCATTCTTTTAGTATTAAATTTAGAATTACTCCTCCAGA |
| SEQ ID NO.: 44 | IgM-BAG | CAAAGAAAATGGTCATGAAATAGCGTACTAACATGGAGTC |
| SEQ ID NO.: 45 | IgM-BAG | CTAGTTTATCTTATAACGAAATGTTGTTTTTATGCTTTCA |
| SEQ ID NO.: 46 | IgM-MuChain | TGCAAAAGAGCCCTACTCTTGCTCTCAGATCCCTTCTC |
| SEQ ID NO.: 47 | IgM-MuChain | TTCGAATTCTATCAATTTGAGACGATTTAGT |
| SEQ ID NO.: 48 | IgM-MuChain | AGGTCGTTTATGACTAACACTTTAGATTCGACACACAG |
| SEQ ID NO.: 49 | IgM-MuChain | AGTTGTTTGGTCGATATGGCCTTTGCTCCAGGGTTGCCG |
| SEQ ID NO.: 50 | IgM-MuChain | ACAAAAGAAAGGTTGCATCGAACAGATAACTTACATAT |
| SEQ ID NO.: 51 | IgM-MuChain | GAGTGAATGTCAGGTGCATGAATGTTTCCGTATAGCGCGA |
| SEQ ID NO.: 52 | IgM-MuChain | TAGATTAATTGGATGTTGTATACCTAGTATAGCCATTG |
| SEQ ID NO.: 53 | IgM-MuChain | AAGCGCGTTATCAGTATAAAGGAAACATAACATACTCG |
| SEQ ID NO.: 54 | IgM-MuChain | TAATTATTTAGTAATAGATTAAGTTTCTTAGATGCTAAC |
| SEQ ID NO.: 55 | Collagen | AGACTTGAAAGCATCTTTACTTCGATTGGTAATATTTTTG |
| SEQ ID NO.: 56 | IgG-FC | TTGAAGGCGTACCGTCCGCGGGCGGCGTGTGCGCCGGGCC |
| SEQ ID NO.: 57 | IgG-FC | TTGAAGGCGTACCGTCCGCGGGCGGCGTGTGCGCCGGGCC |
| SEQ ID NO.: 58 | IgG-FC | GGGGGCGCGTCGCAGGGGGGACGCGGGAATCGAGGAGCA |
| SEQ ID NO.: 59 | IgG-FC | GGGGCCGATTCGGCCAGTCCGGGGGCCCGACATCGGAGA |
| SEQ ID NO.: 60 | IgG-FC | CGGAAAATTATTCTGTAATTTTCTAACTCTGGTTAGACTT |
| SEQ ID NO.: 61 | IgG-FC | CCAATTTGGGATATGCTTCAGGATCCCCTGAGTATGGTTT |
| SEQ ID NO.: 62 | IgG-FC | CAAACGCATTAGATCGAATCTAATTGTTGCAACAAAGTCA |
| SEQ ID NO.: 63 | IgG-FC | CAGGGATTTATCCCCCATGCGGACNCGTAGCCACCCGGAA |
| SEQ ID NO.: 64 | IgG-FC | CGTTAGTTTTCTTTACGTGAAAACAGTTTGACTTACGCCA |
| SEQ ID NO.: 65 | IgG-FC | CGTTTTATTATGGGTTTATAAAACATCAGCATCACAAGAT |
| SEQ ID NO.: 66 | IgG-FC | ATTTATAGGGTCTGTATTAAAACAATTTTAATTTCACTCT |
| SEQ ID NO.: 67 | IgG-FC | CCACGGGTGGGATTCTATTATTTAACTAACTAATGTACA |
| SEQ ID NO.: 68 | IgG-FC | AAGGGATGTTTGGCGTTCTGATTAACGTTAGGAACCATGT |
| SEQ ID NO.: 69 | IgG-FC | TGAAATAAATTCTTGAAGAGAACCATTTATCGGGTCGTCA |
| SEQ ID NO.: 70 | IgG-FC | CGGGGGTTCCCTGTAATATAAAGTGTCATTTAGTGCGCCT |
| SEQ ID NO.: 71 | IgG-FC | CGAATTTAGTTAATGATCGTAATATTACAAATAAATTT |
| SEQ ID NO.: 72 | IgG-FC | GCAATTTTCAGGGTATCAACAGGCCCATATGGATCATCAC |
| SEQ ID NO.: 73 | IgG-FC | CGAAGTTGAGTTATTTATTTATCTCATCTAATAGTCAGTT |
| SEQ ID NO.: 74 | IgG-FC | CATGGTGTTTATTGATCAATCTTTGACCGTAGAGGAATAT |
| SEQ ID NO.: 75 | IgG-FC | GTAGTTTTCAAATTTAAGCGGCGTGAACTTAATAAGTACT |
| SEQ ID NO.: 76 | IgG-FC | GGCTTTTATTCGTGCCGTTTAACAGACAAAATCATTCAC |
| SEQ ID NO.: 77 | IgG-FC | AGGTATTATTTTACAAAAGAATTAGCTATAACCGAATAGA |
| SEQ ID NO.: 78 | IgG-FC | AGGTATTATTTTACAAAAGAATTAGCTATAACCGAATAGA |

TABLE 1-continued

| | TARGET | 5' to 3' Sequence |
|---|---|---|
| SEQ ID NO.: 79 | IgG-FC | TTTAAGTTAATAGTAGTTCTGAAGACGATTACCCCGTGA |
| SEQ ID NO.: 80 | IgG-FC | AGCTAATACTTTATTTCTTTAGAGAGTTGTGCATA |
| SEQ ID NO.: 81 | IgG-FC | GTGTTACTTTTTTTCTGGTGAACGAGTTAACTACTTCAA |
| SEQ ID NO.: 82 | IgG-FC | GTTGTAGTTTTAAGATTAAGTGTACGCATGTTACGGGTAT |
| SEQ ID NO.: 83 | IgG-FC | ATTAATATTTAATCAAGGCTCTCAACATTTTCATACTAT |
| SEQ ID NO.: 84 | IgG-FC | AGTACTATTGAGATTATTCGTCATGGAAATCGGTATCGCT |
| SEQ ID NO.: 85 | IgG-FC | CGAAAAACGGTTATTATTATCTTCTTATTATCTCCCTCA |
| SEQ ID NO.: 86 | IgG-FC | CGATTTTGGTATTAATTATATATGCGGTGTGGTCGAGGTT |
| SEQ ID NO.: 87 | IgG-FC | CGTTTATTTATTGAACCACTTTTGTTATCTAGCGCTTAGC |
| SEQ ID NO.: 88 | IgG-FC | CTTATTGTTAAAGGTCTAGTTTTATTTCAATCTCACACCT |
| SEQ ID NO.: 89 | IgG-FC | GATAATTTCTAAGGATGCGCTAACATAACTCACTCGTATT |
| SEQ ID NO.: 90 | IgG-FC | GTCGTTCGTTCCCTAATCTTTTCTCCTTAGTTCAATTCA |
| SEQ ID NO.: 91 | IgG-FC | GTGAGATTTTATAATACTTTAAGCACGTATCCTGATT |
| SEQ ID NO.: 92 | IgG-FC | GTTTAATTTCGTTATTTTTCTAAGTTTCAAGATTTGCTCA |
| SEQ ID NO.: 93 | IgG-FC | TGTTTGTTGGAATATTTATTTGAAGGTCCGTATATATCTT |
| SEQ ID NO.: 94 | Fibrinogen | GGCGCGCTGGCGCGCGAAGGTGGCTCGGAGTGCTCCGGGC |
| SEQ ID NO.: 95 | Fibrinogen | GAGGGCGGGCCGGGCCCGGCCCAGGAGGAGGGAGGCCCCG |
| SEQ ID NO.: 96 | Fibrinogen | CGGATAGGTAGGCCCCCTCCACGGGCCGGGTCGGCCCGGC |
| SEQ ID NO.: 97 | Fibrinogen | CAGGGCGTGAAAGGAGCGGGGCAGGGGCCCCGAAACAAAC |
| SEQ ID NO.: 98 | Fibrinogen | GGGTTGTTTTTACGAACCGGACCGAATAACGGCACCGGCC |
| SEQ ID NO.: 99 | Fibrinogen | TGGGAGGGCTTGGGAGCCAGGTCGTCAAGGCGGGGTCCCC |
| SEQ ID NO.: 100 | Fibrinogen | GCATCACATATCGCCCCGTGACTGGGCCAAAAGGCCGGAC |
| SEQ ID NO.: 101 | Fibrinogen | CCAATGAATTGAGTGTGCTTTTTTTTCGAAACTCAATTC |
| SEQ ID NO.: 102 | Fibrinogen | CAGATGGACGTTCGTCGTTAATTGTTAAGGCGTCGCCGTC |
| SEQ ID NO.: 103 | Fibrinogen | GATATTCTGAGTGATCGATCGTACGATCAATAATCTAGTA |
| SEQ ID NO.: 104 | Fibrinogen | GGGTCGATTGGTTTTGCTTCCATACTATATGTAGCAATTG |
| SEQ ID NO.: 105 | Fibrinogen | CGATTTGTAATGGTTTATACCATTTAGGTTTTTCGAAAAT |
| SEQ ID NO.: 106 | Fibrinogen | AGCTATTCTATGGAGAGTCAATTTTCACTGCATAGCAGTA |
| SEQ ID NO.: 107 | Fibrinogen | CAGTAATATTCTACTTTCCGATACGGCTTCGTATGCGATC |
| SEQ ID NO.: 108 | Fibrinogen | AGGATTTAATCTGTGTGATTAGCATGTTCCGACACCGGCC |
| SEQ ID NO.: 109 | Fibrinogen | GTGGCAAATTTATGTGTTCTCAAAAAACACAAACAACAAC |
| SEQ ID NO.: 110 | Fibrinogen | CGTAACGACCTGAAATTCGGGTACTACAGAAATCCAATTA |
| SEQ ID NO.: 111 | Fibrinogen | TTGTTTTATGTTTTTGCCAGACTTTAAGGCACCAAGCT |
| SEQ ID NO.: 112 | Fibrinogen | CCGATTATTGTTATTCTAGAAGTGAGCATGATCGCACACT |
| SEQ ID NO.: 113 | Fibrinogen | CTTGTTTTTGAAAGCATGTCGCTAAATGGTAGTTTTCAAT |
| SEQ ID NO.: 114 | Fibrinogen | CAGTGGAGGGAGTGCGTTCTGGAGGAGCGGCCCGCAGAC |
| SEQ ID NO.: 115 | Fibrinogen | CTAGGATAAAAGGTAATTGAATTAACATAGGCTTTTAACG |
| SEQ ID NO.: 116 | Fibrinogen | GGCGGGGGGCTAGCAGAGCGGGAACGGGCGGCGGCAACAA |
| SEQ ID NO.: 117 | Fibrinogen | TGTACGGGGGATCCAAGTTATGGACAGGCTTCAATTAGA |

TABLE 1-continued

| | TARGET | 5' to 3' Sequence |
|---|---|---|
| SEQ ID NO.: 118 | Fibrinogen | CCTTGTCGGTAAATACCAGTACTAGTACGTTAGATACGGA |
| SEQ ID NO.: 119 | Fibrinogen | CCTTGTCGGTAAATACCAGTACTAGTACGTTAGATACGGA |
| SEQ ID NO.: 120 | Fibrinogen | GAGAAGGGGAGATGGGGAGGGATACACGGGCCCGCATATG |
| SEQ ID NO.: 121 | Fibrinogen | AGATTAAAATATGTAGACCCCATGTTAATCAATGAACACT |
| SEQ ID NO.: 122 | Fibrinogen | GAGTTTGGAATGTATGTGTATATACACGCCCTTCATTTTT |
| SEQ ID NO.: 123 | Fibrinogen | GTCTGAAGACTAGATTTCTTTTTCAAAATGAACAGGCCA |
| SEQ ID NO.: 124 | Fibrinogen | ACGAAATATAGTTATTTAGTCCTTATTACATTTTTGCTTC |
| SEQ ID NO.: 125 | Fibrinogen | TGTTAATGATTTAAAGACTGTTTGATAACGCAGTAA |
| SEQ ID NO.: 126 | Fibrinogen | CAATATAATAAATGTTGAACCGTGTAATTCATAATACGAC |
| SEQ ID NO.: 127 | Fibrinogen | GAAGAAATAGCGATGATAATTTCAATTCCGTAAACCAGTC |
| SEQ ID NO.: 128 | Fibrinogen | TACATATAAAGATGTGTCAACTAGAAATACTTTCCATACT |
| SEQ ID NO.: 129 | Fibrinogen | ATTCTAAGGCTTGAAGCAGTCCTAACCTATAACTCCGGTG |
| SEQ ID NO.: 130 | Fibrinogen | AAGGTTTATGAGTAAGTCGGATGCCTACAATATACTTAAT |
| SEQ ID NO.: 131 | Fibrinogen | CACTGTTTGCGGAAAGAACTTGATTTGAGTTAGTATACCA |
| SEQ ID NO.: 132 | Fibrinogen | TTAAGGTGTAAATTTAAAAATGTTTACCTATTCTTTCCAC |
| SEQ ID NO.: 133 | Fibrinogen | CGATTTATTTGGGTAACAGTCCATCCACGTTATACACACG |
| SEQ ID NO.: 134 | Fibrinogen | GATAATAGAAAAGCTTACGCACATCTAGAC |
| SEQ ID NO.: 135 | Fibrinogen | TAAATATGTCAATTTTAATTCATGCACACCCCTTGACTCG |
| SEQ ID NO.: 136 | Fibrinogen | CCGATTATTTATCAATAACATATGAATCCTAACATCCATA |
| SEQ ID NO.: 137 | Fibrinogen | GCTATTAGTTGTTGTTCAAATATTCGTACATTCGCTGAAC |
| SEQ ID NO.: 138 | Fibrinogen | ATTATCCTTTGTTTTGAATGCATTAGTTACTAACCGCTAA |
| SEQ ID NO.: 139 | Fibrinogen | GTTTGTATTCAACAGGCACATGCTATAAGACACTTTACTA |
| SEQ ID NO.: 140 | Fibrinogen | CAGGATTTTTTTGTTCAGGATTATACTTACTTCCTCCCA |
| SEQ ID NO.: 141 | Fibrinogen | CGGATTGGCAAAGAGAAGACCAGTTTCTAGGTTATAGTGC |
| SEQ ID NO.: 142 | Fibrinogen | CGGGAATGAACGAGGCAGACCACACTAGCGCAGATAGATT |
| SEQ ID NO.: 143 | Fibrinogen | GTGATGGATTTTGGACAGCTCAGTTCTAACTCCCAGGAA |
| SEQ ID NO.: 144 | Fibrinogen | TAATAATTTATAAATCTGAGGTTTGCATAGTCAACTCTCC |
| SEQ ID NO.: 145 | Fibrinogen | CTTGATTAACAGACTATATTTGTTCGAATTACCACACC |
| SEQ ID NO.: 146 | Fibrinogen | GTCAGAATTTTTTAGGTTACTTAGGTGACTCCCATATACA |
| SEQ ID NO.: 147 | Fibrinogen | AGAGGAAATTTTATTCTGATTTAAGTCATGACCCCCACTG |
| SEQ ID NO.: 148 | Fibrinogen | CAGGTANGAGTCGNTAAGTTTTGGTCATCCTNTGCCACT |
| SEQ ID NO.: 149 | Fibrinogen | GATGTATTAAGGGGCTTCCACGTTGTGCATGAGTAATTCT |
| SEQ ID NO.: 150 | Fibrinogen | TAGAAAAAAAAGAGTGTACTATTCTACAATAATCTACTT |
| SEQ ID NO.: 151 | Fibrinogen | TGGTGTATTTTTTAGCATAACCTTAAGATCTCGGTACATC |
| SEQ ID NO.: 152 | Fibrinogen | ACTTCTTTATCGTCGAATACCTTAATACTGCTCATTGAG |
| SEQ ID NO.: 153 | Fibrinogen | CACTGTATACTAACGCATATATTCACATTTGTCATACTTC |
| SEQ ID NO.: 154 | Fibrinogen | CATGTAAATTTAAATCTTTGGTAACGGAGTTTTGGCCTTT |
| SEQ ID NO.: 155 | Fibrinogen | CGTTCTATCTCATACTTCATCTCCATTG |
| SEQ ID NO.: 156 | Fibrinogen | CTAGACAATTGTATTTTTGATGCTTCCACACCCAATTTAC |

TABLE 1-continued

| | TARGET | 5' to 3' Sequence |
|---|---|---|
| SEQ ID NO.: 157 | Fibrinogen | GATGTATTTTCAGCCTAATTCTAAAGTCAATATTTGTG |
| SEQ ID NO.: 158 | Fibrinogen | NNNNGTNGTTNGATGANNGNNGATNNNNGGNAGCCTTTAC |
| SEQ ID NO.: 159 | IgG-BAS | AGGAGGGGGATCGGCCAGAGGCGGACGGGACGCCCGTGGA |
| SEQ ID NO.: 160 | IgG-BAS | GACGGATTTTATAAGGTTATGATATAAACCTCGATCGTTG |
| SEQ ID NO.: 161 | IgG-BAS | GTATTGTAAGAGAATCTTTACAACTACAATGTATTTTTAT |
| SEQ ID NO.: 162 | IgG-BAS | GGTTTTTTTAAAATCGTTTTTTCATTCAGCAATTAGCTCG |
| SEQ ID NO.: 163 | IgG-BAS | GCGTTTTTTCTGATTTTCCTTATTTAATCCACTGATGACC |
| SEQ ID NO.: 164 | IgG-BAS | TGTAAGAGATAATTTTAATCGAATTCCTGTGTTATAGCC |
| SEQ ID NO.: 165 | Fibrinogen | AGGAAACGGTCTATGTACCAATATTTGTACTATAGGCCC |
| SEQ ID NO.: 166 | Fibrinogen | CTAATATTTTAGAAAACTTAGTAAATAGGGCTACTT |
| SEQ ID NO.: 167 | Fibrinogen | GTTATTTTATTTAAGCCAAACCTCTAGATACTTCACTATC |
| SEQ ID NO.: 168 | IgG-FC | CGTTTAGGTTGCCTAATAAAAATTTCTCCAATTTTACATT |
| SEQ ID NO.: 169 | IgG-FC | CTATAAGACATGTTTAAATACAACCTACTGATTGTTATC |
| SEQ ID NO.: 170 | IgM-MuChain | GGAGGTTAATTGGGTCAGAGCGTTAACAGGTAACGTTTT |
| SEQ ID NO.: 171 | IgM-MuChain | TTTTATTTCGTATCCTATATTTTCAAGTTAGCTTGACTC |
| SEQ ID NO.: 172 | IgM-MuChain | TTGATTTTACAAAATGCTTTAAAGTAGGTAATTTGTACCA |
| SEQ ID NO.: 173 | IgM-MuChain | CGATTATTGCTTTATAAAAGACCCAGACGTCATCATTATC |
| SEQ ID NO.: 174 | IgM-MuChain | TCAATAGTTTTAATCCCTAAACCGACTTCAATC |
| SEQ ID NO.: 175 | IgM-MuChain | GGTATAACTCTATTGTCGATAAAATCCCTCTTATTCAGCA |
| SEQ ID NO.: 176 | HSA | CTCTTAATGTCACGGCTGAGCCTATGCTGGCGTGACCGA |
| SEQ ID NO.: 177 | HSA | GTTTAAATAATGAATACAGGTATGTATTTGGGTCATCCTG |
| SEQ ID NO.: 178 | HSA | TGGATCTTTACTTGTTTACTACAAGGTTATTATCGCTTAA |
| SEQ ID NO.: 179 | HSA | GTGGTTTTTTCAAGCTTTTACTGCGCCCGCGTGAGCGT |
| SEQ ID NO.: 180 | HSA | TGAATAGTGTCGCGACTGGGGCTGGACCTGCTTGATGG |
| SEQ ID NO.: 181 | HSA | TACAAATTGTCTTAATAATCGTTATGTGTATTGGAGTAAT |
| SEQ ID NO.: 182 | IgM | GGGGGGGGGCCCGGCCGGCAAGGCCAGTGGCGCCCCGGGC |
| SEQ ID NO.: 183 | IgM | GGGGGGGACCGGGGCCGGCCCGGGGCCCCCGCGCCCGGCC |
| SEQ ID NO.: 184 | IgM | GAATAAGAAGAATGTCACGCGGCCTTGGGGCCTGCGCCCG |
| SEQ ID NO.: 185 | IgM | TAGTGGGAATTAAGTGCGGGTCCGGGCACGGCCTCGCCGC |
| SEQ ID NO.: 186 | IgM | AACGGGTATAAGCAGAGATTATGATGAGCCCTCTCTGGCC |
| SEQ ID NO.: 187 | IgM | CGCGGAGTGAGTAAAAATTTTAAGCTTATAAACCCGCTTA |
| SEQ ID NO.: 188 | IgM | GGTCTTAGAAAACAGATATTCTAGATACTAATATAGTGTT |
| SEQ ID NO.: 189 | IgM | CAGTGTATCTTTAGCTGCCGCGGAATTTCCTGAGCCGGAT |
| SEQ ID NO.: 190 | IgM | GGTCTAGGTTTATTATCAATATTAGCACAACGGGTATAT |
| SEQ ID NO.: 191 | IgM | TCCAAGTTCAAACCTTAGGAACAAATGGATGCGCAGCGAT |
| SEQ ID NO.: 192 | IgM | TGATTTTTATTGATCGTTATTTGAAGACATCTTCCAGGA |
| SEQ ID NO.: 193 | IgM | GACGCTTACGCTTGTTAATAAGATTTTTGTTTTCATTACA |
| SEQ ID NO.: 194 | IgM | TCTCTTTTCTTGAATCTTGCATTTAACCCATCCCTTCAAA |
| SEQ ID NO.: 195 | HSA | GTGTGAAAGCTGGGAGAGTCTGCGGGCCTGTGTCGCGCAA |

TABLE 1-continued

| | TARGET | 5' to 3' Sequence |
|---|---|---|
| SEQ ID NO.: 196 | HSA | CGTAGGAGGGAGATTCCCACAAACGCTCCCCAT |
| SEQ ID NO.: 197 | HSA | CGAGATCGTTATATAAGGGACAATCTGACGATTCTACCTT |
| SEQ ID NO.: 198 | HSA | ATGGGTGTGTCTGGGTAGACGTTGTTTTGGCCTGGTGTTA |
| SEQ ID NO.: 199 | HSA | TCAATTAAGATCTTGTGTCAAGTGTTAAAGTCCGTCATGA |
| SEQ ID NO.: 200 | HSA | AATTGTTCGGTTGACGCTTTTCTGACGCTGTATACCCTGG |
| SEQ ID NO.: 201 | HSA | GATGCTATTTTTGATAGATACATGTAACCTTTTAGACTTT |
| SEQ ID NO.: 202 | HSA | GATGCTATTTTTGATAGATACATGTAACCTTTTAGACTTT |
| SEQ ID NO.: 203 | HSA | AGCTTTTTATGGAATTATTCTCACAACACATTGGAACATT |
| SEQ ID NO.: 204 | HSA | TGGAGTGAGTGACTTGACTACTTACAGTAACCTCTACAGT |
| SEQ ID NO.: 205 | HSA | ATGTGTCAAAGATTATCGAGAAACGCTGTTTTTATTGTA |
| SEQ ID NO.: 206 | HSA | AGATCCATTAGAATCAATTTATTTGGGCATCGTATTCCGC |
| SEQ ID NO.: 207 | HSA | ATTAACTTAAAAACAATCCTTAATCGTTGCAATTAAATCC |
| SEQ ID NO.: 208 | HSA | CTTCGTTAAATCTGTATGTACCCGTAGCTAGCTTAATTTC |
| SEQ ID NO.: 209 | HSA | CTTTTATCTTCTTATATTGTCCAAGGTCGTATGCAAGCG |
| SEQ ID NO.: 210 | HSA | GATTAATCAGTATTCCCGTTCGTTTCTGGCAACATTTACA |
| SEQ ID NO.: 211 | HSA | TAGGAATCGGATTATGAAATTGTGGCCCAGGTATCGTCA |
| SEQ ID NO.: 212 | HSA | TGATTTTTTGAGGGTTAACTAATTTATATCTGTGTTTT |
| SEQ ID NO.: 213 | Hemoglobin | AGGGTCGTTGGGGCCAGGGTTCACGCGCCGCTCCCCGCT |
| SEQ ID NO.: 214 | Hemoglobin | GCTGATTCGTTCAGATCTCTATTCTCCTTATTATCGACA |
| SEQ ID NO.: 215 | Hemoglobin | GTGATAGGGAAGTGAGTGCTGGCCCGTAGCGACCCTGGAA |
| SEQ ID NO.: 216 | Hemoglobin | CAGGAGCGTAATAATCTCGAGAACGTGTGGCAAACGATAC |
| SEQ ID NO.: 217 | Hemoglobin | AATGGTGATGATTCTCGTTATTCGTTCAGCCTCTA |
| SEQ ID NO.: 218 | IgM-BAS | CGGCTGTCCCGGCCAGGGGCGGGGCGCGGTGCGCTAAT |
| SEQ ID NO.: 219 | IgM-BAS | GCGGGCGCGCAGCGCCACGGGACCGGCCCGCCGGGGGC |
| SEQ ID NO.: 220 | IgM-BAS | CCAATGTGGTGAATAGGAATGTTTCACCGCTTAGGATAAA |
| SEQ ID NO.: 221 | IgM-BAS | CGGGGAAATTAGGGAGGGTATCTTCGTTGGTCCTCCGGCC |
| SEQ ID NO.: 222 | IgM-BAS | GTTCGTCAAAAATAGAGTGTTTTATGACACAGGAATCCGA |
| SEQ ID NO.: 223 | IgM-BAS | GAAAATGGTATATTCGAGTTCTGTGGCATATGGGGCCAT |
| SEQ ID NO.: 224 | IgM-BAS | GTTTGTTTCTTTACGGCATGGGTCATCTATCCCAATTACC |
| SEQ ID NO.: 225 | IgM-BAS | CTACAAAATTGACAAATCTACTTTTGTGTATTCAAGTTAT |
| SEQ ID NO.: 226 | IgM-BAS | GAAGGACTGAAAGAGGACGGAGCGTAGCGGCGTACAGAAC |
| SEQ ID NO.: 227 | IgM-BAS | ATGTGTAATTTTTTACCAAAGCCAAAGCATTTTCCAATG |
| SEQ ID NO.: 228 | IgM-BAS | AGGATTGTAATATTGATATCCTGATTCGTTTAATTTGAGC |
| SEQ ID NO.: 229 | IgM-BAS | TCCCGTATAGTTACTATTCTTTTATTACTGAATAAGCGAA |
| SEQ ID NO.: 230 | IgM-BAS | CTGTTCTATCTTTTCAAGAATGTCCCATCAGTCAATGCCG |
| SEQ ID NO.: 231 | IgM-BAS | TCGTCTGTGTCTCAAAAGTGTATCTAGTGATGCCCCAGAT |
| SEQ ID NO.: 232 | IgM-BAS | GATAATTTATGGTTAACGAGTTCTTCAGTTGAGGGATTT |
| SEQ ID NO.: 233 | IgM-BAS | TGTTCTATTTAATGATTTGTCAACACGATCGGATCTACTG |
| SEQ ID NO.: 234 | IgM-BAS | TTCTGATTGGGTCTTTTGATGTTTTATGAAATCATGCA |

TABLE 1-continued

| | TARGET | 5' to 3' Sequence |
|---|---|---|
| SEQ ID NO.: 235 | IgM-BAS | GAGTTTTTTAAAAGAACAGTTTCATCTCCTCAGTCTTAC |
| SEQ ID NO.: 236 | IgM-BAS | GTTCATATTTAATCTACTGTATTCCTATTATATGTTTAGG |
| SEQ ID NO.: 237 | IgM-BAS | ATCTGGATATAATTAAGTGGGTCAACAGA |
| SEQ ID NO.: 238 | IgM-BAS | ATTTTCAAGTATTAACATTATTAGATAGTTTCAAGAGCC |
| SEQ ID NO.: 239 | IgM-BAS | GATATTTTGAAATGATTATCCTAGACATCTGATTAGCTAT |
| SEQ ID NO.: 240 | IgM-BAS | GGAAAGGAGAAAAGAGGGGAGCAGTGAGTCGTATTA |
| SEQ ID NO.: 241 | HyHel5_IgG | ATATAGCGCAACCGAGGGGTAGGACGTGCACCCCAGAGCC |
| SEQ ID NO.: 242 | HyHel5_I9G | GGGGGATATTCAAGTCTCCCCTCATTGTATCCCTACCCTT |
| SEQ ID NO.: 243 | HyHel5_I9G | ATAAACATGAAGGGGTGGCGCTGGCAGTCATAATTGAAC |
| SEQ ID NO.: 244 | HyHel5_I9G | TTCCAGCGAGGTGGTGCTTAATGAGTCCCGAAAATGTTCT |
| SEQ ID NO.: 245 | HyHel5_I9G | GTCGGGAGTAGAGTGGAAGCGAGGAAGGGGGCAAAACACA |
| SEQ ID NO.: 246 | LAP(TGF-b) | CCGATGTAGGAGTGAGGCCTAGGTTGACTGCGAGACGCTAACCC |
| SEQ ID NO.: 247 | LAP(TGF-b) | CATGACAACTAGGTTTCAAAAGGTCTTTAGATAAAGTCCC |
| SEQ ID NO.: 248 | LAP(TGF-b) | CCGCGGGCTTCCAGTATCTCTGGGTACACTACTGGTCAGT |
| SEQ ID NO.: 249 | LAP(TGF-b) | GCGAGGATGTCCAAATGCATGGAAAGTAACAGCTCCAAGC |
| SEQ ID NO.: 250 | LAP(TGF-b) | CCGATGTAGGAGTGAGAACGACAAACAATCCTTGAGCTGCAATC |
| SEQ ID NO.: 251 | LAP(TGF-b) | CCGATGTAGGAGTGAGGACACATGTGAAAAGACATAATTTATTGGG |
| SEQ ID NO.: 252 | LAP(TGF-b) | CCGATGTAGGAGTGAGACAACCTGTCATTGACTTCTTAGCTA |
| SEQ ID NO.: 253 | LAP(TGF-b) | ACCATCTCTATTGTTGGCACAAATTTGGCCTGCTACATTC |
| SEQ ID NO.: 254 | LAP(TGF-b) | CCGATGTAGGAGTGAGAAGACGGGCATTGGATATACCAGCTTATTCAA |
| SEQ ID NO.: 255 | LAP(TGF-b) | CCGATGTAGGAGTGAGAAAACAATCGACCCTATATACCAGCTTATTCAA |
| SEQ ID NO.: 256 | LAP(TGF-b) | CCGATGTAGGAGTGAGATGCGTGTTATACCAGCTTATTCAA |
| SEQ ID NO.: 257 | LAP(TGF-b) | GCCGTCTTCGATGTGTATCTGCTATGTTAAGGGGACGAGG |
| SEQ ID NO.: 258 | LAP(TGF-b) | CCGATGTAGGAGTGAGACTAACCCCGTATACCAGCTTATTCAA |
| SEQ ID NO.: 259 | LAP(TGF-b) | GTAAGTCAAACAGTCATCTATCATTCTTATGTCCACTTTT |
| SEQ ID NO.: 260 | LAP(TGF-b) | GCCTCTTTGACGTGATGTTCGCTCTTATGACCACATTCAT |
| SEQ ID NO.: 261 | hCG | TTTTCATTGCTACAAAGTCATTTTGTAGGTAACGGTGGAT |
| SEQ ID NO.: 262 | hCG | ATCTCGGGTGGCCCTTCTAGTGGGAGCATCTCCACTGAAA |
| SEQ ID NO.: 263 | hCG | TTTCGCGTATATCACGTCGTATTCAGGAGTAACATTCTAA |
| SEQ ID NO.: 264 | hCG | CACAATCAATGTAACATTGCCAATAGTAAATTGAAATCCT |
| SEQ ID NO.: 265 | hCG | CCGATGTAGGAGTGAGGTGCATTCCCGGCTCGTATACCAGCTTATTCA |
| SEQ ID NO.: 266 | hCG | CCGATGTAGGAGTGAGCGCCGAAAACTGCGAAAGCGACACCG |
| SEQ ID NO.: 267 | hCG | CCAATGTAGGAGTGAGAGAAAGCGCGGCTGATATACCAGCTTATTCAA |
| SEQ ID NO.: 268 | hCG | CCGATGTAGGAGTGAGGGACGCCTATACCAGCTTATTCA |
| SEQ ID NO.: 269 | hCG | CACCCAATGGGGTAAGAGTTGGAATTTACTAACCACCGGA |
| SEQ ID NO.: 270 | hCG | CCGATGTAGGAGTGAGGGTGCAATGGTACTGCCCTTCCCTTGG |
| SEQ ID NO.: 271 | hCG | AACGGAAAAGTCATACGCGCTTACGATATCGGTTGTCGTA |
| SEQ ID NO.: 272 | hCG | TCCGCGAATCTTATAACGGTTCTTCCCTAATGTACATAGG |
| SEQ ID NO.: 273 | hCG | CTCATTTAATATAAATNGGATTAGGTGAAAAGTTTCGCTA |

TABLE 1-continued

| | TARGET | 5' to 3' Sequence |
|---|---|---|
| SEQ ID NO.: 274 | hCG | ATCCACCAAAACGGAGTTGCTCGTAATTTATTCATCAACT |
| SEQ ID NO.: 275 | hCG | CCGATGTAGGAGTGATACGCTGTGTGGCACCAACA |
| SEQ ID NO.: 276 | hCG | ACTGAGGTCTGTCCGTTTACTATGTGAAGGTCCAATAATC |
| SEQ ID NO.: 277 | hCG | CCGATGTAGGAGTGAGGCTAACCCCGTATACCAGCTTATTCAA |
| SEQ ID NO.: 278 | hCG | TGTGTAGAGAATCCCGAGTTTGCACGATGTTCCCTAGCGC |
| SEQ ID NO.: 279 | hCG | CCGATGTAGGAGTGAGGGGACATATAACCTATACCTATACCAGCTTATTCAA |
| SEQ ID NO.: 280 | hCG | CCGATGTAGGAGTGAGGGTTGAATTGGTTATCGAGACATTGGCG |
| SEQ ID NO.: 281 | hCG | CCACAGTTCCAATGTTCTTTATACTCGCGTTGAATCTAAG |
| SEQ ID NO.: 282 | Hemoglobin (glycated) | CGTAGGACACCCTCAAGAAAAGGGTATTGACCCGGGATAT |
| SEQ ID NO.: 283 | Hemoglobin (glycated) | CCCGTAATTCGCTAATTGCTAGATAACTAGAATCGACTCA |
| SEQ ID NO.: 284 | Hemoglobin (glycated) | GTGAACGGATATCTTTATTCGGCATCTTAGGTAGTCTTAA |
| SEQ ID NO.: 285 | Hemoglobin (glycated) | TTCATTCATTAGCAGACCCAACTGTAATTCAGCCTGTATG |
| SEQ ID NO.: 286 | Hemoglobin (glycated) | CCGATGTAGGAGTAAGACCGCGTGTATACCAGCTTATTCAA |
| SEQ ID NO.: 287 | Hemoglobin (glycated) | TTTGCTATGACATAAAAGGATTTTCGAACAGGAGGCCCAA |
| SEQ ID NO.: 288 | Hemoglobin (glycated) | CCACTTGTAATTTCGATACATTGCGTACTTTCTGCAGGCA |
| SEQ ID NO.: 289 | Hemoglobin (glycated) | CTGAAGTGGCCTTAACCTCAGTGGCAATTTGTAAAAGTA |
| SEQ ID NO.: 290 | Hemoglobin (glycated) | TTGCTCGCTAAATTTGTTTATGCCTCTTTTTGCCAGTATA |
| SEQ ID NO.: 291 | Hemoglobin (glycated) | CTCGATCCGGATAAAAAGCATCTTCCACTCTTTCTACTAA |
| SEQ ID NO.: 292 | Synuclein, gamma | GATTATAATTATTAATTATTGTCACGGTAAGTCCAAAGTC |
| SEQ ID NO.: 293 | Synuclein, gamma | TCGCATTTAGATAATTGTCATTTTACGACTTCATACCTTA |
| SEQ ID NO.: 294 | Synuclein, gamma | GGATGTTTAACGGTTGTCTATATCCCTCTTACACCAATCA |
| SEQ ID NO.: 295 | HER2 | CTTGATTTTTAATGACTCAGTAAAATGTC |
| SEQ ID NO.: 296 | Peroxiredoxin4 | CGGTTTATGGTCGTAAAAACTTTACGCTTACCCTTCTTTT |
| SEQ ID NO.: 297 | Peroxiredoxin4 | GTGTTTTGAATTTATTAAATTGGAAACTACCCGTGCACTT |
| SEQ ID NO.: 298 | Peroxiredoxin4 | CGTAAGAGGGAGATTCCTACAAACGCTCCCCATCC |
| SEQ ID NO.: 299 | Peroxiredoxin4 | GGTCTTTTTTTTTTGAATACTTGGGTCGAGTTTCGCCA |
| SEQ ID NO.: 300 | Peroxiredoxin4 | CGATTTTATTGTAATCCATTGGTCACCAACGGTTCAAGA |
| SEQ ID NO.: 301 | Peroxiredoxin4 | AAGGTTTTTAACCCTCTCGAAAAGTATCATCCTCAATCC |
| SEQ ID NO.: 302 | Peroxiredoxin4 | GCGTTAAATGAATAATTCTTTTTAATTTCTTTTACTTG |
| SEQ ID NO.: 303 | Peroxiredoxin4 | GCGGAATGATTTGTTTTAATACGTCGACAGCATTGCAA |
| SEQ ID NO.: 304 | Peroxiredoxin4 | GAATTTTTTCTTAAAAGCTAATTTCCCTTCGCTCACATC |
| SEQ ID NO.: 305 | Peroxiredoxin4 | CGATTTTTTGGAATAAGTCACTGTGAATGGAAACATAT |
| SEQ ID NO.: 306 | Peroxiredoxin4 | TGTTAAGATAATTAAGTGTCACCGTCTATACTAAATTT |
| SEQ ID NO.: 307 | Peroxiredoxin4 | TAGTTGTTTATTTATTCTCATGTTTCGGAGCGTTAACT |

TABLE 1-continued

| | TARGET | 5' to 3' Sequence |
|---|---|---|
| SEQ ID NO.: 308 | Peroxiredoxin4 | CAAAGATTTGATAGTTAACGGTTATTGATTTTCACTCTC |
| SEQ ID NO.: 309 | Peroxiredoxin4 | AATTTTTCGAGTTATGAATATTTCGCCTCTTACTCTTT |
| SEQ ID NO.: 310 | Interleukin18 | GTATTTTTTGGTTGTAAAAAAAGTATCACACTAATTTG |
| SEQ ID NO.: 311 | Interleukin18 | GGAAAGGGGAAAAGGGGGGAGCGGTG |
| SEQ ID NO.: 312 | Crystalin,alphaB | CGTAGGAGGGAGTTCCAATGATACATCCTAACCGATAC |
| SEQ ID NO.: 313 | Crystalin,alphaB | GTTCTTTTTTTTACACTAACGGTTTAGTAAACTCTTCGCC |
| SEQ ID NO.: 314 | Crystalin,alphaB | GTTCTTTTTTTTACACTAACGGTTTAGTAAACTCTTCGCC |
| SEQ ID NO.: 315 | Crystalin,alphaB | AATAATTATGTTCAGCGATACTTCTATTTCCAACTAGCG |
| SEQ ID NO.: 316 | Fascinhomolog1 | CAGTTTTATGTTGGTTAATCCTGGGGCATAGCGCGTTTT |
| SEQ ID NO.: 317 | Fascinhomolog1 | GTTATTTCTTAAAATATAATACTTC |
| SEQ ID NO.: 318 | Fascinhomolog1 | CGCTTAAAATTTCTCTGTTTTCTGGTAGTAGCGCAATAAG |
| SEQ ID NO.: 319 | Fascinhomolog1 | GTTCTTTATTAAGATGTATTCTATAAGTATTTCAAGTTAA |
| SEQ ID NO.: 320 | Fascinhomolog1 | CAAAGATTTTAGTAACATCTAGATGGCACGTGATATTTC |
| SEQ ID NO.: 321 | Fascinhomolog1 | TCCTTTTCAATATTCTTCAACTGAACCTTCGTCATTCA |
| SEQ ID NO.: 322 | Fascinhomolog1 | GGAATATTTTATGGCACTTATTAAACAATTGGTCAAAGTC |
| SEQ ID NO.: 323 | Fascinhomolog1 | GGTCTTCTTTGAGTATTCCTAGTTCTTTGGGGCATTAGTA |
| SEQ ID NO.: 324 | Fascinhomolog1 | NGAGTTTNNGTTTTTAGACATTTTTACCTAACTAGCACGTA |
| SEQ ID NO.: 325 | Chloride intercellular channel1 | CCATGTTATTTTAATCCTATTTTCAGTACGACTATTACCT |
| SEQ ID NO.: 326 | Glutathione S transferase pi | GTTAGTAACGGTCAGTTTAATTAAGAACATTTGCTACGAC |
| SEQ ID NO.: 327 | Ribonucleotidereductase M2polypeptide | CTAATGATGGTTTTCGCAATTAACGCCATCGAACAAGATC |
| SEQ ID NO.: 328 | Ribonucleotidereductase M2polypeptide | CTTATTTAATTGACTTTTAGTAAATGTTTTTCAGTTTTAA |
| SEQ ID NO.: 329 | Ribonucleotidereductase M2polypeptide | CTAATTTTAAATCAGTATTTTTTTCATTCTATCGCACTAT |
| SEQ ID NO.: 330 | Ribonucleotidereductase M2polypeptide | GTCTGATCTCTTTGAATCTTTTACCGCATATACTGTTCGT |
| SEQ ID NO.: 331 | Clusterin | ACCATTTGATGGTTTTCCCTAATTACCAGTTTAATATTAA |
| SEQ ID NO.: 332 | Clusterin | CGGATTTTTAGAGTCTTGAAATAGTTTTCTGTCTCCAGAC |
| SEQ ID NO.: 333 | p10 | CGTAGGAGGGAGATCCCTACAAAC |
| SEQ ID NO.: 334 | p11 | CTTTTTTATGAATTCCCTTTAACGCTCTTTGATACATTC |
| SEQ ID NO.: 335 | p12 | CGTAGGAGGGAGATTCCTACAAAC |
| SEQ ID NO.: 336 | p13 | CGTAGGAGGGAGGTTCCTGCAAAC |
| SEQ ID NO.: 337 | p14 | CGTAGGAGGGAGATTCCTACGAAC |
| SEQ ID NO.: 338 | p15 | CGTAGGAGGGAGATTCCTACAAAC |
| SEQ ID NO.: 339 | p16 | CGTAGGAGGGAGATTCCTACAAAC |
| SEQ ID NO.: 340 | p17 | CGTAGGAGGGAGATTCCTACAAAC |
| SEQ ID NO.: 341 | p18 | CGTAGGGGGAGATTCCTACAAAC |
| SEQ ID NO.: 342 | p19 | CGTAGGAGGGAGATTCCTACAAAC |
| SEQ ID NO.: 343 | p2 | CGTAGGAGGGAGATTCCTGCAAAC |

TABLE 1-continued

| | TARGET | 5' to 3' Sequence |
|---|---|---|
| SEQ ID NO.: 344 | p20 | CTATTCTTGGTTTAACGGCTTATTATAACC |
| SEQ ID NO.: 345 | p21 | CGTAAGAGGGAGATTCCTACAAAC |
| SEQ ID NO.: 346 | p22 | CAAGGGTTTTTAAGTGGTTCGGCGAAGTGACACGTCGTTT |
| SEQ ID NO.: 347 | p23 | CGTAGGAGGGAGATTCCTACAAGC |
| SEQ ID NO.: 348 | p24 | GTTTAAAATTATTAACTGTGTTGTCCTAGTCTTGTTCA |
| SEQ ID NO.: 349 | p25 | GTTTAAGTGGTTATTGAGACATTTTTAATCCGAAATC |
| SEQ ID NO.: 350 | p26 | GTGATTTATTAGGAATCAAGTCTAAGAGCATAT |
| SEQ ID NO.: 351 | p27 | CGTAGGAGGGAGATTCCTACAAGC |
| SEQ ID NO.: 352 | p28 | CTTTTTTAAGTTGAGTATATGGGTAAA |
| SEQ ID NO.: 353 | p29 | GGATATCTTTTTTTGATACTCTGATGAATC |
| SEQ ID NO.: 354 | P3 | CGTAGGAGGGGATTCCTACAAAC |
| SEQ ID NO.: 355 | p30 | CGTAGGAGGGAGATTCCTACAAACGCTCCCCA |
| SEQ ID NO.: 356 | p31 | CGAAATAGTTTTAATTGTTGTATCCCG |
| SEQ ID NO.: 357 | p32 | NNTGATTTATTAGGAATCAAGTCTAANAGCATAT |
| SEQ ID NO.: 358 | p33 | CGAAGGAGGGAGATTCCTACAAAC |
| SEQ ID NO.: 359 | p34 | TCGATTTTGTATAATTCTTTATACCCTTTGGTCTTGTC |
| SEQ ID NO.: 360 | p35 | CGTAGGAGGGAGATTCCTACAAAC |
| SEQ ID NO.: 361 | p36 | CGTAGGAGGGAGATTCCTACAAAC |
| SEQ ID NO.: 362 | p37 | CGTAGGAGGGAGATTCCTACAAAC |
| SEQ ID NO.: 363 | p38 | CGTAGGAGGGAGATTCCTACAAAC |
| SEQ ID NO.: 364 | p39 | CGTAGGAGGGAGATTCCTGCAAAC |
| SEQ ID NO.: 365 | p4 | CGTAGGAGGGAGGTTCCTACAAAC |
| SEQ ID NO.: 366 | p40 | CGTAGGAGGGAGATTCCTGCAAAC |
| SEQ ID NO.: 367 | p41 | GGGAGGGAGGGGCGACGGCCAGGAGCG |
| SEQ ID NO.: 368 | p42 | CGTAGGAGGGAGATTCCTACAAACGCTCTCCATCC |
| SEQ ID NO.: 369 | p43 | CGTAGGGGGAGATTTCTGCAAAC |
| SEQ ID NO.: 370 | p44 | CGTAGGAGGGAGATTCCTGCAAAC |
| SEQ ID NO.: 371 | p45 | CGTAGGAGGGGATTCCTACAAAC |
| SEQ ID NO.: 372 | p46 | CGTAGGAGGGAGATTCCTACAAAC |
| SEQ ID NO.: 373 | P5 | CGTAGGAGGGAGATTCCTACAAGCACTC |
| SEQ ID NO.: 374 | p6 | CGTAGGAGGGAGATTCCTACAAAC |
| SEQ ID NO.: 375 | P7 | TCTAATATGTTTTATAAACTCGGTTTTACCGTCTCG |
| SEQ ID NO.: 376 | p8 | CGTAGGAGGGAGATTCCTACAAAC |
| SEQ ID NO.: 377 | P9 | TGATCTTATTTAGAAACTCCCTTCCGTTGGGAGGGACCAG |
| SEQ ID NO.: 378 | HyHel5IgG | CCGATGTAGGAGTGAGGAGAGC |
| SEQ ID NO.: 379 | LAP(TGF-b) | CCGATGTAGGAGTGAGGTCTTGCCTCGGGATTACAGATGCGCCCG |
| SEQ ID NO.: 380 | LAP(TGF-b) | CCGATGTAGGAGTGAGTAATGATCAAAGTCAGGAACCGCGTTCCC |
| SEQ ID NO.: 381 | LAP(TGF-b) | CCGATGTAGGAGTGAGCCGGAT |
| SEQ ID NO.: 382 | hCG | CCGATGTAGGAGTGAGGGCTCCAGTATTCTATACCAGCTTATTCAA |

TABLE 1-continued

| | TARGET | 5' to 3' Sequence |
|---|---|---|
| SEQ ID NO.: 383 | hCG | CCGATGTAGGAGTGAGGTGGACTAACCATATACCAGCTTATTCAA |
| SEQ ID NO.: 384 | hCG | CCGATGTAGGAGTGAGGTGGACTAACCATATACCAGCTTATTCAA |
| SEQ ID NO.: 385 | hCG | CCGATGTAGGAGTGAGGAAGATTTCCACTATACCAGCTTATTCAA |
| SEQ ID NO.: 386 | hCG | CCGATGTAGGAGTGAGGATACGTTCGAATGGCTTACATCATACCCC |
| SEQ ID NO.: 387 | hCG | CCGATGTAGGAGTGAGGCTAACCCCGTATACCAGCTTATTCAA |
| SEQ ID NO.: 388 | hCG | CCGATGTAGGAGTGAGGCTAACCCCGTATACCAGCTTATTC |
| SEQ ID NO.: 389 | hCG | CCGATGTAGGAGTGAGGCTAACCCCGTATACCAGCTTATTC |
| SEQ ID NO.: 390 | hCG | CCGATGTAGGAGTGAGACCGCTG |
| SEQ ID NO.: 391 | hCG | CCGATGTAGGAGTGAGGGCCTGTTTTATACCAGCTTATTCAA |
| SEQ ID NO.: 392 | hCG | CCGATGTAGGAGTGAGCCCAGT |
| SEQ ID NO.: 393 | hCG | CCGATGTAGGAGTGAGCCCAGT |
| SEQ ID NO.: 394 | hCG | CCGATGTAGGAGTGAGCCCAGT |
| SEQ ID NO.: 395 | hCG | CCGATGTAGGAGTGAGCCCAGT |
| SEQ ID NO.: 396 | hCG | CCGATGTAGGAGTGAGCCCAGT |
| SEQ ID NO.: 397 | hCG | CCGATGTAGGAGTGAGCCCAGT |
| SEQ ID NO.: 398 | hCG | CCGATGTAGGAGTGAGCCCAGT |
| SEQ ID NO.: 399 | Hemoglobin(glycated) | CCGATGTAGGAGTGAGGCTGGCAGTATACCAGCTTATTCAA |
| SEQ ID NO.: 400 | Hemoglobin(glycated) | CCGATGTANGAGTGAGCTAATAAA |
| SEQ ID NO.: 401 | Fibrinogen | CAATATGTCTAATTTTTTTACATGGCGGCATGGTATTGGC |
| SEQ ID NO.: 402 | Fibrinogen | CAATACAATACTATATTTGTGTCAATCTCGTACTTCTGAC |
| SEQ ID NO.: 403 | Fibrinogen | TAATTATCTCCTTAATCATGGTTATTCTTTGAATCTATCA |
| SEQ ID NO.: 404 | Fibrinogen | ATAGTCTAATACAACTTAAAGCAATTCCATGATTATAAAT |
| SEQ ID NO.: 405 | Fibrinogen | ATTCGTTTACATTATTCGGCAATTCTTATTTCTGTTGGAG |
| SEQ ID NO.: 406 | Collagen | AGAGGCGGCTGAGATCAATCTCCGCTCAGGGAGCGAGTA |
| SEQ ID NO.: 407 | Collagen | GTAATAGGTGATTTCCTCAATTTGAATTAGATCACAAAAT |
| SEQ ID NO.: 408 | Fibronectin | CATGTGATGCTCACGGTGGCACCCCAGGCGAGTACGCAGT |
| SEQ ID NO.: 409 | Fibronectin | GATGGTGTTTGTACACAACTTTACATTTTAGTCCTACAAG |
| SEQ ID NO.: 410 | Fibronectin | CAAGAGTGTTAGACATTATCTCAGCGCTGCCAATTATATT |
| SEQ ID NO.: 411 | Fibronectin | CCTTGCGACAAAACCCTCGGGACCTCTATCAAGCCAACGT |
| SEQ ID NO.: 412 | Acetyl-BSA | ACCATATGAATACAACACCATTCAGTTTATTATCCTTTT |
| SEQ ID NO.: 413 | Acetyl-BSA | AAGATCTTTATTAAGCAAACAATGTTAACTATAGAGCGTT |
| SEQ ID NO.: 414 | Acetyl-BSA | GAATTACATTCAAAAATTTTCTTCTGGCATCTGTAATACC |
| SEQ ID NO.: 415 | Acetyl-BSA | ACAATGTATAATTATATCGATTCAGATTAGTCTACAGGAC |
| SEQ ID NO.: 416 | Heparan Sulfate | CACAGAATGTGGATATTTTCTTGCATCTCTTCCTTTTAGT |
| SEQ ID NO.: 417 | Heparan Sulfate | TAGCGCAATTCGTAGTTTCAGGTATCTGGATTCAGGCCGT |
| SEQ ID NO.: 418 | Heparan Sulfate | GTAATCGCGTTACTACTATCTCTCCGTCCACTTTCAATAC |
| SEQ ID NO.: 419 | Heparan Sulfate | CAAAGTAAAATTAACAGATAGTACGTTCTCAATCTCGCGA |

TABLE 1-continued

| | TARGET | 5' to 3' Sequence |
|---|---|---|
| SEQ ID NO.: 420 | Heparan Sulfate | CTGGGCATTTCTAAGGAGTCATACAACTATTTCAGGTTAT |
| SEQ ID NO.: 421 | Heparan Sulfate | TGATACAAATACTCTCAATCAAAGCCAATATGTCGCAAAA |
| SEQ ID NO.: 422 | PIF-HALSA- | GCAGGGCGCGACTCGGCGTGGAACGAGGTTCAATAGTCCA |
| SEQ ID NO.: 423 | PIF-HALSA- | ATCAAGAATTGATAATTTTAGGAATTGCGTATCGCTGCTA |
| SEQ ID NO.: 424 | PIF-HALSA- | TAGTTTATCAGGAGCGATCACTGATCATGAGTAACTTTTA |
| SEQ ID NO.: 425 | PIF-HALSA- | GTTTAGTTAAAATCCGTTTGAGAACAAATTACAAACCTTA |
| SEQ ID NO.: 426 | PIF-HALSA- | AAAAGTCGTAATAGCCCGGGACAACGCCAGCTAAAAGAAA |
| SEQ ID NO.: 427 | PIF-HALSA- | CCGCATTTATCAGTTTACCGCCCCATAAACATAACCGCT |
| SEQ ID NO.: 428 | PIF-HALSA- | ATGTACTTCACTTCAGTTTTCTTTAAACACGTTTCACATA |
| SEQ ID NO.: 429 | PIF-HALSA- | CGTCAGTCTGCTTTCTTGGCTTGTGTACTTAATAATAAGG |
| SEQ ID NO.: 430 | PIF-HALSA- | AACCAGTAAGGTCAGAGTAATAGTATGCCAGTCTTGATCT |
| SEQ ID NO.: 431 | PIF-HALSA- | AATTATGCTCATGATTTTCTTCAAAAAGGCTCGCGCAATT |
| SEQ ID NO.: 432 | PIF-HALSA- | AGAATTTTTAAGGGTTATCTCAAGTCTTGAACATCTAACG |
| SEQ ID NO.: 433 | PIF-HALSA- | GGCTGTTAAACTTACTTTTCTTCAGTAATTGCCGTTGACA |
| SEQ ID NO.: 434 | PIF-HALSA- | TCTTCTTGCACATATTTTTCTCCGTGAGACATGTAAATA |
| SEQ ID NO.: 435 | PIF-HALSA- | CGTCTAATCAATATTGTTTAATGTATTTTGCCAGACACTA |
| SEQ ID NO.: 436 | PIF-HALSA- | CCCAGAATGTAGCTTACCTTTTTTGATCGTCCCAGTCCTT |
| SEQ ID NO.: 437 | RnaseA | GTGTGCCCGGTCAACGCGTGGGCCGCGTGGTACGGGCGT |
| SEQ ID NO.: 438 | RnaseA | AGCGCGATATTACGGTCTCGAACCAAAACCATCACGGTTC |
| SEQ ID NO.: 439 | RnaseA | ATCGACTTAATTTAAAGTGAAAAGATCCCTTTCCACAAAT |
| SEQ ID NO.: 440 | RnaseA | TCGTTATTAGGTTGAGTAACCCATTCTCTTAGCCGCTATA |
| SEQ ID NO.: 441 | RnaseA | TGGTGTTTTACAAAATGAGTACGTTTTTAATCTCGCCCGG |
| SEQ ID NO.: 442 | RnaseA | CCAGGGTACACATCACGAAATATCTAACCTGATTGCAAAC |
| SEQ ID NO.: 443 | RnaseA | TATCGTTTAGTTTACAACTTTCAAATTTAATAAATCGAAT |
| SEQ ID NO.: 444 | RnaseA | AACTGTGTTTTAGGACTTCATTGTCTTAATTCTCTTCCCT |
| SEQ ID NO.: 445 | RnaseA | CGTATATATAGGACGTTTTTGACAGTTTTATTTATTAAAT |
| SEQ ID NO.: 446 | RnaseA | CGTTCATTGTTGGTATAGTTAAGTTCTGACAGATCAATAA |
| SEQ ID NO.: 447 | RnaseA | ATAGTTTAAATTTAATCTTCTGCCACCCTTCACTTTCA |
| SEQ ID NO.: 448 | Laminin | CCCTGGCCAGGCGGGCGCCCGGCCGCGGGCGTGGGGACG |
| SEQ ID NO.: 449 | Laminin | TTTATATTAAGCAACTTTTTGAGAGTTGATTGATAATTTA |
| SEQ ID NO.: 450 | Laminin | GGTGGATAACTGTGTCTGCTTGCCAGACTACGTCCTCAGA |
| SEQ ID NO.: 451 | Laminin | ACGCGCGGCTGTGGGGAAGGTACAGGTTCCGAACGATGGA |
| SEQ ID NO.: 452 | Laminin | AAAAGAGAGGAACCGGTCTTGGCCTGCTCTAAGATTTTGT |
| SEQ ID NO.: 453 | Laminin | CCGATATTGGATCTAAGTGTTGCATCAACATTAATTCAGA |
| SEQ ID NO.: 454 | Laminin | TTCCTTCGTCTTAATACTGTTGCCAGTTAATTAATTTGCG |
| SEQ ID NO.: 455 | Laminin | ACAAAGGATGATCTTCTTATCCTTCAACTAGATCCGGTCC |
| SEQ ID NO.: 456 | Laminin | TGGAGTTTATAATACTCGAGGCTAGTAGTGCCATTTTACA |
| SEQ ID NO.: 457 | Laminin | CAAATAATCGTTTTATAATTACCAACACATTTTGGTTAAC |

TABLE 1-continued

| | TARGET | 5' to 3' Sequence |
|---|---|---|
| SEQ ID NO.: 458 | Laminin | ACAGCTCTCACGCTCCGTCAAGACCAATTTCCATTCGGTT |
| SEQ ID NO.: 459 | Laminin | GCACATCTCCCGTTCGACTTTTTTATCTTCGAGCACCTAA |
| SEQ ID NO.: 460 | Laminin | CCATGTAGCACAAAACAACGATATAAGAACTACATTTAGT |
| SEQ ID NO.: 461 | Laminin | TACTCTTGTTTAAACTAGAACAGTAAAATATTAATTCTTA |
| SEQ ID NO.: 462 | Laminin | GGCTTTCTAATCTAACACGATCTCCTCTCCTTACGCCGTG |
| SEQ ID NO.: 463 | Laminin | TAAAATGGATGTTTTGAAAATTCTGGTATCTCGAGTGTC |
| SEQ ID NO.: 464 | Laminin | TATACATTGAGATAAAACCGATCTTGAAATTTTCCGCACG |
| SEQ ID NO.: 465 | Laminin | ACAAGAACTATTTTTATCAAAGACGTCACCAACTTAAGGC |
| SEQ ID NO.: 466 | Laminin | GCTTAGTAAAATCTTTCTTGTCAATTTCGTTATAAGTCC |
| SEQ ID NO.: 467 | IL-7 | TGGCCTAATCTCGGAGACTGGCCGCTGTGGGCGCGGGCCT |
| SEQ ID NO.: 468 | IL-7 | GGTCAATGTCTAGTTATTAAAATATGTTTTCATAACAAAT |
| SEQ ID NO.: 469 | IL-7 | ATATTGTAAATACTCTTCCCTCATACAGATGATCCGGTAA |
| SEQ ID NO.: 470 | IL-7 | CGAGAAACCTACTTATCTTATTCTTCAATTCGATTTATTA |
| SEQ ID NO.: 471 | IL-7 | GCTTACCTTAACAAAATTGCAACCCAACCCTTCACCGGC |
| SEQ ID NO.: 472 | IL-15 | GTGACGGTGATGGTACCCGCACTGCGGCGGCGGCCAGCAG |
| SEQ ID NO.: 473 | IL-15 | TCTAATTATGTTACAAAATAATTGTTATGCTCCGCAAATA |
| SEQ ID NO.: 474 | IL-15 | CTGCCAAGTCATTACAGAATATTAAAATTTGTCATGTATT |
| SEQ ID NO.: 475 | IL-15 | TCATTTAATTGTCCTAAATCTGAAAATTTATTATATTTC |
| SEQ ID NO.: 476 | IL-21 | AAACCTGCAAAATTTAGGGCCAATGTGTGTATTGAACGGG |
| SEQ ID NO.: 477 | IL-21 | ATCAGAAGCTTCGATCTATTCGCCTCATTCACTCACTCTA |
| SEQ ID NO.: 478 | IL-21 | ACCCTATAAGCTGAGATAAGCATTCTGTGGACGAAAAGTT |
| SEQ ID NO.: 479 | IL-21 | GGTCGAAACAGAGAAGCCTCAAACTTAAACTTCCAATGTG |
| SEQ ID NO.: 480 | IL-21 | AATTTCATTCTTTAAATTGTTTTCTTAATTTTAGCTTA |
| SEQ ID NO.: 481 | IL-21 | TCGTATTTACCCCTATTAACATCAGATCGTGTCATAACGC |
| SEQ ID NO.: 482 | IL-21 | GTTATAGTAATATTGGTTCTAGCTCTCAGTAATATCAAAA |
| SEQ ID NO.: 483 | IL-7R | ACGGAGATTGATTCTGTTTAAAACGGTACTATATCTTGTT |
| SEQ ID NO.: 484 | IL-7R | GCACTATTTTTGACGTAACTCTTCCAATATAAAATCTGCT |
| SEQ ID NO.: 485 | IL-15R | AGGCGTTAACTCTTGTCATGTTATAGACGTCTAATCCATC |
| SEQ ID NO.: 486 | IL-15R | ATAGATTTATTTTTTTTAATTCAAATTCGCTACAGAA |
| SEQ ID NO.: 487 | IL-21R | CGTTAGCGTCGTTTATACTGCAAGTACAAACTTGTAATTG |
| SEQ ID NO.: 488 | IL-21R | ATGGAATATCAGCCATCGTGAATTGCTCAGACTCGAAACG |
| SEQ ID NO.: 489 | IL-21R | ACTGTAATCACTTCTTTTAAATAGTCCCGGAACGATATCA |
| SEQ ID NO.: 490 | IL-21R | CTTGATCCATACTATAACTTAACATTTGTTCATCTCAAGT |
| SEQ ID NO.: 491 | IgG2a-antiCD19- | AGTTTTTGAAATGCATTACAGTATAAACATTTCACACATC |
| SEQ ID NO.: 492 | IgG2a-antiCD19- | CTAAATCGCGAACCGAGTTTTTGTCAAAGTTCTAGATTAA |
| SEQ ID NO.: 493 | IgG2a-antiCD19- | ATTTGAGAAGTTTGACTGCAGTCGCACACTCCCATTTTTG |
| SEQ ID NO.: 494 | IgG2a-antiCD19- | ATGTGTATCGATATGGCCTAACCTAGCTTTAGAACTGGTC |

TABLE 1-continued

| | TARGET | 5' to 3' Sequence |
|---|---|---|
| SEQ ID NO.: 495 | antiCD20 | ATTACTTAAAGATTTGTCATCTCTTTAAAGCTTTGTTA |
| SEQ ID NO.: 496 | antiCD20 | CCAAAAATAGTGATCACATTTTGTGTTCGATAATAACT |
| SEQ ID NO.: 497 | antiCD20 | ACGAACTTTTTAATTCGCAGACATGTTTATAGTTTCTTG |
| SEQ ID NO.: 498 | antiCD20 | ACGAACTTTTTAATTCGCAGACATGTTTATAGTTTCTTG |
| SEQ ID NO.: 499 | HyHel IgG (chicken) | ATAGGAAGGGATTCAGCACGGGCTGTCGTAGACTTCAAGC |
| SEQ ID NO.: 500 | LAP | AGGGTCCGCTAGACGTAGGGGAGAGCCAGAAATCTCAAC |
| SEQ ID NO.: 501 | LAP | CATACCAAGTAGAGACCATACTCTCAGAGGACTGGACGCG |
| SEQ ID NO.: 502 | hCG | TTTTCATTGCTACAAAGTCATTTTGTAGGTAACGGTGGAT |
| SEQ ID NO.: 503 | Non gly Gly Hb | AGGGTCGTTGGGGCCAGGGTTCACGCGCCGCTCCCCGCT |
| SEQ ID NO.: 504 | Non gly Gly Hb | GTGATAGGGAAGTGAGTGCTGGCCCGTAGCGACCCTGGAA |
| SEQ ID NO.: 505 | Hemoglobin (glycated) | GTGATAGGGAAGTGAGTGCTGGCCCGTAGCGACCCTGGAA |
| SEQ ID NO.: 506 | Fibrinogen [Sigma, Cat No. F3879] | GGCGCGCTGGCGCGCGAAGGTGGCTCGGAGTGCTCCGGGC |
| SEQ ID NO.: 507 | Fibronectin | CAAGAGTGTTAGACATTATCTCAGCGCTGCCAATTATATT |
| SEQ ID NO.: 508 | Collagen | AGACTTGAAAGCATCTTTACTTCGATTGGTAATATTTTGAT |
| SEQ ID NO.: 509 | Laminin | TTGAAATTCAATCGCTTAAGTCCCGTTTATAGGAATAACGAT |
| SEQ ID NO.: 510 | Human IL 7 [PeproTech Inc., NJ, Cat No. 200-07] | TGGCCTAATCTCGGAGACTGGCCGCTGTGGGCGCGGGCCT |
| SEQ ID NO.: 511 | Glycated IgM (mu chain) [IgM mu chain from Athens Research, and then glycated in-house] | TTTTATTTCGTATCCTATATTTTCAAGTTAGCTTGACTC |
| SEQ ID NO.: 512 | Non-glycated IgM mu chain [Athens Research] | TTTTATTTCGTATCCTATATTTTCAAGTTAGCTTGACTC |
| SEQ ID NO.: 513 | IgG Fc [Athens Research] | TTGAAGGCGTACCGTCCGCGGGCGGCGTGTGCGCCGGGCC |
| SEQ ID NO.: 514 | Non-glycated HSA | CTCTTAATGTCACGGCTGAGCCTATGCTGGCGTGACCGA |
| SEQ ID NO.: 515 | Non-glycated HSA | GTGTGAAAGCTGGGAGAGTCTGCGGGCCTGTGTCGCGCAA |
| SEQ ID NO.: 516 | Non-glycated HSA | ATGGGTGTGTCTGGGTAGACGTTGTTTTGGCCTGGTGTTA |
| SEQ ID NO.: 517 | Glycated HSA | GTGTGAAAGCTGGGAGAGTCTGCGGGCCTGTGTCGCGCAA |
| SEQ ID NO.: 518 | Glycated HSA | ATGGGTGTGTCTGGGTAGACGTTGTTTTGGCCTGGTGTTA |
| SEQ ID NO.: 519 | Peroxiredoxin | CGTAAGAGGGAGATTCCTACAAACGCTCCCCATCC |
| SEQ ID NO.: 520 | IL 18 | CCCGCAATCCACGACACAGACGACTGCCGTGGACCACCGA |
| SEQ ID NO.: 521 | Crystallin AB | CGTAGGAGGGAGTTCCAATGATACATCCTAACCGATAC |
| SEQ ID NO.: 522 | Crystallin AB | GCGGGGGTTGTGCCCCGTAAAGGCTTGCCAAGCGCCGCA |
| SEQ ID NO.: 523 | Crystallin AB | GGTCAGGTACAGAAGACTGGTGTATGAAGATGCCTGCTAC |

TABLE 1-continued

| | TARGET | 5' to 3' Sequence |
|---|---|---|
| SEQ ID NO.: 524 | RRM2 [Prospec, Catalog#ENZ-523, Swiss-Prot# P31350] | CTAATGATGGTTTTCGCAATTAACGCCATCGAACAAGATC |
| SEQ ID NO.: 525 | EpCAM | CCGCGCAGATATACAACGTACCTCTGTGCGCA |
| SEQ ID NO.: 526 | EpCAM | CTGTGAGGCGTACTGCGGTGAGCCTCTCATTA |
| SEQ ID NO.: 527 | EpCAM | CCCCCCGAATCACATGACTTGGGCGGGGTCG |
| SEQ ID NO.: 528 | EpCAM | GGCCGCGCATTCTCTGCCGGCTGGTGTACGGT |
| SEQ ID NO.: 529 | EpCAM | TGACGGCCATACGTTCATCGTATGTAGTCTTC |
| SEQ ID NO.: 530 | EpCAM | GGCGCAGGGGGGGCCCAGAGTATGGGCCTG |
| SEQ ID NO.: 531 | EpCAM | CGAGGGGCGTGGGCTTCGGGCACCCAGCGGG |
| SEQ ID NO.: 532 | EpCAM | ATGGCTCGGGTCTTACACCCTGGAGGACCGTG |
| SEQ ID NO.: 533 | EpCAM | GGGGCGGGCACTGCCTTCGAGTTGCTCGGTGT |
| SEQ ID NO.: 534 | AptaTecK TEM | CGCATGGGTACCAGTGAGCGATGGACCCTAGC |
| SEQ ID NO.: 535 | Dengue2 protein | CGCAGTGTCGTACCGTCGATGCGGGGATGCCG |
| SEQ ID NO.: 536 | Dengue2 protein | CGCAGAAGGCGTCGGATAGACCCGCAATCACG |
| SEQ ID NO.: 537 | Hsp27 | GCGGTGAACTGCTCGTAAAGCGGGGCAAGACCAGAGGGAT |
| SEQ ID NO.: 538 | Hsp27 | ATGCGATTGTCTCCTAATTATCACTCGCTTACTGGGTCAAT |
| SEQ ID NO.: 539 | H3 K27 (Me3) (aa 21-44) peptide [Anaspec, Cat. No. 64367-025] | CCGATGTAGGAGTGAGGTTGGGCAGCGGGCCCAGCCGAGGCACTCCCCG |
| SEQ ID NO.: 540 | BCM [Human CLEC9a] | GTATCAAGCTTTAGTGGAGAGTACCACTCNCACTAAAACA |
| SEQ ID NO.: 541 | BCM [Human CLEC9a] | CCTACAGTATAGATGAGTCGACCATTAGAAACAATGGTCC |
| SEQ ID NO.: 542 | Mouse CD8 [Sino Biological Inc., Beijing, China [Cat: 50389-M08H] | GCCGTCCCCGCGTTTGGTACGCGGTAGGAGAC |
| SEQ ID NO.: 543 | Mouse CD8 [Sino Biological Inc., Beijing, China [Cat No. 50389-M08H] | GGCGCTTAGTTAGACTAACGTTGCTAGGGGCG |
| SEQ ID NO.: 544 | Heparan Sulfate | CTCGATCAGTACACAGATCGCCTAATGGAGATTTTTCA |
| SEQ ID NO.: 545 | Epirubicin | CACTGGGGTCGGAGATTTCTCGTTGTGGCGGCCGCCGGCG |
| SEQ ID NO.: 546 | Ampicillin | ATTAATATCTAACTAGCGCGCTCGTCTCAATATCGGCAAG |
| SEQ ID NO.: 547 | Tetracycline | GTTTGTGTATTACAGTTATGTTACCCTCATTTTTCTGAAC |

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A ligand to a target molecule comprising a nucleic acid sequence having at least 95% homology or identity to a sequence selected from the group consisting of sequence IDs Seq40, Seq41, Seq42, Seq44, Seq45, Seq46, Seq47, Seq48, and Seq49.

2. A ligand to a target molecule comprising a modified nucleic acid sequence having at least 95% homology or identity to a sequence selected from the group consisting of sequence IDs Seq40, Seq41, Seq42, , Seq44, Seq45, Seq46, Seq47, Seq48, and Seq49.

* * * * *